US011497740B2

(12) United States Patent
Dalvi et al.

(10) Patent No.: US 11,497,740 B2
(45) Date of Patent: Nov. 15, 2022

(54) USE OF JUMONJI C DEMETHYLASE INHIBITORS FOR THE TREATMENT AND PREVENTION OF CHEMOTHERAPY RESISTANCE AND RADIORESISTANCE IN CANCER

(71) Applicant: THE BOARD OF REGENTS OF THE UNIVERSITY OF TEXAS SYSTEM, Austin, TX (US)

(72) Inventors: Maithili P Dalvi, Dallas, TX (US); Elisabeth D Martínez, Dallas, TX (US); John D Minna, Dallas, TX (US); Juan Bayo-Fina, Dallas, TX (US); Amit Das, Dallas, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 16/097,405

(22) PCT Filed: Apr. 28, 2017

(86) PCT No.: PCT/US2017/030132
§ 371 (c)(1),
(2) Date: Oct. 29, 2018

(87) PCT Pub. No.: WO2017/190009
PCT Pub. Date: Nov. 2, 2017

(65) Prior Publication Data
US 2019/0151296 A1 May 23, 2019

Related U.S. Application Data

(60) Provisional application No. 62/329,670, filed on Apr. 29, 2016.

(51) Int. Cl.
| | | |
|---|---|---|
| *A61K 31/444* | (2006.01) |
| *A61K 45/06* | (2006.01) |
| *A61K 31/00* | (2006.01) |
| *A61K 31/44* | (2006.01) |
| *A61P 35/00* | (2006.01) |
| *A61K 33/243* | (2019.01) |
| *A61K 31/282* | (2006.01) |
| *A61K 31/337* | (2006.01) |
| *A61K 31/55* | (2006.01) |
| *A61N 5/10* | (2006.01) |

(52) U.S. Cl.
CPC ........... *A61K 31/444* (2013.01); *A61K 31/00* (2013.01); *A61K 31/282* (2013.01); *A61K 31/337* (2013.01); *A61K 31/44* (2013.01); *A61K 31/55* (2013.01); *A61K 33/243* (2019.01); *A61K 45/06* (2013.01); *A61N 5/10* (2013.01); *A61P 35/00* (2018.01)

(58) Field of Classification Search
CPC ...... A61K 31/444; A61K 31/00; A61K 31/44; A61K 35/00; A61K 33/243; A61K 31/282; A61K 31/337; A61K 31/55; A61K 45/06; A61P 35/00; A61N 5/10
See application file for complete search history.

(56) References Cited

U.S. PATENT DOCUMENTS

| | | |
|---|---|---|
| 2004/0241727 A1 | 12/2004 | Liew |
| 2009/0269773 A1 | 10/2009 | Fantl et al. |
| 2013/0040291 A1 | 2/2013 | Walker et al. |
| 2016/0113911 A1* | 4/2016 | Whetstine .......... A61K 31/7068 514/19.3 |

FOREIGN PATENT DOCUMENTS

| | | |
|---|---|---|
| WO | WO 2006/014755 | 2/2006 |
| WO | WO 2009/075811 | 6/2009 |
| WO | WO 2009/108856 | 9/2009 |
| WO | WO 2011/130331 | 10/2011 |
| WO | WO 2012/037212 | 3/2012 |
| WO | WO 2014/055634 | 4/2014 |
| WO | WO 2014/144850 | 9/2014 |
| WO | WO 2014/170873 | 10/2014 |
| WO | WO 2014/170875 | 10/2014 |

OTHER PUBLICATIONS

Horton, "Characterization of a Linked Jumonji Domain of the KDM5/ JARID1 Family of Histone H3 Lysine 4 Demethylases", The Journal of Biological Chemistry vol. 291, No. 6, pp. 2631-2646, Feb. 5, 2016.*

Arndt et al., "Cold atmospheric plasma, a new strategy to induce senescence in melanoma cells" *Experimental Dermatology*, 2013, 22(4):284-289.

Bartova et al., "Recruitment of Oct4 protein to UV-damaged chromatin in embryonic stem cells" *PLoS One*, 2011, 6(12):e27281.

Batra et al., "Interactionbetween γ-radiation and dietary folate starvation metabolically reprograms global hepatic histone H3 methylation at lysine 4 and lysine 27 residues" *Food and Chemical Toxicology*, 2012, 50(3-4):464-472.

Ben-Porath, et al. "An Embryonic Stem Cell-Like Gene Expression Signature in Poorly Differentiated Aggressive Human Tumors" *Nat. Genet* 2008; 40: 499-507.

Bertolini et al. "Highly tumorigenic lung cancer CD133+ cells display stem-like features and are spared by cisplatin treatment." *Proceedings of the National Academy of Sciences of the United States of America* 2009; 106: 16281-16286.

Bhargavan et al., "Epigenetic repression of LEDGF during UVB exposure by recruitment of SUV39H1 and HDACI to the Sp1-responsive elements within LEDGF promoter CpG island" *Epigenetics*, 2013, 8(3):268-280.

(Continued)

*Primary Examiner* — Sahar Javanmard
(74) *Attorney, Agent, or Firm* — Norton Rose Fulbright US LLP

(57) ABSTRACT

Disclosed are methods for the use of Jumonji C demethylase inhibitors for the radiosensitization of cancers cells and the treatment and prevention of chemotherapy resistance in cancer.

15 Claims, 36 Drawing Sheets

Specification includes a Sequence Listing.

(56) References Cited

OTHER PUBLICATIONS

Biswas et al., "E2F1 responds to ultraviolet radiation by directly stimulating DNA repair and suppressing carcinogenesis" *Cancer Research*, 2014, 74(12):3369-3377.

Bradshaw et al "Clinical relevance of transmembrane drug efflux as a mechanism of multidrug resistance" *Journal of Clinical Oncology: Official Journal of the American Society of Clinical Oncology*, 2007; 16: 3674-3690.

Cetinkaya et al., "Global quantification of heterochromatin-associated histone methylations in cell lines with differential sensitivity to ionizing radiation" *Acta Biochimica Polonica*, 2015, 62(2):173-176.

Chan et al. "Potent and Selective Triazole-Based Inhibitors of the Hypoxia-Inducible Factor Prolyl-Hydroxylases with Activity in the Murine Brain" *PLoS One*, 2015; 10(7): 1-17.

Chaudhuri et al., "Histone H3 Lys79 methylation is required for efficient nucleotide excision repair in silenced locus of *Saccharomyces cerevisiae*" *Nucleic Acids Research*, 2009, 37(5):1690-1700.

D' Amato et al. "Chemotherapy resistance and oncogene expression in non-small cell lung cancer," *The Journal of Thoracic and Cardiovascular Surgery*, 2007; 133: 352-363.

Ding et al. "Enhanced identification and biological validation of differential gene expression via Illumina whole-genome expression arrays through the use of the model-based background correction methodology" *Nucleic Acids Res*. 2008; 36: e58.

Dong et al., "Radioprotective effects of Bmi-1 involve epigenetic silencing of oxidase genes and enhanced DNA repair in normal human keratinocytes" *The Journal of Investigative Dermatology*, 2011, 131(6):1216-1225.

Duan et al., "Histone H3 lysine 14 (H3K14) acetylation facilitates DNA repair in a positioned nucleosome by stabilizing the binding of the chromatin remodeler RSC (Remodels Structure of Chromatin)" *Journal of Biological Chemistry*, 2014, 289(12):8353-8363.

Eisen et al. "Cluster analysis and display of genome-wide expression patterns" *Proceedings of the National Academy of Sciences of the United States of America* 1998; 95: 14863-14868.

Fnu et al., "Methylation of histone H3 lysine 36 enhances DNA repair by nonhomologous end-joining" *PNAS*, 2011, 108(2):540-545.

Galoian et al., "Epigenetic regulation of embryonic stem cell marker miR302C in human chondrosarcoma as determinant of antiproliferative activity of proline-rich polypeptide 1" *International journal of oncology*, 2015, 47(2):465-472.

Gottesman et al. "Multidrug resistance in cancer: role of ATP-dependent transporters" *Nature Review Cancer*, 2002; 2: 48-58.

Guo et al., "Crystallization and preliminary crystallographic analysis of a PHD domain of human JARID1B" *Acta crystallographica. Section F, Structural Biology and Crystallization Communications*, 2011, 67(pt8):907-910.

Guo et al., "GCN5 and E2F1 stimulate nucleotide excision repair by promoting H3K9 acetylation at sites of damage" *Nucleic Acids Research*, 2011, 39(4):1390-1397.

Hashizume et al. "Pharmacologic inhibition of histone demethylation as a therapy for pediatric brainstem glioma," *Nat. Med*. 2014; 1394-1396.

Ho et al. "Side population in human lung cancer cell lines and tumors is enriched with stem-like cancer cells" *Cancer Research* 2007; 67: 4827-4833.

Howlader et al. *SSER Cancer Statistics Review* 1975-2012.

Hu et al., "Histone acetyltransferase GCN5 is essential for heat stress-responsive gene activation and thermotolerance in *Arabidopsis*" *Plant Journal*, 2015, 8(6):1178-1191.

Hwang et al., "Emodin attenuates radioresistance induced by hypoxia in HepG2 cells via the enhancement of PARP1 cleavage and inhibition of JMJD2B" *Oncology Reports*, 2015, 33(4):1691-1698.

International Search Report and Written Opinion issued in Application No. PCT/US2017/030132, dated Jul. 14, 2017.

Iyer et al., "Origin and evolution of peptide-modifying dioxygenases and identification of the wybutosine hydroxylase/hydroperoxidase" *Nucleic Acids Research*, 2010, 38(16):5261-5279.

Jandl et al., "Melanoma stem cells in experimental melanoma are killed by radioimmunotherapy," *Nuclear Medicine and Biology*, 2013, 40(2):177-181.

Jang et al., "Cabin 1 restrains p53 activity on chromatin" *Nature Structural & Molecular Biology*, 2009, 16(9):910-915.

Ji et al., "Lysine-specific demethylase 5C promotes hepatocellular carcinoma cell invasion through inhibition BMP7 expression" *BMC Cancer*, 2015, 15801.

Jin et al., "Histone Demethylase UTX-1 Regulates C. elegans Life Span by Targeting the Insulin/IGF-1 Signaling Pathway" *Cell Metabolism*, 2011, 14(2):161-172.

Kemper et al. "Phenotype switching: tumor cell plasticity as a resistance mechanism and target for therapy," *Cancer Research* 2014; 74: 5937-5941.

Kim et al., "Histone demethylase JMJD2B-mediated cell proliferation regulated by hypoxia and radiation in gastric cancer cell" *Biochimica et biophysica acta*, 2012, 1819(11-12):1200-1207.

Kitajima et al., "Definitive but not primitive hematopoiesis is impaired in jumonji mutant mice" *Blood*, 1999, 93(1):87-95.

Knoechel et al. "An epigenetic mechanism of resistance to targeted therapy in T cell acute lymphoblastic leukemia" *Nat. Genet.*, 2014; 76: 364-370.

Krejci et al., "Epigenetics of multiple myeloma after treatment with cytostatics and gamma radiation" *Leukemia Research*, 2009, 33(11);1490-1498.

Kruidenier et al. "A selective jumonji H3K27 demethylase inhibitor modulates the proinflammatory macrophage response," *Nature*, 2012; 488: 404-408.

Lemontt et al "Increased mdr gene expression and decreased drug accumulation in multidrug-resistant human melanoma cells," *Cancer Research*, 1988, 48: 6348-6353.

Li et al., "Histone demethylase KDM5B is a key regulator of genome stability" *PNAS*, 2014, 111(19):7096-7101.

Li et al., "The histone methyltransferase SDG8 mediates the epigenetic modification of light and carbon responsive genes in plants" *Genome Biology*, 2015, 16:79.

Liang et al., "Dissociation of the H3K36 demethylase Rph1 from chromatin mediates derepression of environmental stress-response genes under genotoxic stress in *Saccharomyces cerevisiae*" *Molecular Biology of the Cell*, 2013, 24(20):3251-3262.

Liang et al., "The histone H3K36 demethylase Rph1/KDM4 regulates the expression of the photoreactivation gene PHR1" *Nucleic Acids Research*, 2011, 39(10):4151-4165.

Lin et al., "Silencing JARID1B suppresses oncogenicity, sternness and increases radiation sensitivity in human oral carcinoma" *Cancer Letters*, 2015, 368(1):36-45.

Liu et al. "Lung cancer tumorigenicity and drug resistance are maintained through ALDH(hi)CD44(hi) tumor initiating cells," *Oncotarget*, 2013; 4: 1698-1711.

Luijsterburg, "Heterochromatin protein 1 is recruited to various types of DNA damage" *Journal of Cell Biology*, 2009, 185(4):577-586.

Mair et al. "Exploiting epigenetic vulnerabilities for cancer therapeutics," *Trends Pharmacol Sci*, 2014; 35: 136-145.

Maroschik et al., "Radiation-induced alterations of histone post-translational modification levels in lymphoblastoid cell lines" *Radiation oncology*, 2014, 9:15.

Martin et al. "Long-term results of combined-modality therapy in resectable non-small-cell lung cancer," *Journal of Clinical Oncology: Official Journal of the American Society of Clinical Oncology*, 2002; 20: 1989-1995.

Massarelli et al. "A retrospective analysis of the outcome of patients who have received two prior chemotherapy regimens including platinum and docetaxel for recurrent non-small-cell lung cancer," *Lung Cancer*, 2003; 39: 55-61.

Meissner et al. "Genome-scale DNA methylation maps of pluripotent and differentiated cells" *Nature*, 2008; 454: 766-770.

Mund et al., "SPOC1 modulates DNA repair by regulating key determinants of chromatin compaction and DNA damage response" *Nucleic Acids Research*, 2012, 40(22):11363-11379.

(56) References Cited

OTHER PUBLICATIONS

Nakamura et al., "Regulation of Homologous Recombination by RNF20-Dependent H2B Ubiquitination" *Molecular Cell*, 2011, 41(5):515-528.
Nottke et al., "SPR-5 is a histone H3K4 demethylase with a role in meiotic double-strand break repair" *PNAS*, 2011, 108(31):12805-12810.
Peng et al., "Molecular characterization of the porcine JHDM1A gene associated with average daily gain: evaluation its role in skeletal muscle development and growth" *Molecular Biology Reports*, 2011, 38(7):4697-4704.
Rant et al., "60Co-γ radiation induces differential acetylation and phosphorylation of histones H3 and H4 in wheat" *Plant Biology* (Berlin, Germany), 2012, 14(1):110-117.
Rho et al, "Epithelial to mesenchymal transition derived from repeated exposure to gefitinib determines the sensitivity to EGFR inhibitors in A549, a non-small cell lung cancer cell line" *Lung Cancer*, 2009; 63: 219-226.
Roesch et al. "A temporarily distinct subpopulation of slow-cycling melanoma cells is required for continuous tumor growth," *Cell*, 2010; 141: 583-594.
Roesch et al. "Overcoming intrinsic multidrug resistance in melanoma by blocking the mitochondrial respiratory chain of slow-cycling JARID1B(high) cells," *Cancer Cell*, 2013; 23: 811-825.
Roninson et al. "Isolation of human mdr DNA sequences amplified in multidrug-resistant KB carcinoma cells" *Proceedings of the National Academy of Sciences of the United States*, 1986; 83: 4538-4542.
Ruesch et al., "The histone H3 lysine 9 methyltransferase DIM-5 modifies chromatin at frequency and represses lightactivated gene expression" *G3*, 2014, 5(1):93-101.
Scagliotti et al. "Phase III study comparing cisplatin plus gemcitabine with cisplatin plus pemetrexed in chemotherapy-naïve patients with advanced-stage non-small-cell lung cancer," *Journal of Clinical Oncology: Official Journal of the American Society of Clinical Oncology*, 2008; 26: 3543-3551.
Schenke et al., "Suppression of UV-B stress responses by flg22 is regulated at the chromatin level via histone modification" *Plant, Cell & Environment*, 2014, 37(7):1716-1721.
Schiller et al. "Comparison of four chemotherapy regimens for advanced non-small-cell lung cancer," *The New England Journal of Medicine*, 2002; 346: 92-98.
Seiler et al., "Double-strand break-induced transcriptional silencing is associated with loss of tri-methylation at H3K4" *Chromosome Research*, 2011, 19(7):883-899.
Sharma et al. "A chromatin-mediated reversible drug-tolerant state in cancer cell subpopulations" *Cell*, 2010; 141: 69-80.
Shen et al. "Quick mining and visualization of next-generation sequencing data by integrating genomic databases" *BMC Genomics*, 2014; 15: 284.
Shien et al. "Acquired resistance to EGFR inhibitors is associated with a manifestation of stem cell-like properties in cancer cells," *Cancer Research*, 2013; 73: 3051-3061.
Sidler et al., "SUV39H1 downregulation induces deheterochromatinization of satellite regions and senescence after exposure to ionizing radiation" *Frontiers in genetics*, 2014, 541.
Stewart et al. "Chemotherapy dose-response relationships in non-small cell lung cancer and implied resistance mechanisms" *Cancer Treat Rev.*, 2007; 33: 101-137.
Subramanian et al. "Gene set enrichment analysis: a knowledge-based approach for interpreting genome-wide expression profiles," *Proceedings of the National Academy of Sciences of the United States of America*, 2005; 102: 15545-15550.
Szakacs et al. "Targeting multidrug resistance in cancer," *Nat. Rev. Drug Discov.* 2006; 5: 219-234.
Takebe et al. "Targeting cancer stem cells by inhibiting Wnt, Notch, and Hedgehog pathways" *Nat Rev. Clin. Oncool.* 2011; 8: 97-106.
Tanaka et al., "Conservation of the syntenies between porcine chromosome 7 and human chromosomes 6, 14 and 15 demonstrated by radiation hybrid mapping and linkage analysis" *Animal Genetics*, 2003, 34(4):255-263.
Tessadori et al., "Phytochrome B and histone deacetylase 6 control light-induced chromatin compaction in *Arabidopsis thaliana*" *PLoS genetics*, 2009, 5(9):e1000638.
Thomson et al. "Epithelial to mesenchymal transition is a determinant of sensitivity of non-small-cell lung carcinoma cell lines and xenografts to epidermal growth factor receptor inhibition," Cancer Research 2005; 65; 9455-9462.
Tong et al., "MnTE-2-PyP reduces prostate cancer growth and metastasis by suppressing p300 activity and p300/HIF-1/CREB binding to the promoter region of the PAI-1 gene" *Free radical biology & medicine*, 2016, 94:185-194.
Vasireddy et al., "γ-radiation-induced γH2AX formation occurs preferentially in actively transcribing euchromatic loci," *Cellular and Molecular Life Science*, 2010, 67(2):291-294.
Villar et al., "Enhancer evolution across 20 mammalian species" *Cell*, 2015, 160(3):554-566.
Voulgari et al. "Epithelial-mesenchymal transition in cancer metastasis: mechanisms, markers and strategies to overcome drug resistance in the clinic," *Biochim Biophys Acta*, 2009; 1796: 75-90.
Wagner et al. "Identification and characterization of small molecule inhibitors of a PHD finger," Biochemistry, 2012; 51(41): 8293-8306.
Wang et al. "A small molecule modulates Jumonji histone demethylase activity and selectivity inhibits cancer growth," *Nat. Commun*, 2013; 4: 2035.
Watanabe et al., "JMJD1C demethylates MDC1 to regulate the RNF8 and BRCA1-mediated chromatin response to DNA breaks" *Nature Structural & Molecular Biology*, 2013, 20(12):1425-1433.
Wilson et al. "AXL inhibition sensitizes mesenchymal cancer cells to antimitotic drugs," *Cancer Research*, 2014; 74: 5878-5890.
Young et al., "Kdm4b histone demethylase is a DNA damage response protein and confers a survival advantage following γ-irradiation" *The Journal of Biological Chemistry*, 2013, 288(29):21376-21388.
Zheng et al., "p53 promotes repair of heterochromatin DNA by regulating JMJD2b and SUV39H1 expression" *Oncogene*, 2014, 33(6):734-744.

* cited by examiner

% of γH2AX and 53BP1 foci remaining after 12 h for a panel of NSCLC treated with JIB-04

Radioresistant NSCLC

| Cell line | Treatment | # Foci/cell remaining after 12 h γH2AX | 53BP1 | |
|---|---|---|---|---|
| H1299 | DMSO | 10.1±2.8 | 14.7±2.1 | *** |
| | JIB-04 | 40.5±8.2 | 40.9±5.3 | |
| A549 | DMSO | 17.2±3.4 | 11.9±2.5 | **** |
| | JIB-04 | 54.9±8.2 | 43.9±3.6 | |
| HCC95 | DMSO | 8.4±2.5 | 12.0±2.1 | * |
| | JIB-04 | 54.3±10.4 | 45.2±12.5 | |
| HCC2279 | DMSO | 33.6±4.6 | 20.2±3.4 | ** |
| | JIB-04 | 57.7±6.7 | 48.2±9.7 | |

Radiosensitive NSCLC

| Cell line | Treatment | # Foci/cell remaining after 12 h γH2AX | 53BP1 |
|---|---|---|---|
| HCC1719 | DMSO | 22.0±5.4 | 20.9±4.9 |
| | JIB-04 | 37.4±7.4 | 39.3±6.9 |
| H2228 | DMSO | 29.6±7.8 | 50.7±11.7 |
| | JIB-04 | 41.2±7.2 | 67.92±9.8 |
| H1395 | DMSO | 41.0±4.0 | 35.8±5.0 |
| | JIB-04 | 42.4±5.8 | 37.3±2.8 |
| H23 | DMSO | 119.2±12.8 | 108.2±21.0 |
| | JIB-04 | 132.2±19.8 | 126.15±17.1 |

FIG. 26C

SEQUENCE LISTING

```
<160> NUMBER OF SEQ ID NOS: 36

<210> SEQ ID NO 1
<211> LENGTH: 24
<212> TYPE: DNA
<213> ORGANISM: Artificial Sequence
<220> FEATURE:
<223> OTHER INFORMATION: Synthetic Primer

<400> SEQUENCE: 1
ctaatgccac acctctctca actc                                                24

<210> SEQ ID NO 2
<211> LENGTH: 24
<212> TYPE: DNA
<213> ORGANISM: Artificial Sequence
<220> FEATURE:
<223> OTHER INFORMATION: Synthetic Primer

<400> SEQUENCE: 2
ctaatgccac acctctctca actc                                                24

<210> SEQ ID NO 3
<211> LENGTH: 19
<212> TYPE: DNA
<213> ORGANISM: Artificial Sequence
<220> FEATURE:
<223> OTHER INFORMATION: Synthetic Primer
```

-continued

<400> SEQUENCE: 3
tccaccggct gataaacca                                                    19

<210> SEQ ID NO 4
<211> LENGTH: 19
<212> TYPE: DNA
<213> ORGANISM: Artificial Sequence
<220> FEATURE:
<223> OTHER INFORMATION: Synthetic Primer

<400> SEQUENCE: 4
agccggaagt cggtcatgt                                                    19

<210> SEQ ID NO 5
<211> LENGTH: 18
<212> TYPE: DNA
<213> ORGANISM: Artificial Sequence
<220> FEATURE:
<223> OTHER INFORMATION: Synthetic Primer

<400> SEQUENCE: 5
gcgctcccac ctcactca                                                     18

<210> SEQ ID NO 6
<211> LENGTH: 21
<212> TYPE: DNA
<213> ORGANISM: Artificial Sequence
<220> FEATURE:
<223> OTHER INFORMATION: Synthetic Primer

<400> SEQUENCE: 6
ccgaagagaa gccgtctatg c                                                 21

<210> SEQ ID NO 7
<211> LENGTH: 24
<212> TYPE: DNA
<213> ORGANISM: Artificial Sequence
<220> FEATURE:
<223> OTHER INFORMATION: Synthetic Primer

<400> SEQUENCE: 7
gtggttttca gcaaccgtta taaa                                              24

<210> SEQ ID NO 8
<211> LENGTH: 23
<212> TYPE: DNA
<213> ORGANISM: Artificial Sequence
<220> FEATURE:
<223> OTHER INFORMATION: Synthetic Primer

<400> SEQUENCE: 8
cagtgacgga tcaacaattt tca                                               23

<210> SEQ ID NO 9
<211> LENGTH: 22
<212> TYPE: DNA
<213> ORGANISM: Artificial Sequence
<220> FEATURE:
<223> OTHER INFORMATION: Synthetic Primer

<400> SEQUENCE: 9
tgcccttgta tcagtcgaca ga                                                22

<210> SEQ ID NO 10

```
<211> LENGTH: 25
<212> TYPE: DNA
<213> ORGANISM: Artificial Sequence
<220> FEATURE:
<223> OTHER INFORMATION: Synthetic Primer

<400> SEQUENCE: 10
gcactagggt ttatgctagg aagct                                    25

<210> SEQ ID NO 11
<211> LENGTH: 19
<212> TYPE: DNA
<213> ORGANISM: Artificial Sequence
<220> FEATURE:
<223> OTHER INFORMATION: Synthetic Primer

<400> SEQUENCE: 11
tcttcacccg caccatgat                                           19

<210> SEQ ID NO 12
<211> LENGTH: 22
<212> TYPE: DNA
<213> ORGANISM: Artificial Sequence
<220> FEATURE:
<223> OTHER INFORMATION: Synthetic Primer

<400> SEQUENCE: 12
agacctgcgt cgtgatgtaa tg                                       22

<210> SEQ ID NO 13
<211> LENGTH: 24
<212> TYPE: DNA
<213> ORGANISM: Artificial Sequence
<220> FEATURE:
<223> OTHER INFORMATION: Synthetic Primer

<400> SEQUENCE: 13
tgcagatgtg aatggtaccc tcta                                     24

<210> SEQ ID NO 14
<211> LENGTH: 23
<212> TYPE: DNA
<213> ORGANISM: Artificial Sequence
<220> FEATURE:
<223> OTHER INFORMATION: Synthetic Primer

<400> SEQUENCE: 14
caccaagtcc aggattgttc tca                                      23

<210> SEQ ID NO 15
<211> LENGTH: 23
<212> TYPE: DNA
<213> ORGANISM: Artificial Sequence
<220> FEATURE:
<223> OTHER INFORMATION: Synthetic Primer

<400> SEQUENCE: 15
ggcctcttca cgcagtacaa tat                                      23

<210> SEQ ID NO 16
<211> LENGTH: 23
<212> TYPE: DNA
<213> ORGANISM: Artificial Sequence
<220> FEATURE:
<223> OTHER INFORMATION: Synthetic Primer

<400> SEQUENCE: 16
```

-continued ccagtatttg cgttcaaggt cat                                                    23

<210> SEQ ID NO 17
<211> LENGTH: 24
<212> TYPE: DNA
<213> ORGANISM: Artificial Sequence
<220> FEATURE:
<223> OTHER INFORMATION: Synthetic Primer

<400> SEQUENCE: 17
gaatgctgtc tctgcaattt gaga                                                   24

<210> SEQ ID NO 18
<211> LENGTH: 18
<212> TYPE: DNA
<213> ORGANISM: Artificial Sequence
<220> FEATURE:
<223> OTHER INFORMATION: Synthetic Primer

<400> SEQUENCE: 18
caacggcgca catgacat                                                          18

<210> SEQ ID NO 19
<211> LENGTH: 26
<212> TYPE: DNA
<213> ORGANISM: Artificial Sequence
<220> FEATURE:
<223> OTHER INFORMATION: Synthetic Primer

<400> SEQUENCE: 19
ctgggtgtat cctctgcata tagaac                                                 26

<210> SEQ ID NO 20
<211> LENGTH: 26
<212> TYPE: DNA
<213> ORGANISM: Artificial Sequence
<220> FEATURE:
<223> OTHER INFORMATION: Synthetic Primer

<400> SEQUENCE: 20
gcagagaatg tcctcagtgt ttagaa                                                 26

<210> SEQ ID NO 21
<211> LENGTH: 20
<212> TYPE: DNA
<213> ORGANISM: Artificial Sequence
<220> FEATURE:
<223> OTHER INFORMATION: Synthetic Primer

<400> SEQUENCE: 21
tgtgttgagc cagcgtatgg                                                        20

<210> SEQ ID NO 22
<211> LENGTH: 21
<212> TYPE: DNA
<213> ORGANISM: Artificial Sequence
<220> FEATURE:
<223> OTHER INFORMATION: Synthetic Primer

<400> SEQUENCE: 22
ccacccggtt aaaagcagac t                                                      21

<210> SEQ ID NO 23
<211> LENGTH: 22
<212> TYPE: DNA

```
<213> ORGANISM: Artificial Sequence
<220> FEATURE:
<223> OTHER INFORMATION: Synthetic Primer

<400> SEQUENCE: 23
tccatcagct tgtgaccatc at                                          22

<210> SEQ ID NO 24
<211> LENGTH: 25
<212> TYPE: DNA
<213> ORGANISM: Artificial Sequence
<220> FEATURE:
<223> OTHER INFORMATION: Synthetic Primer

<400> SEQUENCE: 24
gtggtaggct cttggaaatg taatc                                       25

<210> SEQ ID NO 25
<211> LENGTH: 23
<212> TYPE: DNA
<213> ORGANISM: Artificial Sequence
<220> FEATURE:
<223> OTHER INFORMATION: Synthetic Primer

<400> SEQUENCE: 25
gaggagggct caggtaagag aga                                         23

<210> SEQ ID NO 26
<211> LENGTH: 18
<212> TYPE: DNA
<213> ORGANISM: Artificial Sequence
<220> FEATURE:
<223> OTHER INFORMATION: Synthetic Primer

<400> SEQUENCE: 26
tggcaacagc gaggacag                                               18

<210> SEQ ID NO 27
<211> LENGTH: 22
<212> TYPE: DNA
<213> ORGANISM: Artificial Sequence
<220> FEATURE:
<223> OTHER INFORMATION: Synthetic Primer

<400> SEQUENCE: 27
caaccatgca acttcgaaag aa                                          22

<210> SEQ ID NO 28
<211> LENGTH: 19
<212> TYPE: DNA
<213> ORGANISM: Artificial Sequence
<220> FEATURE:
<223> OTHER INFORMATION: Synthetic Primer

<400> SEQUENCE: 28
ccccacggga gcatacttg                                              19

<210> SEQ ID NO 29
<211> LENGTH: 22
<212> TYPE: DNA
<213> ORGANISM: Artificial Sequence
<220> FEATURE:
<223> OTHER INFORMATION: Synthetic Primer

<400> SEQUENCE: 29
cacagtacca ggcctcctca tt                                          22
```

<210> SEQ ID NO 30
<211> LENGTH: 29
<212> TYPE: DNA
<213> ORGANISM: Artificial Sequence
<220> FEATURE:
<223> OTHER INFORMATION: Synthetic Primer

<400> SEQUENCE: 30
tcactatctg agtggtcttt atgatgact                              29

<210> SEQ ID NO 31
<211> LENGTH: 20
<212> TYPE: DNA
<213> ORGANISM: Artificial Sequence
<220> FEATURE:
<223> OTHER INFORMATION: Synthetic Primer

<400> SEQUENCE: 31
cggagacacg ggtgatgatt                                        20

<210> SEQ ID NO 32
<211> LENGTH: 22
<212> TYPE: DNA
<213> ORGANISM: Artificial Sequence
<220> FEATURE:
<223> OTHER INFORMATION: Synthetic Primer

<400> SEQUENCE: 32
cagtcctttc acagccaatt cc                                     22

<210> SEQ ID NO 33
<211> LENGTH: 22
<212> TYPE: DNA
<213> ORGANISM: Artificial Sequence
<220> FEATURE:
<223> OTHER INFORMATION: Synthetic Primer

<400> SEQUENCE: 33
gtccatggga agaggacatc tt                                     22

<210> SEQ ID NO 34
<211> LENGTH: 25
<212> TYPE: DNA
<213> ORGANISM: Artificial Sequence
<220> FEATURE:
<223> OTHER INFORMATION: Synthetic Primer

<400> SEQUENCE: 34
gatcattatc tttcgctctc cattc                                  25

<210> SEQ ID NO 35
<211> LENGTH: 20
<212> TYPE: DNA
<213> ORGANISM: Artificial Sequence
<220> FEATURE:
<223> OTHER INFORMATION: Synthetic Primer

<400> SEQUENCE: 35
tgttcacaac gggcatgttt                                        20

<210> SEQ ID NO 36
<211> LENGTH: 25
<212> TYPE: DNA
<213> ORGANISM: Artificial Sequence
<220> FEATURE:

```
<223> OTHER INFORMATION: Synthetic Primer

<400> SEQUENCE: 36
ttgtgttttt gaacaggttc cttct                                              25
```

USE OF JUMONJI C DEMETHYLASE INHIBITORS FOR THE TREATMENT AND PREVENTION OF CHEMOTHERAPY RESISTANCE AND RADIORESISTANCE IN CANCER

CROSS REFERENCE TO RELATED APPLICATIONS

This application is a national phase application under 35 U.S.C. § 371 of International Application No. PCT/US2017/030132, filed Apr. 28, 2017 which claims priority to U.S. Provisional Application Ser. No. 62/329,670 filed Apr. 29, 2016, the contents of each are incorporated herein by reference in their entirety.

STATEMENT OF GOVERNMENT SUPPORT

This invention was made with government support under CA125269, CA070907, CA196539, CA016672, and CA142543 awarded by the National Institutes of Health, and W81XWH-07-1-0306 and W81XWH-07-1-0129 awarded by the United States Army Medical Research and Materiel Command. The government has certain rights in the invention.

BACKGROUND OF THE INVENTION

1. Field of the Invention

The present invention relates generally to the fields of biochemistry, cell biology, and oncology. More specifically, it concerns methods for the use of Jumonji C demethylase inhibitors for the radiosensitization of cancer cells and the treatment and prevention of chemotherapy resistance in cancer.

2. Description of Related Art

Lung cancer is the leading cause of cancer-related deaths in the U.S., accounting for 27% of all cancer deaths. Non-small cell lung cancer (NSCLC) accounts for 85% of all lung cancer cases, more than 50% of which are already locally advanced or metastatic at the time of diagnosis. Typically, platinum-based doublet chemotherapy is given as a standard treatment wherein carboplatin or cisplatin is given in combination with third generation cytotoxic agents, such as paclitaxel, docetaxel, vinorelbine, pemetrexed or gemcitabine. Early-stage patients can also be given platin-taxane chemotherapy to shrink tumors prior to surgical resection (neoadjuvant therapy). While these treatments in advanced and localized non-small cell lung cancer (NSCLC) provide some benefit, the majority of patient tumors relapse, becoming drug resistant. Traditional mechanisms of cancer drug resistance include increased drug efflux, reduced drug uptake, enhanced DNA repair, and drug metabolism. The overall five-year survival rate for NSCLC remains at only 21%. Recent studies have suggested that cancer drug-tolerance can be epigenetically driven.

Cancer relapse after chemotherapy poses a major obstacle for lung cancer treatment. In a retrospective study by Martin et al., 2002 that analyzed recurrence rates in early-stage NSCLC patients that had undergone pathologically verified complete resection following neoadjuvant chemotherapy, recurrence was reported in 68% of these patients, with 19% exhibiting recurrence at both locoregional and distant sites. Another study by Masserelli et al., 2003 in recurrent, advanced-stage IIIB or IV NSCLC patients who had received third- or fourth-line chemotherapy after two prior platinum-taxane chemotherapy regimens revealed that the response rate as well as disease control rate decreased significantly with each subsequent line of chemotherapy, suggesting development of drug resistance in these tumors. Further, d'Amato et al., 2007 reports the evaluation of 4571 fresh NSCLC tumor surgical biopsy specimens in an in vitro assay that revealed that about 70% of the tumors exhibited extreme or intermediate drug resistance to at least one drug in the standard carboplatin-paclitaxel or cisplatin-docetaxel combination. Thus, despite advances in targeted therapy for lung cancer, there is a large unmet clinical need to identify effective therapies for standard chemotherapy-resistant NSCLCs.

SUMMARY OF THE INVENTION

The current invention has identified methods for the treatment and prevention of chemotherapy resistance in cancer and sensitizing cancer cells to radiation through the administration of an agent that inhibits a JumonjiC (JmjC) polypeptide, also known as a JmjC demethylase inhibitor, wherein the JmjC polypeptide comprises a JmjC domain. Specifically, it has been found that the JumonjiC histone lysine demethylase family is upregulated during taxane-platin resistance. The finding is premised on the realization that progressively chemotherapy resistant cells develop increasing sensitivity to JmjC demethylase inhibitors. JmjC demethylase inhibitors are also capable of blocking effective DNA repair in cancer, thereby sensitizing cancer cells to radiation and robustly increasing the cytotoxic effects of radiation therapy. Without wishing to be bound by theory, it is believed that the current embodiments provide new therapeutic opportunities for treating cancer including the targeting of standard taxane-platin resistance in NSCLC and possibly preventing the emergence of drug-tolerant sub-populations and treating radioresistant cancers by sensitizing them with Jumonji inhibitors of the type herein described.

In some aspects, disclosed are methods for treating cancer in a subject in need thereof, the method comprising administering to the subject a therapeutically effective amount of an agent that inhibits a JmjC polypeptide, wherein the JmjC polypeptide comprises a JmjC domain, and wherein the cancer is resistant to a chemotherapy. In some embodiments, the agent that inhibits a JmjC polypeptide inhibits a catalytic JmjC domain. In some embodiments, the agent that inhibits a JmjC polypeptide is a PHD domain inhibitor or a protein-protein interaction inhibitor. In some embodiments, the agent that inhibits a JmjC polypeptide is a pan-JmjC demethylase inhibitor or an inhibitor of two or more JmjC enzymes. In some embodiments, the agent that inhibits a JmjC polypeptide targets two or more members of the Jumonji enzyme family. In some embodiments, the agent that inhibits a JmjC polypeptide targets a protein that comprises a JmjC domain. In some embodiments, the agent that inhibits a JmjC polypeptide is JIB-04, GSK-J4, SD-70, ML324, KDM5-C70, PBIT, KDOHP64a, KDOQZ5, IOX1, IOX2, KDOMA83, KDMOBP69, NSC636819, pyrido[3,4-d]pyrimidin-4(3H)-one derivatives, 3-amino-4-pyridine carboxylate derivatives, or analogs thereof. In some embodiments, the agent that inhibits a JmjC polypeptide is JIB-04. In some embodiments, the agent that inhibits a JmjC polypeptide is not a KDM1 or LSD1 inhibitor.

In some embodiments, the agent that inhibits a JmjC polypeptide is administered as a monotherapy. In some embodiments, the method further comprises administering one or more chemotherapeutic agents. In some embodiments, the one or more chemotherapeutics agents is chemotherapy, targeted therapy, epigenetic therapy, and/or immunotherapy. In some embodiments, the method further comprises administering radiation therapy and/or surgery. In some embodiments, the chemotherapy is one or more of a platinum agent, taxane, vinca alkaloid, anthracycline, antimitotic, anti-metabolite, DNA damaging agent, topoisomerase inhibitor, radiation, and/or anti-tumor antibiotic. In some embodiments, the chemotherapy is a taxane-platin combination therapy comprising paclitaxel-carboplatin or docetaxel-cisplatin doublet therapy. In some embodiments, the cancer is one or more of adrenal cancer, acute lymphoblastic leukemia, acute myelogenous leukemia, astrocytoma, basal cell carcinoma, bile duct cancer, bladder cancer, bone cancer, breast cancer, brain cancer, carcinoma, cardiac tumor, cervical cancer, childhood cancers, chronic lymphocytic leukemia, chronic myelogenous leukemia, colorectal cancer, embryonal tumor, epithelial cancer, esophageal cancer, gastrointestinal cancer, germ cell tumor, gallbladder cancer, gastric cancer, glioma, head and neck cancer, hematological malignancy, Hodgkin's lymphoma, non-Hodgkin's lymphoma, intestinal cancer, intraocular melanoma, kidney cancer, laryngeal cancer, leukemia, lung cancer, liver cancer, malignant peripheral nerve sheath tumor, melanoma, mesothelioma, nasopharyngeal carcinoma, neuroblastoma, neurofibroma, oral cancer, non-small cell lung cancer, osteosarcoma, ovarian cancer, pituitary tumor, prostate cancer, pancreatic cancer, retinoblastoma, rhabdomyosarcoma, sarcoma, small cell lung cancer, testicular cancer, throat cancer, thyroid cancer, transitional cell carcinoma, urogenital cancer, urothelial carcinoma, uterine cancer, vaginal cancer, or Wilms' tumor. In some embodiments, the lung cancer is non-small cell lung cancer (NSCLC).

In some embodiments, the agent that inhibits a JmjC polypeptide inhibits one or more of KDM2A, KDM2B, KDM3A, KDM3B, JMJD1C, KDM4A, KDM4B, KDM4C, KDM4D, KDM4E, KDM5A, KDM5B, KDM5C, KDM5D, KDM6A, KDM6B, KDM7A, PHF8, KDM8, JARID2, FBXL19, JMJD4, JMJD5, JMJD6, JMJD7, JMJD7-PLA2G4B, JMJD8, HIF1AN, HR, HSPBAP1, MINA, N066, PHF2, PLA2G4B, TYW5, and/or UTY. In some embodiments, the agent that inhibits a JmjC polypeptide inhibits KDM3A, KDM3B, and/or JMJD1C. In some embodiments, the administration targets chemoresistant tumors after the development of resistance. In some embodiments, the administration prevents the emergence of resistance in chemo-sensitive and/or untreated tumors.

In some aspects, disclosed are methods of increasing the efficacy of a cancer therapy in a subject in need thereof comprising administering to the subject a therapeutically effective amount of an agent that inhibits a JmjC polypeptide. In some embodiments, the cancer therapy is chemotherapy or radiation therapy. In some embodiments, the chemotherapy or radiation therapy treats a cancer that has become resistant and/or is intrinsically resistant to the cancer therapy. In some embodiments, the cancer is radiosensitized and/or chemosensitized. In some embodiments, the radiation therapy is x-rays and/or gamma rays. In some embodiments, the agent that inhibits a JmjC polypeptide is JIB-04, SD-70, ML324, KDM5-C70, PBIT, KDOHP64a, KDOQZ5, IOX1, IOX2, KDOMA83, KDMOBP69, NSC636819, pyrido[3,4-d]pyrimidin-4(3H)-one derivatives, 3-amino-4-pyridine carboxylate derivatives or analogs thereof. In some embodiments, the agent that inhibits a JmjC polypeptide targets a protein that comprises a JmjC domain. In some embodiments, the agent that inhibits a JmjC polypeptide is JIB-04. In some embodiments, the cancer is one or more of adrenal cancer, acute lymphoblastic leukemia, acute myelogenous leukemia, astrocytoma, basal cell carcinoma, bile duct cancer, bladder cancer, bone cancer, breast cancer, brain cancer, carcinoma, cardiac tumor, cervical cancer, childhood cancers, chronic lymphocytic leukemia, chronic myelogenous leukemia, colorectal cancer, embryonal tumor, epithelial cancer, esophageal cancer, gastrointestinal cancer, germ cell tumor, gallbladder cancer, gastric cancer, glioma, head and neck cancer, hematological malignancy, Hodgkin's lymphoma, non-Hodgkin's lymphoma, intestinal cancer, intraocular melanoma, kidney cancer, laryngeal cancer, leukemia, lung cancer, liver cancer, malignant peripheral nerve sheath tumor, melanoma, mesothelioma, nasopharyngeal carcinoma, neuroblastoma, neurofibroma, oral cancer, non-small cell lung cancer, osteosarcoma, ovarian cancer, pituitary tumor, prostate cancer, pancreatic cancer, retinoblastoma, rhabdomyosarcoma, sarcoma, small cell lung cancer, testicular cancer, throat cancer, thyroid cancer, transitional cell carcinoma, urogenital cancer, urothelial carcinoma, uterine cancer, vaginal cancer, or Wilms' tumor. In some embodiments, the lung cancer is non-small cell lung cancer (NSCLC), or prostate cancer, or osteosarcoma or any other cancer treated with radiation. In some embodiments, the agent that inhibits a JmjC polypeptide is a pan-JmjC demethylase inhibitor or an inhibitor of two or more JmjC enzymes. In some embodiments, the agent that inhibits a JmjC polypeptide inhibits one or more of KDM2A, KDM2B, KDM3A, KDM3B, JMJD1C, KDM4A, KDM4B, KDM4C, KDM4D, KDM4E, KDM5A, KDM5B, KDM5C, KDM5D, KDM6A, KDM6B, KDM7A, PHF8, KDM8, JARID2, FBXL19, JMJD4, JMJD5, JMJD6, JMJD7, JMJD7-PLA2G4B, JMJD8, HIF1AN, HR, HSPBAP1, MINA, N066, PHF2, PLA2G4B, TYW5, UTY, or any protein containing a JmjC domain. In some embodiments, the agent that inhibits a JmjC polypeptide affects H3K4, H3K9, and/or H3K36 methylation. In some embodiments, the affected H3K4, H3K9, and/or H3K36 methylation results in blocking or delaying DNA repair in cancer cells that increases the efficacy of radiation. In some embodiments, the administration comprises targeting chemoresistant tumors after the development of radioresistance. In some embodiments, the administration prevents the emergence of resistance in chemo-sensitive and/or radio-sensitive and/or untreated tumors In some embodiments, the administration decreases toxicities of radiation.

In one embodiment of the present invention, there is disclosed a method for treating cancer in a subject in need thereof, the method including administering to the subject a therapeutically effective amount of a JumonjiC Demethylase Inhibitor, wherein the cancer is resistant to a chemotherapy. In one aspect the JumonjiC Demethylase Inhibitor employed in the method can be administered as a monotherapy and the JumonjiC Demethylase Inhibitor can be JIB-04, GSK-J4, SD-70, ML324, KDM5-C70, PBIT, KDOHP64a, KDOQZ5, IOX1, IOX2, KDOMA83, KDMOBP69, NSC636819, pyrido[3,4-d]pyrimidin-4(3H)-one derivatives, 3-amino-4-pyridine carboxylate derivatives or any analogs of the aforementioned compounds or any inhibitor of Jumonji proteins that targets more than one member of the Jumonji enzyme family wherein a Jumonji enzyme is any protein that contains a JumonjiC (JmjC) domain. In another aspect the JumonjiC Demethylase Inhibitor can be administered with one or more chemotherapeutic agents. The one or more chemotherapeutics agents can be a standard of care chemotherapy and/or targeted therapy and/or epigenetic therapy and/or immunotherapy, any of the aforementioned administered with or without other forms of treatment including radiation therapy and/or surgery. In some instances the chemotherapy is one or more of a platinum agent, taxane, vinca alkaloid, anthracycline, anti-mitotic, anti-metabolite, DNA damaging agent, topoisomerase inhibitor, radiation, or anti-tumor antibiotic, and in other instances the chemotherapy is a taxane-platin combination therapy comprising paclitaxel-carboplatin or docetaxel-cisplatin doublet therapy. A significant feature of the method of the current invention is that the cancer can be one or more of adrenal cancer, acute lymphoblastic leukemia, acute myelogenous leukemia, astrocytoma, basal cell carcinoma, bile duct cancer, bladder cancer, bone cancer, breast cancer, brain cancer, carcinoma, cardiac tumor, cervical cancer, childhood cancers, chronic lymphocytic leukemia, chronic myelogenous leukemia, colorectal cancer, embryonal tumor, epithelial cancer, esophageal cancer, gastrointestinal cancer, germ cell tumor, gallbladder cancer, gastric cancer, glioma, head and neck cancer, hematological malignancy, Hodgkin's lymphoma, non-Hodgkin's lymphoma, intestinal cancer, intraocular melanoma, kidney cancer, laryngeal cancer, leukemia, lung cancer, liver cancer, malignant peripheral nerve sheath tumor, melanoma, mesothelioma, nasopharyngeal carcinoma, neuroblastoma, neurofibroma, oral cancer, non-small cell lung cancer, osteosarcoma, ovarian cancer, pituitary tumor, prostate cancer, pancreatic cancer, retinoblastoma, rhabdomyosarcoma, sarcoma, small cell lung cancer, testicular cancer, throat cancer, thyroid cancer, transitional cell carcinoma, urogenital cancer, urothelial carcinoma, uterine cancer, vaginal cancer, or Wilms' tumor. In some embodiments the cancer is lung cancer and the lung cancer is non-small cell lung cancer (NSCLC). Particularly the JumonjiC Demethylase Inhibitor is a pan-JumonjiC Demethylase Inhibitor or an inhibitor of more than one JumonjiC enzymes including one or more of KDM2A, KDM2B, KDM3A, KDM3B, JMJD1C, KDM4A, KDM4B, KDM4C, KDM4D, KDM4E, KDM5A, KDM5B, KDM5C, KDM5D, KDM6A, KDM6B, KDM7A, PHF8, KDM8, JARID2, FBXL19, JMJD4, JMJD5, JMJD6, JMJD7, JMJD7-PLA2G4B, JMJD8, HIF1AN, HR, HSPBAP1, MINA, N066, PHF2, PLA2G4B, TYW5, UTY, or any protein containing a JmjC domain. Specific features of this method of the current invention are that the JumonjiC Demethylase Inhibitor can inhibit KDM3A, and/or KDM3B, and/or JMJD1C; the administration targets chemoresistant tumors after the development of resistance; and the administration can prevent the emergence of resistance in chemo-sensitive and/or untreated tumors.

Also disclosed is a method of increasing the efficacy of a cancer therapy in a subject in need thereof comprising administering to the subject a therapeutically effective amount of a JumonjiC Demethylase Inhibitor. Specifically the cancer therapy employed in the method can be chemotherapy or radiation therapy and the chemotherapy or radiation therapy treats a cancer that has become resistant and/or is intrinsically resistant to the cancer therapy. In one aspect the cancer is radiosensitized and the radiation therapy can be x-rays and/or gamma rays. In another aspect the JumonjiC Demethylase Inhibitor is JIB-04, SD-70, ML324, KDM5-C70, PBIT, KDOHP64a, KDOQZ5, IOX1, IOX2, KDOMA83, KDMOBP69, NSC636819, pyrido[3,4-d]pyrimidin-4(3H)-one derivatives, 3-amino-4-pyridine carboxylate derivatives or any analogs of the aforementioned compounds or any inhibitor of Jumonji proteins that targets any member of the Jumonji enzyme family other than exclusively a H3K27me3 demethylase, wherein a Jumonji enzyme is any protein that contains a JumonjiC (JmjC) domain. Particularly the JumonjiC Demethylase Inhibitor is JIB-04. In some aspects of the method the cancer is one or more of adrenal cancer, acute lymphoblastic leukemia, acute myelogenous leukemia, astrocytoma, basal cell carcinoma, bile duct cancer, bladder cancer, bone cancer, breast cancer, brain cancer, carcinoma, cardiac tumor, cervical cancer, childhood cancers, chronic lymphocytic leukemia, chronic myelogenous leukemia, colorectal cancer, embryonal tumor, epithelial cancer, esophageal cancer, gastrointestinal cancer, germ cell tumor, gallbladder cancer, gastric cancer, glioma, head and neck cancer, hematological malignancy, Hodgkin's lymphoma, non-Hodgkin's lymphoma, intestinal cancer, intraocular melanoma, kidney cancer, laryngeal cancer, leukemia, lung cancer, liver cancer, malignant peripheral nerve sheath tumor, melanoma, mesothelioma, nasopharyngeal carcinoma, neuroblastoma, neurofibroma, oral cancer, non-small cell lung cancer, osteosarcoma, ovarian cancer, pituitary tumor, prostate cancer, pancreatic cancer, retinoblastoma, rhabdomyosarcoma, sarcoma, small cell lung cancer, testicular cancer, throat cancer, thyroid cancer, transitional cell carcinoma, urogenital cancer, urothelial carcinoma, uterine cancer, vaginal cancer, or Wilms' tumor. In some instances the lung cancer is non-small cell lung cancer (NSCLC), or prostate cancer, or osteosarcoma or any other cancer treated with radiation. In other instances the JumonjiC Demethylase Inhibitor is a pan-JumonjiC Demethylase Inhibitor or an inhibitor of more than one JumonjiC enzymes including one or more of KDM2A, KDM2B, KDM3A, KDM3B, JMJD1C, KDM4A, KDM4B, KDM4C, KDM4D, KDM4E, KDM5A, KDM5B, KDM5C, KDM5D, KDM6A, KDM6B, KDM7A, PHF8, KDM8, JARID2, FBXL19, JMJD4, JMJD5, JMJD6, JMJD7, JMJD7-PLA2G4B, JMJD8, HIF1AN, HR, HSPBAP1, MINA, N066, PHF2, PLA2G4B, TYW5, UTY or any protein containing a JmjC domain. In a particular aspect the JumonjiC Demethylase Inhibitor affects H3K4, H3K9 and/or H3K36 methylation and the affected H3K4, H3K9 and/or H3K36 methylation results in blocking or delaying DNA repair in cancer cells that increases the efficacy of radiation. Specific features of this method of the current invention are that the administration targets chemoresistant tumors after the development of radioresistance, prevents the emergence of resistance in chemo-sensitive and/or untreated radioresistant tumors, and decreases toxicities of radiation.

The following includes definitions of various terms and phrases used throughout this specification.

A "disease" is defined as a pathological condition of a body part, an organ, or a system resulting from any cause, such as infection, genetic defect, or environmental stress. A "health-related condition" is defined herein to refer to a condition of a body part, an organ, or a system that may not be pathological, but for which treatment is sought. Examples include conditions for which cosmetic therapy is sought, such as skin wrinkling, skin blemishes, and the like. The disease can be any disease, and non-limiting examples include hyperproliferative diseases such as cancer and pre-malignant lesions, wounds, and infections.

As used herein, the phrases "treating and/or preventing" or "treatment and/or prevention" includes the administration of the compositions, compounds or agents of the invention to prevent or delay the onset of the symptoms, complications, or biochemical indicia of a disease, alleviating or ameliorating the symptoms or arresting or inhibiting further development of the disease, condition, or disorder (e.g., cancer). "Treating and/or preventing" further refers to any indicia of success in the treatment or amelioration or prevention of the disease, condition, or disorder, including any objective or subjective parameter such as abatement; remission diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the phrase "treating and/or preventing" includes the administration of the therapeutic agents of the disclosure to prevent or delay, to alleviate, or to arrest or inhibit development of the symptoms or conditions associated with cell proliferation, cancer and metastasis and/or to lessen side effects associated with treatment toxicities.

A "therapeutically effective amount" of a substance/molecule may vary according to factors such as the disease state, age, sex, and weight of the individual, and the ability of the substance/molecule to elicit a desired response in the individual. A therapeutically effective amount is also one in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

By "reduce or inhibit" is meant the ability to cause an overall decrease of 20%, 30%, 40%, 50%, 60%, 70%, 75%, 80%, 80% 85%, 90%, 95%, or greater. Reduce or inhibit can refer to the symptoms of the disorder being treated, the presence or size of metastases, or the size of the primary tumor or the side effects of existing therapies.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention.

The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, the methods and systems of the present invention that "comprises," "has," "includes" or "contains" one or more elements possesses those one or more elements, but is not limited to possessing only those one or more elements. Likewise, an element of a method or system of the present invention that "comprises," "has," "includes" or "contains" one or more features possesses those one or more features, but is not limited to possessing only those one or more features.

Any method or system of the present invention can consist of or consist essentially of—rather than comprise/include/contain/have—any of the described elements and/or features and/or steps. Thus, in any of the claims, the term "consisting of" or "consisting essentially of" can be substituted for any of the open-ended linking verbs recited above, in order to change the scope of a given claim from what it would otherwise be using the open-ended linking verb.

Throughout this application, the term "about" is used to indicate that a value includes the standard deviation of error for the device and/or method being employed to determine the value.

The term "substantially" is defined as being largely but not necessarily wholly what is specified (and include wholly what is specified) as understood by one of ordinary skill in the art. In any disclosed embodiment, the term "substantially" may be substituted with "within [a percentage] of" what is specified, where the percentage includes 0.1, 1, 5, and 10 percent.

As used herein, in the specification, "a" or "an" may mean one or more, unless clearly indicated otherwise. As used herein, in the claim(s), when used in conjunction with the word "comprising," the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings illustrate by way of example and not limitation. For the sake of brevity and clarity, every feature of a given structure may not be labeled in every figure in which that structure appears. Identical reference numbers do not necessarily indicate an identical structure. Rather, the same reference number may be used to indicate a similar feature or a feature with similar functionality, as may non-identical reference numbers.

FIGS. 1A, 1C: Dose response curves for NSCLC cell lines NCI-H1299 and NCI-H1355 after long-term treatment with drug on/drug off cycles of paclitaxel+carboplatin chemotherapy. P: Parental cell line, T[n]: Resistant variant generated after 'n' cycles of doublet chemotherapy. Drugs were tested in the clinically relevant 2:3 wt/wt ratio of paclitaxel:carboplatin (see Methods for details). Values on the X-axis indicate nM paclitaxel concentration in the drug combination. Each data-point represents mean+SD of 8 replicates. FIGS. 1B, 1D: IC50 plots for H1299 and H1355 resistant cell line variants. IC50 values represent nM paclitaxel concentration in the 2:3 drug combination. Data represents IC50 mean+SD of >4 replicate assays (with 8 drug doses×8 replicates within each assay). P values are from post-test for linear trend following one-way ANOVA. FIGS. 1E, 1G: Resistance was validated in liquid colony formation assays. Representative plate images are shown. Serial 2-fold drug dilutions starting from 400 nM were tested. Drug values indicate nM concentration of paclitaxel in the 2:3 wt/wt paclitaxel:carboplatin doublet.

FIGS. 1F, 1H: Dose response curves were generated by counting stained colonies from colony formation assays. For plotting dose response of parental cell lines, additional plates were treated with lower doses of paclitaxel+carboplatin (serial 2-fold dilutions from 40 nM). Error bars represent mean+SEM.

FIGS. 2A-2B: H1299 Parental and H1299 T18 tumor bearing mice were randomized (n=8 mice per treatment group) to receive vehicle treatment or docetaxel+cisplatin doublet chemotherapy given in clinically relevant 1:1 wt/wt ratio. Treatment was given once a week, for 3 weeks i.e. 3 cycles. Tumor volumes were measured after each treatment cycle (C1, C2, C3). Error bars represent mean+SEM. Vehicle and treatment groups were compared using two-way ANOVA followed by Sidak's multiple comparison tests. H1299 Parental xenografts, two-way ANOVA: P=0.002, Sidak's test at C3: **P<0.0001; H1299 T18 xenografts, two-way ANOVA: P value not significant (n.s.). FIG. 2C: H1299 T18 resistant cells showed multi-drug resistance phenotype. Red and green dotted lines indicate 10-fold cut-offs for resistance and sensitivity respectively. FIG. 2D: Paclitaxel+carboplatin resistant cell line variants showed cross-resistance to docetaxel, doxorubicin, vinorelbine and depsipeptide. Each data-point represents mean+SD from 8 replicates per drug dose. FIGS. 2E, 2G: Dose response curves illustrating partial reversal in chemo-resistance upon drug-free culturing for >4 months. Suffix 'R' denotes resistant cells and 'S' indicates partially re-sensitized cells. Each assay includes 8 replicates per drug dose. Error bars represent mean+SD. X-axis shows paclitaxel dose in the 2:3 paclitaxel:carboplatin combination. FIGS. 2F, 2H: IC50 values from MTS assays (n≥3) depicting reversal of resistance. Error bars represent mean+SEM. P values are from two-tailed unpaired t-test; *P<0.05, P<0.01, *P<0.001, **P<0.0001. See also FIGS. 10-11**.

FIGS. 3A-3B: H1299 and H1355 resistant variants showed slower cell growth rate in vitro. Error bars represent mean±SEM. Statistical significance was determined by two-way ANOVA. FIGS. 3C-3D: Xenografts of H1299 and H1355 resistant cells showed slower tumor growth in vivo compared to parental xenografts. Data represents mean±SEM. Differences in tumor growth rate were tested by two-way ANOVA. FIG. 3E: H1355 parental cells were mainly epithelial in appearance whereas long-term drug treated resistant cells (H1355 T8) exhibited mesenchymal morphology, indicative of EMT. Scale bar, 20 μM. FIG. 3F: Cell line variants showed partial reversal in resistance upon drug-free culturing for >4 months. Suffix 'S' denotes partially re-sensitized cells. See FIG. 12 for data supplemental to panel FIG. 3E.

FIG. 4A: Linear regression model was fitted on microarray data of H1299 and H1355 cell line series using log transformed IC50 values to identify genes that were progressively up/down-regulated with increasing drug resistance. Parental cell lines (P) and four resistant variants per cell line were analyzed. Differentially expressed genes are represented in the volcano plots (red: up-regulated; green: down-regulated). FDR 0.1 FIG. 4B: Microarray hits from the two resistant cell line series were compared to identify common up- and down-regulated genes. P values are from hypergeometric tests. FIG. 4C: Differential gene expression analysis was performed on xenograft microarray data (H1299 T18 resistant vs H1299 Parental) using student's t-test. FDR 0.1 FIG. 4D: Gene lists obtained from cell line and xenograft microarray analyses were overlapped to identify common genes (14 up-regulated, 21 down-regulated). P values are from hypergeometric tests. FIG. 4E: Heat map representation of the expression pattern of 35-gene resistance signature in resistant cell lines and xenografts. FIG. 4F: Using mRNA expression of 35 genes, unsupervised hierarchical clustering of neoadjuvant treated NSCLC patients (n=65, mainly taxane+platin treated) was found to separate the patients into two major groups. FIG. 4G: Kaplan-Meier survival analysis of the two groups of neoadjuvant treated NSCLC patients revealed significant differences in cancer recurrence-free survival (P=0.001, Hazard Ratio=2.78, 95% CI, 1.46-5.29). Survival P value was adjusted for clinical covariates. FIG. 4H: Cox multivariate regression was performed to identify individual contributions of the 35 genes to poor recurrence-free survival outcome. X-axis depicts hazard ratios i.e. exp (regression coefficient) and Y-axis represents −log (P values) for the 14 up-regulated genes. KDM3B showed the largest hazard risk for poor recurrence-free patient survival (Hazard ratio=10.28, P=0.025).

FIG. 5A: Group 2 of neoadjuvant treated patients (poor recurrence-free survival) showed higher KDM3B IHC scores compared to Group 1 patients. Representative images of KDM3B IHC and corresponding tumor H&E staining are shown. Scale bar=200 am. FIG. 5B: Chemotherapy-treated patient tumors showed higher mRNA expression scores of KDM3A and KDM4A, compared to chemo-naïve tumors. Y-axis depicts Log 2 normalized expression scores. The line in the middle of the boxes indicates median value and whiskers denote the 10th and 90th percentiles. P values are adjusted after multivariate analysis of clinical variables; *P<0.05, **P<0.0001. FIG. 5C: Paclitaxel+carboplatin resistant H1299 T18 cell line showed increased mRNA expression of several histone lysine demethylases (KDMs) compared to H1299 Parental, as detected by qRT-PCR. Error bars represent mean+SEM. Two-way ANOVA, *P<0.001. FIG. 5D: Isogenic H1299 resistant cells showed progressive increases in KDM expression. Error bars indicate mean+SEM. P values are from one-way ANOVA post-test for linear trend, *P<0.05, P<0.01, **P<0.0001. FIG. 5E: Global changes in histone lysine methylation in H1299 Parental vs. H1299 T18 cells were measured by histone PTM mass spectrometry. Y-axis denotes the % of the stated histone peptides (left, H3: 9-17; right, H3.3: 27-40) that showed K9 or K27 methylation respectively. Left panel shows reduced H3K9me1 and a subsequent increase in H3K9me0 in H1299 T18 cells. Error bars indicate mean+SEM, n=3. Right panel illustrates decreased K27me3/me2/me1 levels and a corresponding increase in K27me0 on histone H3.3 in H1299 T18. Error bars indicate mean+SEM, n=2. P values are from Fisher's LSD test post two-way ANOVA, *P<0.1, ***P<0.001. FIG. 5F: H3K27me3 ChIP-seq enrichment plots for up- and down-regulated genes identified by RNA-seq (FDR 0.05) in H1299 T18 vs H1299 Parental cells. Average H3K27me3 ChIP read depth in the gene body regions and 2 kb 5' and 3' to the gene body regions was subtracted from respective input read depth and plotted. X-axis represents the genomic regions from 5' to 3' and the Y-axis represents read depth. Left panel shows an overall decrease in H3K27me3 across genes bodies of up-regulated genes, whereas right panel depicts increased H3K27me3 specifically at the TSS of genes down-regulated in T18. FIG. 5G: H3K4me3 average distribution plots for differentially expressed genes in H1299 T18 vs H1299 Parental cells, showing increased H3K4me3 around the TSS of genes up-regulated in H1299 T18 (left panel) and a reduction in H3K4me3 at the TSS of down-regulated genes (right panel). TSS, transcription start site; TES, transcription end site. See also FIG. 32.

FIGS. 6A-6B: H1299 T18 cells showed hypersensitivity to JIB-04 active 'E' isomer (FIG. 6A) as well as GSK-J4 (FIG. 6B), compared to H1299 Parental. There was no loss of cell viability with the respective inactive drug isomers (JIB-04 'Z' isomer and GSK-J5). Each data point represents mean+ SD from 8 replicates per drug dose. FIGS. 6C-6D: IC50 plots for H1299 resistant series showing increasing sensitivity to JIB-04 and GSK-J4 with increasing resistance to standard chemotherapy. Data represents mean+SD. Statistical significance was tested by one-way ANOVA, followed by Dunnett's multiple comparisons with H1299 Parental, P<0.01, *P<0.001. P values listed on graphs are from post-test for linear trend. FIGS. 6E-6F: H1355 T16 resistant variant was hypersensitized to JIB-04 active 'E' isomer (FIG. 6E) and GSK-J4 (FIG. 6F), compared to H1355 Parental cell line. There was no loss of cell viability with JIB-04 'Z' isomer and GSK-J5. Each data-point represents mean+SD from 8 replicates per drug dose. FIG. 6G: All tested NSCLC resistant variants (H1299 T18, H1355 T16, HCC4017 T5 and H1693 T8) were more sensitive to JIB-04 than respective parental cell lines. Data represents mean+ SEM. Two-way ANOVA, P<0.01. FIG. 6H: Log 10 IC50 values for standard, targeted and epigenetic drugs for H1299 T18 chemoresistant vs H1299 Parental cells. Epigenetic drugs (blue dots) include inhibitors of KDM, LSD1, HMT, HDAC, HAT, DNMT and BRD. Red dotted line denotes the 10-fold cut-off for cross-resistance and green dotted line is the 10-fold cut-off for sensitization. See FIG. 14 and Table 8.

FIGS. 7A-7B: GSK-J4 treatment (100 mg/kg, every day, 10 days) caused a significant reduction in final tumor burden of H1299 T18 xenografts (FIG. 7B), but an insignificant response in H1299 Parental xenografts (FIG. 7A). Y-axis depicts % tumor volumes normalized to average vehicle tumor volume at the end of treatment. Data represent mean+ SEM, n=5 mice per group. P values for tumor volume growth are from two-way ANOVA, ns=not significant, **P<0.0001. Tumor weights (FIG. 7B, right) were compared using two-tailed unpaired t-test, P=0.007. FIGS. 7C-7D: At all tested doses, JIB-04 significantly reduced tumor burden and caused a greater percent reduction in H1299 T18 tumor volumes when compared to H1299 Parental tumors. Data represent mean+SEM, n=6-8 mice per group. Y-axis depicts % tumor volumes normalized to average vehicle tumor volume on Day 14. Exponential growth curves were fitted using non-linear regression. Drug response was compared using two-way ANOVA. 5 mg/kg vs. vehicle group, H1299 Parental: P=0.001 and H1299 T18: **P<0.0001. FIG. 7E: JIB-04 treatment slowed tumor growth and increased doubling time of treated H1299 T18 tumors by 69%, with minimal effect on H1299 Parental tumors (<25% change). Doubling times were derived from non-linear regression/exponential growth curves in (FIGS. 7C-7D). FIG. 7F: Tumor lysates from H1299 T18 xenografts showed higher histone H3K4/K9/K27me3 demethylase activity compared to lysates from H1299 Parental (P) tumors. GSK-J4 treated H1299 T18 xenografts showed significant inhibition of H3K27me3 demethylase activity (right panel), with no significant change in H3K4me3 (left) or H3K9me3 (middle) demethylase activity. P values are from Fisher's LSD test post one-way ANOVA. *P<0.1, P<0.01, *P<0.001. FIG. 7G: JIB-04 treated H1299 T18 xenografts showed significant reduction in H3K4me3, H3K9me3 as well as H3K27me3 demethylase activity. P values represent two-tailed unpaired t-tests, *P<0.05. FIG. 7H: JIB-04 and GSK-J4 treated H1355 T16 xenografts showed significant tumor shrinkage (right panel), whereas drug treated H1355 Parental xenografts continued to grow in volume (left). Y-axis depicts % change in tumor volumes relative to the treatment start volume (~120 mm3). P values are from two-way ANOVA, *P<0.05, P<0.01, **P<0.0001. See also FIG. 35.

FIGS. 8A-8B: Combination of JIB-04 (FIG. 8A) or GSK-J4 (FIG. 8B) with standard paclitaxel+ carboplatin chemotherapy resulted in synergistic inhibition of colony formation from H1299 T18 chemo-resistant cells. Error bars on graphs represent mean+SD from duplicate assays. P values are from two-tailed unpaired t-tests, *P<0.1, **P<0.01. Response was greater than additive, indicated by positive ΔBliss. FIG. 8C: Sub-lethal doses of JmjC KDM inhibitor GSK-J4 (but not other epigenetic inhibitors) prevented the emergence of paclitaxel+carboplatin drug-tolerant colonies from chemo-sensitive H1299 Parental cell line. Representative images from replicate assays (n=3) are shown. 10K cells were seeded per well at the start of each assay and plates were incubated until the 'no drug' well became confluent (10-14 days for H1299). Sub-lethal doses used for each epigenetic compound were pre-determined in colony formation assays and are listed below the respective wells. Doses were restricted to ≤10 μM (highest used for NU9056). FIG. 8D: GSK-J4 also blocked the emergence of paclitaxel+carboplatin drug-tolerant colonies from other chemo-sensitive, parental NSCLC cell lines: H1355, HCC4017 and H1693. To account for slower colony formation rate of these cell lines (compared to H1299), 20K cells were seeded per well and assay was continued until the 'no drug' well became confluent (3-5 weeks). Sub-lethal doses of GSK-J4 and paclitaxel+carboplatin surviving doses for each cell line are listed above or next to the respective wells. FIG. 8E: Combination of JIB-04 or GSK-J4 with standard paclitaxel+carboplatin chemotherapy resulted in significantly greater tumor growth inhibition in H1299 Parental chemo-sensitive xenografts. Tumor volumes during the course of treatment are shown in the top panel and tumor weights at sacrifice are represented in bottom graphs. Statistical tests on tumor volumes represent comparison of each treatment group with the Vehicle group by two-way ANOVA; n.s.=not significant, *P<0.05, P<0.01, **P<0.0001. ΔBliss for (Pac+Carb+JIB-04) combination=+13.8% and ΔBliss for (Pac+Carb+GSK-J4)=+13.9%, both values indicating that there was synergy. P values for tumor weight comparisons are from two-tailed unpaired t-tests, *P<0.1, P<0.01, *P<0.001. See also FIGS. 15-16.

FIG. 9A: H1355 Parental and isogenic H1355 T16 cells were screened for differential response to several standard and targeted therapies. Red and green dotted lines indicate 10-fold cut-offs for resistance and sensitivity respectively. FIGS. 9B-9E: H1355 T16 cell line was cross-resistant to docetaxel, doxorubicin, vinorelbine and depsipeptide which are known substrates of MDR1 transporter. Error bars represent mean±SD.

FIGS. 10A-10B: H1299 and H1355 resistant cell line series showed increase in ABCB1 mRNA transcripts with increasing treatment cycles. Data represents mean+SD. Statistical significance was tested by one-way ANOVA, followed by Dunnett's multiple comparisons test of each resistant variant with the parental cell line (indicated by asterisks). P values on graphs denote significance from post-test for linear trend. FIGS. 10C-10D: H1299 T18 and H1355 T16 showed enrichment in % MDR+ cells (FACS). FIG. 10E: H1299 T18 and H1355 T16 resistant cell lines exhibited decreased intracellular accumulation of tritiated docetaxel compared to parental cells. Data represent mean+SEM. Two-way ANOVA, P<0.0001 FIG. 10F: siRNA knockdown of ABCB1 (3 individual siRNAs: s2, s4, s5) in H1299 T18 could only partially reverse resistance to paclitaxel+carboplatin. Data represents mean+SD. Knockdown was validated by decrease in ABCB1 mRNA (see qPCR data for s4 siRNA). FIGS. 10G-10H: Drug response to paclitaxel+carboplatin was tested in the presence of non-specific MDR inhibitor verapamil (V, 5 μM) or MDR1/Pgp selective inhibitor PGP4008 (10 μM). There was partial shift in drug response curves. Each data-point represents mean+SD of 8 replicates.

FIGS. 11A-11B: H1693 T8 and HCC4017 T5 cell line variants were established by long-term treatment of parental cell lines with 8 and 5 cycles respectively of paclitaxel+carboplatin (2:3 wt/wt) doublet. Development of resistance was tested by MTS assays. Values in dose response plots indicate paclitaxel concentration in the doublet. Each assay was performed with 8 replicates per drug dose. Data represents mean+SD. FIGS. 11C-11D: Increase in drug resistance was validated by colony formation. Error bars indicate mean+SEM. P values are from two-way ANOVA. FIGS. 11E-11F: H1693 T8 showed enrichment in % MDR+ cell subpopulation whereas HCC4017 T5 cells did not show any increase in % MDR1+ cells by flow cytometry. FIG. 11G-11H: There was significant increase in ABCB1 mRNA expression in H1693 T8 compared to H1693 Parental, but minimal changes in ABCB1 transcripts in HCC4017 T5 resistant cells (qRT-PCR and microarray). Error bars in qRT-PCR data represent mean+SD. Heat map denotes expression from two ABCB1 microarray probes and two biological replicates per cell line.

FIGS. 12A-12B: Long-term drug treated H1355 T16 and H1299 T18 resistant cells showed dramatic decreases in % EpCAM+ cells. Appropriate isotype controls were used for gating cell populations. This was also observed on mRNA level (microarray analysis, data not shown). FIG. 12C: HCC4017 T5 showed a decrease in percentage of $EpCAM^{High}$ sub-population (quantified in histograms to the right). Also note the overall shift in histogram to decreased fluorescence intensity in HCC4017 T5.

FIG. 13A: High KDM3A, KDM4A and KDM6B mRNA expression correlated with poor cancer-free survival in NSCLC patient tumor dataset (275 tumors). High/Low groups were separated by median log expression value. FIGS. 13B-13C: H1693 T8 and HCC5017 T5 resistant variants which were ~3-fold resistant to paclitaxel+carboplatin (see Figure S3) were ~3-fold sensitized to the JmjC KDM inhibitor JIB-04, compared to parental cell lines. Drug response was specific to the epigenetically active E isomer. No loss in cell viability was seen with inactive Z isomer.

FIGS. 15A-15B: H1299 T18 cells showed ~3-times greater gene expression changes (total 1469 probes) after 24 h treatment with 0.2 μM JIB-04, compared to H1299 Parental cells (519 probes). Top up-regulated gene in H1299 T18 showed ~16-fold expression difference. FIGS. 15C-15D: H1299 T18 cells showed ~3-times more drug-induced gene expression changes (total 710 probes) after 24 h treatment with 1 μM GSK-J4, compared to H1299 Parental cells (224 probes). Top up-regulated gene in H1299 T18 showed ~25-fold expression difference. For FIGS. 15A-16D, red dots depict up-regulated genes and green dots represent down-regulated genes. All fold changes ≥1.5, t-test P values ≤0.05.

FIG. 16A: Heat maps illustrate subset of genes altered by JIB-04 or GSK-J4 treatment that also represent "reversal" of expression changes that were acquired upon development of taxane-platin resistance in H1299 T18 vs H1299 Parental cells. Vertical lanes depict a total of 6 samples per heat map (2 biological replicates per treatment condition). About 195 Illumina probes (187 genes) were reversed in expression by 0.2 μM JIB-04 treatment and 110 Illumina probes (108 genes) showed reversed expression after 1 μM GSK-J4 treatment of H1299 T18 cells. Fold changes ≥1.5, t-test P values ≤0.05. Top reversed up-regulated (YPEL2) and top reversed down-regulated (LEAP2) genes by JIB-04 showed ~16-fold (up) and ~5-fold (down) changes respectively. Top reversed up-regulated (BNIP3) and top reversed down-regulated (TAF9B) genes by GSK-J4 showed ~10-fold (up) and ~3-fold (down) changes respectively. See Table S7 for complete lists of reversed genes. FIG. 16B: Select genes from microarray analysis in (FIG. 16A), whose expression was reversed by both JIB-04 and GSK-J4 were validated by qRT-PCR. 18S rRNA was used as the endogenous control for normalization.

FIG. 17A: Gene set enrichment analysis (GSEA) of differentially expressed gene lists from microarray against MSigDB curated gene sets revealed that several of the transcriptional programs that were depleted in H1299 T18 resistant vs H1299 Parental cells were reversed/enriched by 24 h treatment with JIB-04 (0.2 μM) or GSK-J4 (1 μM). P values signify overlap by hypergeometric tests. Two of the 38 overlapping gene sets are shown. Left: Genes with H3K4me3 and H3K27me3 (Meissner et al, high-CpG-density promoters in brain, M1941), Right: Genes up-regulated in apoptotic tissues (Martoriati et al, MDM4 knockout in neuroepithelium, M5681). NES: Normalized Enrichment Score; P values under GSEA plots are nominal p-values; FDR: False Discovery Rate. FIG. 17B: ChIP-seq analysis confirmed loss of bivalent genes in H1299 T18 vs. Parental cells. Genes were classified as bivalent if both H3K4me3 signal and H3K27me3 signal were ≥4-fold over input in the region+/−500 bp around TSS. Legend for bar graph: Common subset shown in grey: Genes whose bivalency was maintained in T18 (n=201); Exclusive for H1299 T18, black in second bar=Genes that gained bivalency in T18 (n=210); Exclusive for H1299 P, black in first bar: Genes that lost their bivalency in T18 (n=551). Pie chart depicts the status of all 752 bivalent genes from H1299 P after resistance development in H1299 T18, and classifies them based on whether bivalency was lost due to loss of H3K4me3 (green) or H3K27me3 (pink) or both marks (yellow). FIG. 17C: Genes in each of the bivalency lost categories depicted in the pie chart (FIG. 17B) were probed for their regain status (at least a 1.5-fold increase) in GSK-J4 and JIB-04 treated H1299 T18 cells. Left: H3K27me3 lost and re-gained, Middle: H3K4me3 lost and regained, Right: Both marks lost and either one or both regained. FIG. 17D: Genes from the Martoriati et al apoptotic gene set identified through GSEA of microarray data (FIG. 17A) were confirmed to be upregulated by GSK-J4 in our RNA-seq dataset. Error bars indicate mean+SEM from biological duplicates. Significance was tested using the powerful False Discovery Rate (FDR, q) approach of two-stage linear step-up procedure of Benjamini, Krieger and Yekutieli; *q<0.05, q<0.01, *q<0.001, ****q<0.0001. FIG. 17E: ChIP-seq traces for the pro-apoptotic, up-regulated gene DDIT4, showing increased H3K4me3 (blue highlight) in GSK-J4 vs DMSO treated H1299 T18 cells. FIG. 17F: ChIP-seq traces for BNIP3 up-regulated gene, showing broader H3K4me3 enrichment in GSK-J4 treated vs DMSO treated H1299 T18 cells. GSK-J4: 1 μM, 24 h for both FIGS. 17E-17F. See also FIGS. 15-16, 20.

FIG. 18A: Heat map representing all differentially expressed KDM transcripts in H1299 T18 vs H1299 Parental xenograft tumors. N=3 tumors per group, P values are from unpaired t-tests. FIG. 18B: H1355 T16 chemoresistant cells show increased expression of mainly KDM3B, KDM6A and KDM6B, compared to H1355 Parental cells by qRT-PCR. Cyclophilin B was used as endogenous control. FIG. 18C: Analysis of combinatorial histone PTMs by mass spectrometry revealed that both H1299 T18 and H1355 t16 chemoresistant cells showed decreased H3K9me1 K14ac1 and a corresponding increase in % of H3K9/K14 unmodified (me0/ac0) peptide. Data represents 3 biological replicates per group. P values are from two-tailed unpaired t-tests. FIG. 18D: H3K27me3 average distribution across all transcribed regions of the genome by ChIP-seq, showing an overall decrease in H3K27me3 enrichment in H1299 T18 compared to H1299 Parental cells. FIG. 18E: H1299 T18 cells did not show any decrease in average H3K4me3 ChIP-seq distribution across transcribed regions of the genome, when compared with H1299 Parental cells. For both FIGS. 18D-18E, average H3K27me3 or H3K4me3 ChIP read depth in the gene body regions and 2 kb 5' and 3' to the gene body regions was subtracted from respective input read depth and plotted. X-axis represents the genomic regions from 5' to 3' and the Y-axis represents read depth. TSS, transcription start site; TES, transcription end site.

FIGS. 19A-19B: HCC5017 T5 and H1693 T8 cells which were ~3-fold resistant to paclitaxel+carboplatin (see FIG. 11) showed ~3-fold increased sensitivity to the pan-JmjC KDM inhibitor JIB-04, compared to corresponding parental cell lines. 'E' indicates JIB-04 active isomer, 'Z' is the inactive isomer. Each data point represents mean+SD of 8 replicates. JIB-04 IC50 values from multiple experiments are shown in FIG. 5G of the manuscript. FIG. 19C: GSK-J4 IC50 values from multiple experiments, showing that hypersensitization to this KDM6 inhibitor was only seen in H1299 T18 and H1355 T16 resistant variants, and not in HCC4017 T5 or H1693 T8 resistant variants. FIG. 19D: HCC4017 T5 showed up-regulation of other KDMs (not KDM6A/6B), when compared to HCC4017 Parental cells by qRT-PCR. FIG. 19E: H1693 T8 showed up-regulation of other KDMs (not KDM6A/6B), when compared to H1693 Parental cells by qRT-PCR. Cyclophilin B was used as the endogenous control for qPCR normalization in both FIGS. 19D-19E panels.

FIG. 20A: qRT-PCR revealed that several pro-apoptotic/anti-proliferative genes were up-regulated and proliferative/oncogenic genes were downregulated upon short-term 24 h treatment of H1299 T18 cells with JIB-04 (0.2 [M]) or GSK-J4 (1 [M]). 18S rRNA was used as the endogenous control for normalization. FIG. 20B: ABCB]/MDR1 mRNA expression showed minimal change (only ~10-20% decrease) in H1299 T18 cells treated with high dose JIB-04 (10×-20×IC50 as determined by 96 h MTS assays) over a short period of time (24-48 h treatment). FIG. 20C: ABCB1/MDR1 mRNA expression did not change much (only ~10-20% decrease) in H1299 T18 cells treated with low dose JIB-04 (1×IC50 as determined by 96 h MTS assays) over a longer period of time (1 wk treatment). P: H1299 Parental cells, T18: H1299 T18 cells, E: Active JIB-04 isomer, Z: Inactive isomer. FIG. 20D: MDR1 protein levels in JmjC inhibitor-treated (200 nM JIB-04, 48 h) H1299 T18 and H1355 T16 cells remained at much higher levels than the parental cell lines. FIG. 20E: H3K4me3 (pink) and H3K27me3 (blue) enrichment at the MDR1 locus in H1299 Parental, H1299 T18, GSK-J4 treated T18 and JIB-04 treated T18 cells. Although there was a decrease in H3K27me3 and increase in H3K4me3 at ABCB1 locus in H1299 T18 vs H1299 Parental cells, these histone marks did not change after 24 h JmjC inhibitor treatment of H1299 T18 cells. FIG. 20F: ABCB1/MDR1 locus was found to be genetically amplified in long-term paclitaxel+carboplatin treated H1299.

FIG. 21A: Body weights of mice bearing H1299 Parental or H1299 T18 xenograft tumors before and after JmjC inhibitor therapy. GSK-J4: 100 mg/kg i.p., for 10 consecutive days. JIB-04: 50 mg/kg, oral gavage, 3× per week, for 2 weeks. FIG. 21B: Body weights of mice bearing H1355 Parental or H1355 T16 xenograft tumors measured over the entire course of long-term JmjC inhibitor treatment. GSK-J4: 100 mg/kg i.p., 5× per week, for 4 weeks. JIB-04: 50 mg/kg, oral gavage, 3× per week, for 4 weeks. FIG. 21C: JIB-04 treatment caused reduction in % Ki67+ cells in H1299 T18 tumors in vivo, suggesting reduction in cell proliferation. Representative IHC images are shown. Scale bar: 100 µm. FIG. 21D: GSK-J4 treatment increased % γH2AX+ cells in H1299 T18 tumors in vivo, indicating increased DNA damage. Representative IHC images are shown. Scale bar: 50 µm. For both FIGS. 21C-21D: Percent positivity in the entire stained section per tumor was quantified via Aperio Image toolbox software. Data represents mean+SEM of 3 tumors per group. FIG. 21E: JIB-04 and GSK-J4 treated H1299 T18 tumors exhibited focally increased cleaved caspase 3 staining (apoptotic marker) in some tumor regions. Representative IHC images are shown.

FIG. 22A: JIB-04 $IC_{50}$ determination by clonogenic survival in H1299 and A549 cell lines. Tumor cell colonies were grown in the presence of increasing doses of JIB-04 active E-isomer (0-100 nM) or Inactive isomer of JIB-04 (Z) for 10 days. At the end of the assay, medium was aspirated and cells were fixed and stained with crystal violet. Colonies with more than 50 cells were counted. Single experiment done using duplicates for A549, H1299. FIG. 22B: Clonogenic survival of H1299 or A549 cells treated with 16 nM or 25 nM respectively of JIB-04 and then irradiated as indicated. Cells treated with DMSO or Z isomer were used as control. Graph represents two experiments done in triplicates. Error bars represent SD. FIG. 22C: JIB-04 SF2 (survival fraction of cells irradiated with 2 gy) and DER25 (dose of enhancement response 25, dose required to reduce the survival fraction to 25% divided by dose required to reduce the survival fraction to 25% in the presence of JIB-04) values for a panel of a panel of radioresistant and radiosensitive NSCLC cells treated with JIB-04. The SF2 and DER25 values were calculated using a linear quadratic and single hit multi-target model. FIG. 22D: Subcutaneous tumors generated from H1299 cells were allowed to reach a volume of 200 mm$^3$ following mice were treated every other day with vehicle, JIB-04 (50 mg/kg), IR, or JIB-04 with IR (2 Gy, given 4 hours after drug administration) for a total of 12 doses (shaded area). Tumor growth was monitored until tumors reached 2000 mm$^3$. DEF1000=(Days to 1000 mm$^3$ for JIB-04+IR)–(Days to 1000 mm$^3$ for JIB-04 alone)/(Days to 1000 mm$^3$ for IR alone)–(Days to 1000 mm$^3$ for Vehicle). Error bars represent S.E.M. P<0.0001 (IR vs. IR+JIB-04).

FIG. 24A: GSK-4 $IC_{50}$ determination by clonogenic survival in H1299 cell line. Tumor cell colonies were grown in the presence of GSK-J4 (0-1000 nM) for 10-14 days. At the end of the assay, medium was aspirated and cells were fixed, stained with crystal violet and colonies with more than 50 cells counted. Graph represents two experiments done by triplicates. Errors bars represent SD. FIG. 24B: Clonogenic survival of H1299 cells treated with 175 nM of GSK-J4 and then irradiated as indicated. Cells treated with DMSO or inactive GSK-J4 isomer (GSK-J5) were used as control. Graph represents two experiments done by triplicates. Error bars represent SD.

FIG. 25A: Schematic of JIB-04 and radiation for NSCLCS treated with concurrent-treatment (left panel) or post-treatment (right panel). For concurrent treatment cells were seeded, 4 h later JIB-04 was added incubated for another 4 h and then irradiated. For post-treatment, cells were seeded, 4 h later irradiated incubated for 4 h and then JIB-04 added. FIG. 25B: Clonogenic survival of H1299 or A549 cells concurrent or post-treated with 16 nM or 25 nM respectively of JIB-04 and irradiated as indicated. Cells treated with DMSO were used as control. Single experiment done by triplicates. Error bars represent SD.

FIGS. 26A-26C. JIB-04 affects DNA Double Strand Break (DBS) repair kinetics. DNA DSB repair kinetics in A549 (FIG. 26A) and H1299 (FIG. 26B) cells. Cells were incubated with (black bar) or without (white bar) JIB-04 for 4 h (25 nM, 16 nM for A549 and H1299, respectively), irradiated (2 Gy), immunostained for γH2AX (red) and 53BP1 (green), and then foci per nucleus counted for each time point (>100 nuclei counted). DAPI counterstaining showed the nuclei. Repair kinetics of NSCLC cells as in A and B, was obtained by plotting the %+SEM of remaining foci against time (FIG. 26C). *p<0.001, p<0.01 vs control, ANOVA. Data is representative of one of three experiments.

FIG. 27A: JIB-04 $IC_{50}$ determined by liquid colony assay in normal HBEC30KT and HBEC3KT cells. Values represent single wells of a single experiment. FIG. 27B: Clonogenic survival of HBEC3KT and HBEC30KT cells treated with indicated doses of JIB-04 and then irradiated as indicated. Cells treated with DMSO were used as control. Values represent the average survival fraction+SD of a single experiment done by triplicate. FIG. 22C: DNA DSB repair kinetics in HBEC30KT (FIG. 27C) cells. Cells were incubated with (black bar) or without (white bar) JIB-04 for 4 h (500 nM), irradiated (2 Gy), immunostained for γH2AX, and then γH2AX foci counted for each time point (average, 100 nuclei). DAPI counterstaining showed the nuclei. Repair kinetics of NSCLC cells was obtained by plotting the %+SEM of remaining foci against time. *p<0.05 vs control, ANOVA.

FIG. 28A: Schematic of reporter construct for NHEJ and HR repair assay. FIG. 28B: H1299 cells containing the NHEJ or the HR constructs treated for 4 h with JIB-04 or DMSO as control were transfected with the pCMV3xnls-I-SceI (functional endonuclease) and a pN1-mCherry plasmid as transfection control. Then cells were seeded in the presence or absence of JIB-04 and GFP quantified by FACs as described in C. FIG. 28C: Cells were analyzed by flow cytometry for GFP+24 h after transfection using green-versus-red fluorescent plot. 10,000 cells were analyzed in each sample and NHEJ or HR Repair Frequency (% GFP+ cells/% mCherry+ cells). Average+/–SEM of triplicates for one of three representative experiments is shown. ***p<0.001 vs control (Kruskal-Wallis). Representative FACS traces for the analysis of NHEJ and HR quantified in B.

FIG. 29A: U2OS cells were transfected with the NHEJ or HR constructs (0.25 ug and 0.5 ug respectively) and a pN1-mCherry plasmid (0.05 ug). Then cells were seeded in the presence or absence of JIB-04. Cells were analyzed by flow cytometry for GFP expression 12 h and 24 h after transfection using green-versus-red fluorescent plot. 10,000 cells were analyzed in each sample and NHEJ or HR Repair Frequency (% GFP+ cells/% mCherry+ cells) plotted. Average+/−SEM of triplicates for one of two representative experiments is shown. ***p<0.001 vs control (Kruskal-Wallis). FIG. 29B: Representative FACS traces for the analysis of NHEJ and HR shown in A.

FIG. 34A: DNA DSB repair kinetics in HCC-95 cells. Cells were incubated with or without JIB-04 for 4 h (35 nM), irradiated (2 Gy), and fixed 15 minutes after IR. Then cells were immunostained for γH2AX and 53BP-1, and the number of foci per nucleus counted for each time point (average, 100 nuclei counted). Images are representatives of two experiments. Repair kinetics of HCC95 cells was obtained by plotting the number of γH2AX and 53BP1 foci+SEM against time. Average shown represents one of two experiments. **p<0.01 vs control (Kruskal-Wallis). FIG. 34B: A549, H1299 and HCC95 cells were pre-treated with JIB-04 during 4 h followed by IR (2 Gy) and collected 15 min. Cellular extracts were prepared and H3K9me3 activity measured. Values are expressed as %+SEM of DMSO treated cells for each time point of a single experiment. *p<0.05 vs MOCK. FIG. 34C: HCC95 cells were pre-treated with JIB-04 during 4 h followed by IR (2 Gy) and collected 15 min, 6 h and 12 h post-IR. Cells were stained with PI to detect distribution of cell cycle after the treatments. Quantification of the percentages of cells at the different stages of cells cycle in response to JIB-4, IR and JIB-4+IR (left panel). Data in the histograms represent cells from a single experiment with the percentages of cells in G1, S, and G2-M illustrated after 6 h of IR. Data are representative of two independent experiments.

DESCRIPTION OF ILLUSTRATIVE EMBODIMENTS

Figures 1A, 1B, 1C, 1D, 1E, 1F, 1G, 1H:
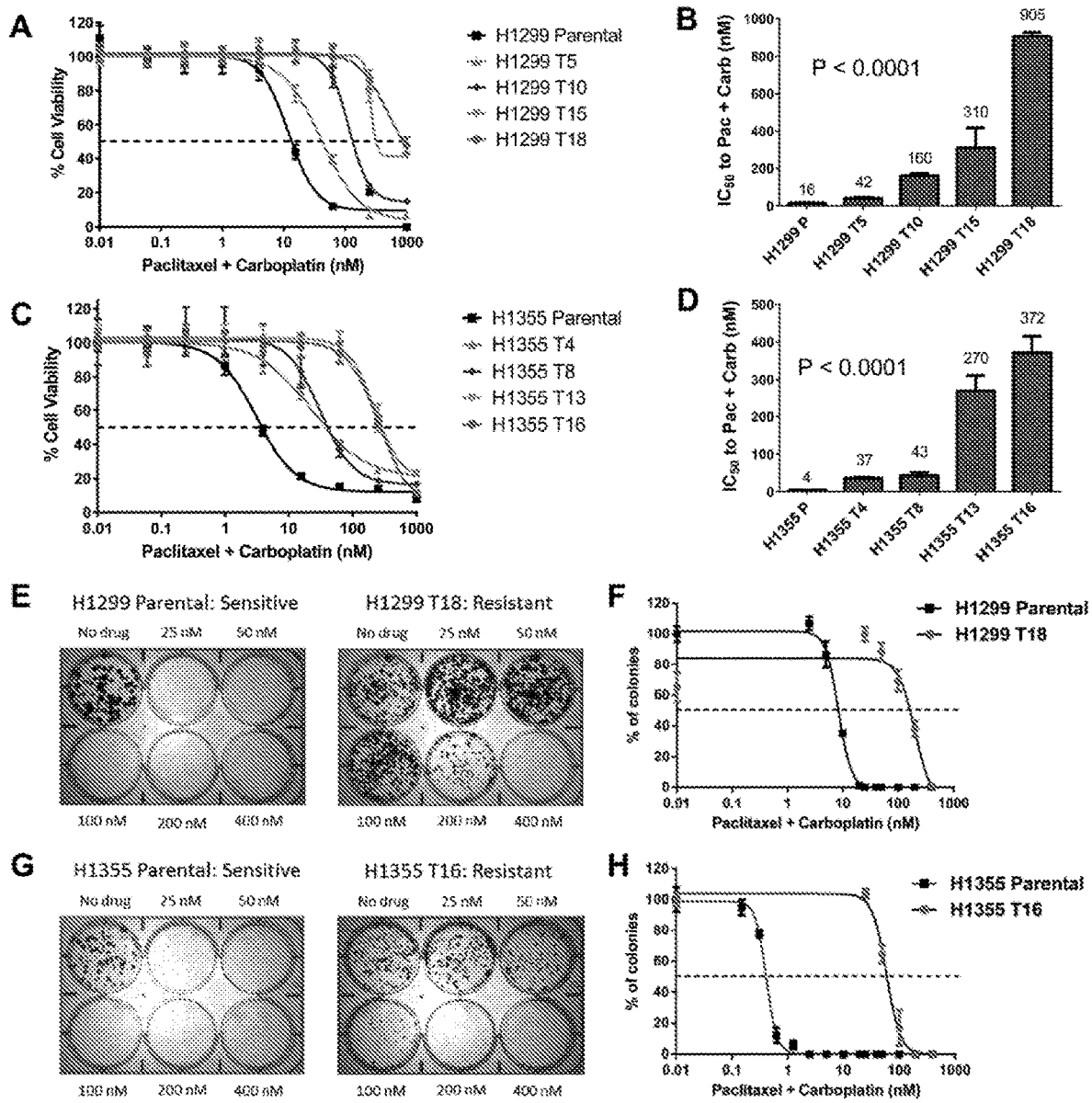
FIGS. 1A-1H. Long-term treated NSCLC cell lines develop progressively increasing resistance to paclitaxel+carboplatin standard chemotherapy.

The present invention provides methods for the treatment and prevention of chemoresistance in cancer as well as methods to sensitize cancer cells to radiation. It has been unexpectedly found that upregulation of JumonjiC histone lysine demethylases during preclinical models of NSCLC resistance to taxane-platin doublet chemotherapy provide an underlying epigenetic mechanism for drug resistance to this doublet while also defining a new actionable susceptibility. The current embodiments establish a connection between increased resistance to standard taxane-platin chemotherapy and progressive sensitization to JmjC KDM inhibitors. The present invention takes advantage of JmjC KDMs as new therapeutic targets for the treatment of drug resistant NSCLCs and for preventing emergence of taxane-platin drug tolerant clones from chemo-sensitive NSCLCs. In addition, several JmjC demethylase inhibitors such as JIB-04 are capable of blocking or delaying DNA repair in cancers that are relatively resistant to radiation, thereby robustly sensitizing cancer cells to radiation. A JmjC inhibitor may be used in conjunction with another therapeutic agent, such as radiation therapy to increase its therapeutic efficacy.

A. HISTONE DEMETHYLASE

Demethylases are a class of enzymes that remove methyl ($CH_3$—) groups from nucleic acids, proteins (in particular histones), and other molecules. Demethylase enzymes are important in epigenetic modification mechanisms. Demethylase proteins can alter transcriptional regulation of the genome by controlling the methylation levels that occur on DNA and histones and, in turn, regulate the chromatin state at specific gene loci within organisms. Histone demethylase proteins have a variety of domains that serve different functions. These functions include binding to the histone (or sometimes the DNA on the nucleosome), recognizing the correct methylated amino acid substrate and catalyzing the reaction, and binding cofactors. Cofactors include: alpha-keto glutarate and Fe(II), for JmjC-domain containing demethylases since they are hydroxylases/dioxygenases, and flavin adenine dinucleotide (FAD) for the LSD family of demethylases, which are amine oxidases. All Jumonji demethylases contain the conserved Jumonji C (JmjC) catalytic domain. Some Jumonji family members also contain one or more of the following domains: the plant homeobox domain (PHD), F-box domain, Jumonji N (JmjN) domain, ARID domain, tudor domain, tetracopeptide repeat (TPR) domain, zinc-finger-like domain.

There are several families of JmjC histone demethylases, which act on different substrates and play different roles in cellular function. A code has been developed to indicate the substrate for a histone demethylase. The substrate is first specified by the histone subunit (H1, H2A, H2B, H3, H4) and then the one letter designation and number of the amino acid that is methylated. The level of methylation is sometimes noted by the addition of "me #", with the numbers being 1, 2, and 3 for monomethylated, dimethylated, and trimethylated substrates, respectively. For example, H3K9me2 is histone H3 with a dimethylated lysine in the ninth position of the histone's sequence. The families of histone demethylases of relevance in the current embodiments includes KDM2 (KDM2A and KDM2B), KDM3 (KDM3A, KDM3B, and JMJD1C), KDM4 (KDM4A, KDM4B, KDM4C, and KDM4D), KDM5 (KDM5A, KDM5B, KDM5C, KDM5D), KDM6 (KDM6A, KDM6B), KDM7A, PHF8, KDM8, JARID2, FBXL19, JMJD4, JMJD5, JMJD6, JMJD7, JMJD7-PLA2G4B, JMJD8, HIF1AN, HR, HSPBAP1, MINA, N066, PHF2, TYW5, UTY.

B. JUMONJI C DEMETHYLASE INHIBITORS

JumonjiC demethylase inhibitors are generally structurally unique small molecules that selectively inhibit the activity of the Jumonji family of histone demethylases for example, by the disruption of protein/protein interactions. In one aspect, the JumonjiC demethylase inhibitor is JIB-04, GSK-J4, SD-70, ML324, KDM5-C70, PBIT, KDOHP64a, KDOQZ5, IOX1, IOX2, KDOMA83, KDMOBP69, NSC636819, or any analogs of the aforementioned compounds or any inhibitor of Jumonji enzymes that targets more than one member of the Jumonji enzyme family, wherein a Jumonji enzyme is any protein that contains a JumonjiC (JmjC) domain. It is also contemplated that the JumonjiC demethylase inhibitor of the current invention can be a pan-JumonjiC demethylase inhibitor or an inhibitor of more than one JumonjiC enzyme. In a specific embodiment, the JmjC inhibitor is JIB-04 and/or GSK-J4. JIB-04 is a "pan-JmjC demethylase inhibitor," i.e., it inhibits two or more JmjC enzymes. See Wang et al., 2013.

Each JumonjiC demethylase inhibitor may inhibit one or more of KDM2A, KDM2B, KDM3A, KDM3B, JMJD1C, KDM4A, KDM4B, KDM4C, KDM4D, KDM4E, KDM5A, KDM5B, KDM5C, KDM5D, KDM6A, KDM6B, KDM7A, PHF8, KDM8, JARID2, FBXL19, JMJD4, JMJD5, JMJD6, JMJD7, JMJD7-PLA2G4B, JMJD8, HIF1AN, HR, HSPBAP1, MINA, N066, PHF2, PLA2G4B, TYW5, or UTY or any JmjC containing protein. In another aspect the JumonjiC demethylase inhibitor inhibits KDM3A, and/or KDM3B, and/or JMJD1C. In yet another aspect, a JmjC inhibitor that particularly affects H3K4, H3K9, H3K36 and/or H4K20 methylation, can block or delay DNA repair in cancer and enhance the effects of radiation. Without wishing to be bound by theory, in one instance the use of a JmjC inhibitor as disclosed in the current invention could be effective as a monotherapy, targeting chemoresistant tumors after the development of resistance or targeting their intrinsic resistance. Chemoresistant tumors can be affected by greater percent reduction in final tumor volumes due to greater reliance on and/or upregulation of Jumonji demethylase pathways. It is also contemplated that a JmjC monotherapy can be used for the prevention of the emergence of drug tolerant persister colonies from cancerous cells and/or tumors, thereby providing a new therapeutic opportunity for not only targeting cancer after the development of drug resistance but also for preventing the emergence of chemoresistant subpopulations in cancers treated with standard chemotherapy. In another instance, a JmjC inhibitor can be used for the treatment of radiation resistant cancers and also for the enhanced response to radiation therapy of tumors that are partly responsive or non-responsive to radiation. Without wishing to be bound by theory, not all types of Jumonji inhibitors may be useful for radiosensitization. For example, Jumonji inhibitors that mainly/preferentially target H3K27me3 demethylases may not have this activity.

In some embodiments, the agent that inhibits a JmjC polypeptide is not a KDM1 or LSD1 inhibitor. KDM1/LSD1 enzymes are not classified as JmjC demethylase enzymes, as they do not have a JmjC protein domain.

C. CANCER AND CANCER THERAPY

Cancer cells that may be treated by methods and compositions of the invention include cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis *coli*; solid carcinoma; carcinoid tumor, malignant; bronchioloalveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; strumaovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblasticodontosarcoma; ameloblastoma, malignant; ameloblasticfibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; hodgkin's; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcomacell leukemia; myeloid leukemia; basophilic leukemia; eosinophilic leukemia; monocytic leukemia; mast cell leukemia; megakaryoblastic leukemia; myeloid sarcoma; and hairy cell leukemia.

Cancer therapies as used herein to treat chemoresistant cancer can refer to a substance that inhibits or prevents a cellular function and/or causes cell death or destruction. Chemotherapies include cytotoxic agents that come in contact with cancer cells such as radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$, and radioactive isotopes of Lu), chemotherapeutic agents or drugs, DNA-damaging agents, anti-mitotic agents, intercalating agents, growth inhibitory agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. A tumoricidal agent also causes destruction of tumor cells. DNA damaging agents include those cytotoxic agents that damage DNA leading to cell death or destruction. In another aspect, DNA damaging agents can also include ionizing radiation and waves that induce DNA damage, such as, γ-irradiation, X-rays, UV-irradiation, microwaves, electronic emissions, and the like. In one embodiment radiation therapy is different than chemotherapy when a radiation device or apparatus is employed to damage DNA using ionizing radiation or waves. Examples of radiation devices include therapeutic x-rays machines, linear accelerators, particle accelerators, sources of Co60 or Cs137 waves and UV irradiators among others. Mitotic agents include for example, mitotic inhibitors that inhibit mitosis such as in cell division by disrupting microtubules that function to pull the cell apart as it divides.

Examples of chemotherapies include plant alkaloids and derivatives; small molecules; anti-microtubule agents; taxanes, e.g., paclitaxel (TAXOL®), albumin-engineered nanoparticle formulation of paclitaxel (ABRAXANE™), docetaxel (TAXOTERE®); vinca alkaloids, e.g., vinblastine (VELBAN®), vincristine (ONCOVIN®), vindesine (ELDISINE®, FILDESIN®), and vinorelbine (NAVELBINE®); camptothecin analogs; alkylating agents such as cyclosphosphamide; platinum agents e.g., cisplatin, oxaliplatin, carboplatin; alkylsulfonates, e.g., busulfan; aziridines; ethylenimies, e.g., hexamethyl melamine, thiotepa; methylamelamines; acetogenins; delta-9-tetrahydrocannabinol; beta-lapachone; lapachol; colchicines; betulinic acid; bryostatin; callystatin; podophyllotoxin; podophyllinic acid; teniposide; cryptophycins; dolastatin; duocarmycin and analogues; eleutherobin; pancratistatin; sarcodictyin; spongistatin; hydrazines and triazines, e.g., procarbazine, altretamine, dacarbazine, temozolomide; mustard gas derivatives, e.g., mechlorethamine, chlorambucil, cyclophosphamide, ifosfamide, melphalan, mitomycin C, chlomaphazine, chlorophosphamide, estramustine, mechlorethamine, mechlorethamine oxide hydrochloride, novembichin, phenesterine, prednimustine, trofosfamide, uracil mustard; nitrosoureas, e.g., lomustine, carmustine, streptozocin; anti-tumor antibiotics, chromomycin, e.g., plicamycin, dactinomycin; bleomycin, aclacinomysins, actinomycin, authramycin, azaserine, bleomycin, cactinomycin, carabicin, carminomycin, carzinophilin, dactinomycin, detorubicin, 6-diazo-5-oxo-L-norleucine, dynemicin, marcellomycin, mitomycin; puromycin; anthracyclines, e.g., mitoxantrone, epirubicin, doxorubicin, idarubicin, daunorubicin, esorubicin, daunomycin; leucovorin; novantrone; edatrexate; aminopterin; ibandronate; topoisomerase inhibitors, e.g., irinotecan, topotecan, etoposide phosphate, amsacrine, etoposide and teniposide; difluoromethylomithine (DMFO); anti-metabolites; purine antagonist, e.g., 6-thioguanine, 6-thio-2'-deoxyguanosine, 6-mercaptopurine, thiamiprine; folic acid antagonist, e.g., methotrexate, pemetrexed; pyrimidine antagonist, e.g., foxuridine, capecitabine, 5-fluorouracil, cytarabine, gemcitabine, troxacitabine, ancitabine, azacitidine, 6-azauridine, carmofur, dideoxyuridine, doxifluridine, enocitabine, floxuridine; adenosine deaminase inhibitor, e.g., nelarabine, fludarabine, cladribine, pentostatin mitotic inhibitor; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mopidanmol; nitraerine; pentostatin; phenamet; pirarubicin; losoxantrone; 2-ethylhydrazide; procarbazine; razoxane; rhizoxin; sizofiran; spirogermanium; tenuazonic acid; triaziquone; 2,2',2'-trichlorotriethylamine; trichothecenes; urethan; vindesine; dacarbazine; mannomustine; mitobronitol; mitolactol; pipobroman; gacytosine; arabinoside (Ara-C); enzymes, e.g., pegaspargase, asparaginase; ribonucleotide reductase inhibitor, e.g., hydroxyurea; adrenocortical steroid inhibitor, e.g., mitotane; retinoids, e.g., bexarotene, isotretinoin, tretinoin (ATRA); bisphosphonates such as clodronate, etidronate, NE-58095, zoledronicacidlzoledronate, alendronate, pamidronate, tiludronate, risedronate; proteasome inhibitors, e.g., bortezomib (Velcade) and carfilzomib; hormonal therapy; anti-estrogens, e.g., fulvestrant; selective estrogen receptor modulators, e.g., tamoxifen, toremifene; aromatase inhibitors, e.g., letrozole, anastrozole, and exemestane; progesterone-like drugs, e.g., megestrol acetate; androgen therapy; anti-androgens, e.g., flutamide, enzalutamide, bicalutamide, and nilutamide; androgen synthesis inhibitors, e.g., ketoconazole, aminoglutethamide, and abiraterone acetate; luteinizing hormone-releasing hormone (LHRH) agonists, e.g., leuprolide, goserelin; LHRH antagonists, e.g., degarelix; radiopharmaceuticals, e.g., Radium 223 dichloride; and pharmaceutically acceptable salts, acids or derivatives of any of the above; as well as combinations of two or more of the above. Specifically, the chemotherapy is a taxane-platin combination therapy comprising paclitaxel-carboplatin or docetaxel-cisplatin doublet therapy or equivalent doublets.

Targeted cancer therapies are agents designed to interfere with specific molecules necessary for tumor growth and progression. Examples of targeted therapies include drugs or monoclonal antibodies that act as EGFR inhibitors, HER2 inhibitors, PI3K/Akt signaling inhibitors, MAPK inhibitors; JAK/STAT inhibitors; NF-kB inhibitors; mTOR inhibitors; RAS/RAF inhibitors, BRAF inhibitors, MEK inhibitors, ALK inhibitors, BCR-ABL inhibitors; PARP inhibitors; cell cycle inhibitors; checkpoint inhibitors; inhibitors of Notch, Wnt, Hedgehog, BMP, or TGF-beta signaling; telomerase inhibitors; TLR signaling inhibitors; MDR/MRP inhibitors; inhibitors of ABC transporters; mitochondrial inhibitors; oxidative phosphorylation (OXPHOS) inhibitors; calcium signaling inhibitors; ion channel inhibitors; insulin pathway inhibitors, inhibitors of insulin-like growth factor (IGF) receptor signaling; anti-angiogenic therapy; inhibitors of epigenetic enzymes or histone modulators, as well as combinations of two or more of the above.

Epigenetic modification plays crucial roles in gene expression and provides tools for the treatment of cancer. Epigenetic drivers of tumor drug tolerance can dynamically alter a multitude of transcriptional programs. Examples of epigenetic therapies include DNA methyltransferase (DNMT) inhibitors, e.g., 5-azacytidine (Vidaza), decitabine (5-aza-2'-deoxycytidine); histone deacetylase (HDAC) inhibitors, e.g., romidepsin (FK228), vorinostat (SAHA), trichostatin A, panobinostat, CHR-3996, quisinostat, entinostat (MS-275), mocetinostat (MGCD0103), histone acetyltransferase (HAT) inhibitors; sirtuin inhibitors; histone methyltransferase inhibitors, e.g., DOT1L inhibitor, MLL inhibitor, EZH2 inhibitor; LSD1 histone demethylase inhibitors; arginine methyltransferase inhibitors, arginine demethylase inhibitors, aurora kinase inhibitors; bromodomain (BRD) inhibitors; MBT domain inhibitors; and pharmaceutically acceptable salts, acids or derivatives of any of the above; as well as combinations of two or more of the above. The role epigenetic of enzymes in drug tolerance identifies them as potential therapeutic targets for overcoming drug resistance.

Immunotherapy includes antibodies or drugs or cell-based vaccines; e.g., immune checkpoint inhibitors, anti-PD-1 and/or anti-PDL-1, anti-CTLA-4. It is contemplated that a JmjC inhibitor can increase the efficacy of any of the aforementioned chemotherapies for the treatment of any of the aforemention cancer displaying chemoresistanttumors. In a specific embodiment, the chemotherapy is a taxane-platin combination therapy including paclitaxel-carboplatin or docetaxel-cisplatin doublet therapy, the JmjC inhibitor is JIB-04 and/or GSK-J4, and the cancer is non-small cell lung cancer (NSCLC). In another specific embodiment, the therapy is ionizing radiation with pre-administration of JIB-04 and/or an analogous Jumonji inhibitor and the cancer is NSCLC.

D. CHEMICAL DEFINITIONS

As used herein, a "small molecule" refers to an organic compound that is either synthesized via conventional organic chemistry methods (e.g., in a laboratory) or found in nature. Typically, a small molecule is characterized in that it contains several carbon-carbon bonds, and has a molecular weight of less than about 1500 grams/mole. In certain embodiments, small molecules are less than about 1000 grams/mole. In certain embodiments, small molecules are less than about 550 grams/mole. In certain embodiments, small molecules are between about 200 and about 550 grams/mole. In certain embodiments, small molecules exclude peptides (e.g., compounds comprising 2 or more amino acids joined by a peptidyl bond). In certain embodiments, small molecules exclude nucleic acids.

Compounds described herein may be prepared synthetically using conventional organic chemistry methods known to those of skill in the art and/or are commercially available (e.g., Sigma Aldrich® U.S.A. or ChemBridge Co., San Diego, Calif.).

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like.

Suitable pharmaceutically acceptable salts may also be formed by reacting the agents of the invention with an organic base such as methylamine, ethylamine, ethanolamine, lysine, ornithine and the like.

Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

Derivatives of compounds of the present invention are also contemplated. In certain aspects, "derivative" refers to a chemically modified compound that still retains the desired effects of the compound prior to the chemical modification. Such derivatives may have the addition, removal, or substitution of one or more chemical moieties on the parent molecule. Non-limiting examples of the types modifications that can be made to the compounds and structures disclosed herein include the addition or removal of lower alkanes such as methyl, ethyl, propyl, or substituted lower alkanes such as hydroxymethyl or aminomethyl groups; carboxyl groups and carbonyl groups; hydroxyls; nitro, amino, amide, and azo groups; sulfate, sulfonate, sulfono, sulfhydryl, sulfonyl, sulfoxido, phosphate, phosphono, phosphoryl groups, and halide substituents. Additional modifications can include an addition or a deletion of one or more atoms of the atomic framework, for example, substitution of an ethyl by a propyl; substitution of a phenyl by a larger or smaller aromatic group. Alternatively, in a cyclic or bicyclic structure, heteroatoms such as N, S, or O can be substituted into the structure instead of a carbon atom.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in Handbook of Pharmaceutical Salts: Properties, Selection and Use (2002), which is incorporated herein by reference.

E. PHARMACEUTICAL FORMULATIONS AND ADMINISTRATION THEREOF

1. Pharmaceutical Formulations and Routes of Administration

Pharmaceutical compositions of the present invention comprise an effective amount of one or more candidate substance or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one candidate substance or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The compounds of the invention may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, systemically, subcutaneously, subconjunctival, intravesicularlly, mucosally, intrapericardially, intraumbilically, intraocularally, orally, locally, via inhalation (e.g., aerosol inhalation), via injection, via infusion, via continuous infusion, via localized perfusion bathing target cells directly, via a catheter, via a lavage, in cremes, in lipid compositions (e.g., liposomes), or by other method or any combination of the foregoing as would be known to one of ordinary skill in the art (see, for example, Remington's Pharmaceutical Sciences, 1990).

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of a compound of the present invention. In other embodiments, the compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal, or combinations thereof.

The candidate substance may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine, or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. It may be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in certain embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the candidate substance is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. In certain embodiments, carriers for oral administration comprise inert diluents, assimilable edible carriers or combinations thereof. In other aspects of the invention, the oral composition may be prepared as a syrup or elixir. A syrup or elixir may comprise, for example, at least one active agent, a sweetening agent, a preservative, a flavoring agent, a dye, a preservative, or combinations thereof.

In certain embodiments, an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar, or both.

Additional formulations which are suitable for other modes of administration include suppositories. Suppositories are solid dosage forms of various weights and shapes, usually medicated, for insertion into the rectum, vagina, or urethra. After insertion, suppositories soften, melt or dissolve in the cavity fluids. In general, for suppositories, traditional carriers may include, for example, polyalkylene glycols, triglycerides, or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, certain methods of preparation may include vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin, or combinations thereof.

2. Combination Therapy

In some embodiments, it is contemplated that the JmjC inhibitor of the invention may be used in conjunction with additional therapeutic agents as part of a treatment regimen. This process may involve administering to the subject the agents at the same time or within a period of time wherein separate administration of the agents produces a desired therapeutic benefit. This may be achieved by contacting the cell, tissue, or organism with a single composition or pharmacological formulation that includes two or more agents, or by contacting the cell with two or more distinct compositions or formulations, wherein one composition includes one agent and the other includes another.

Figures 17A, 17B, 17C, 17D, 17E, 17F:
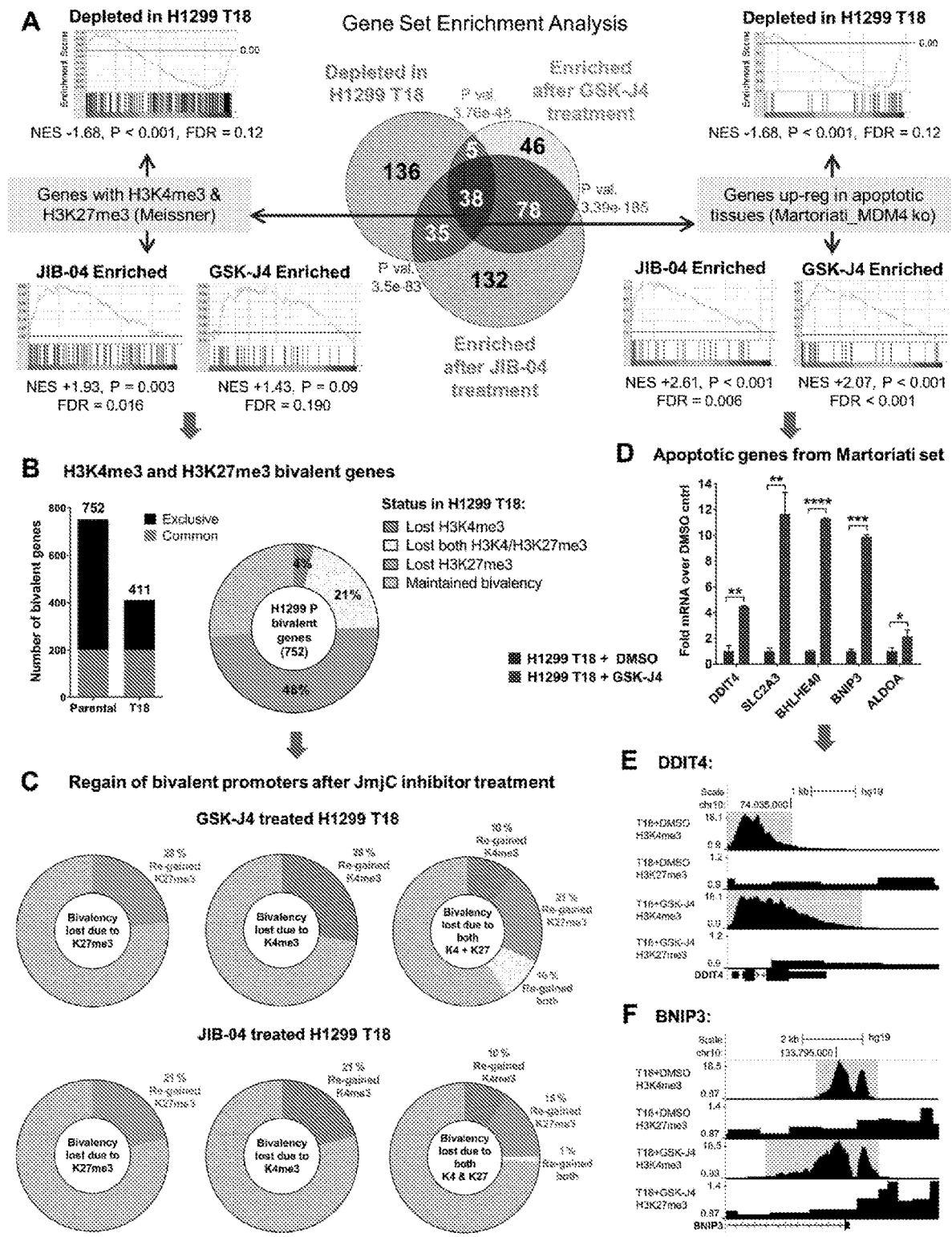
FIGS. 17A-17F. JIB-04 and GSK-J4 treated chemoresistant cells exhibit reversal of a subset of deregulated transcriptional programs, regain of H3K4me3-H3K27me3 promoter bivalency and induction of pro-apoptotic genes.
Figures 22A, 22B, 22C, 22D:
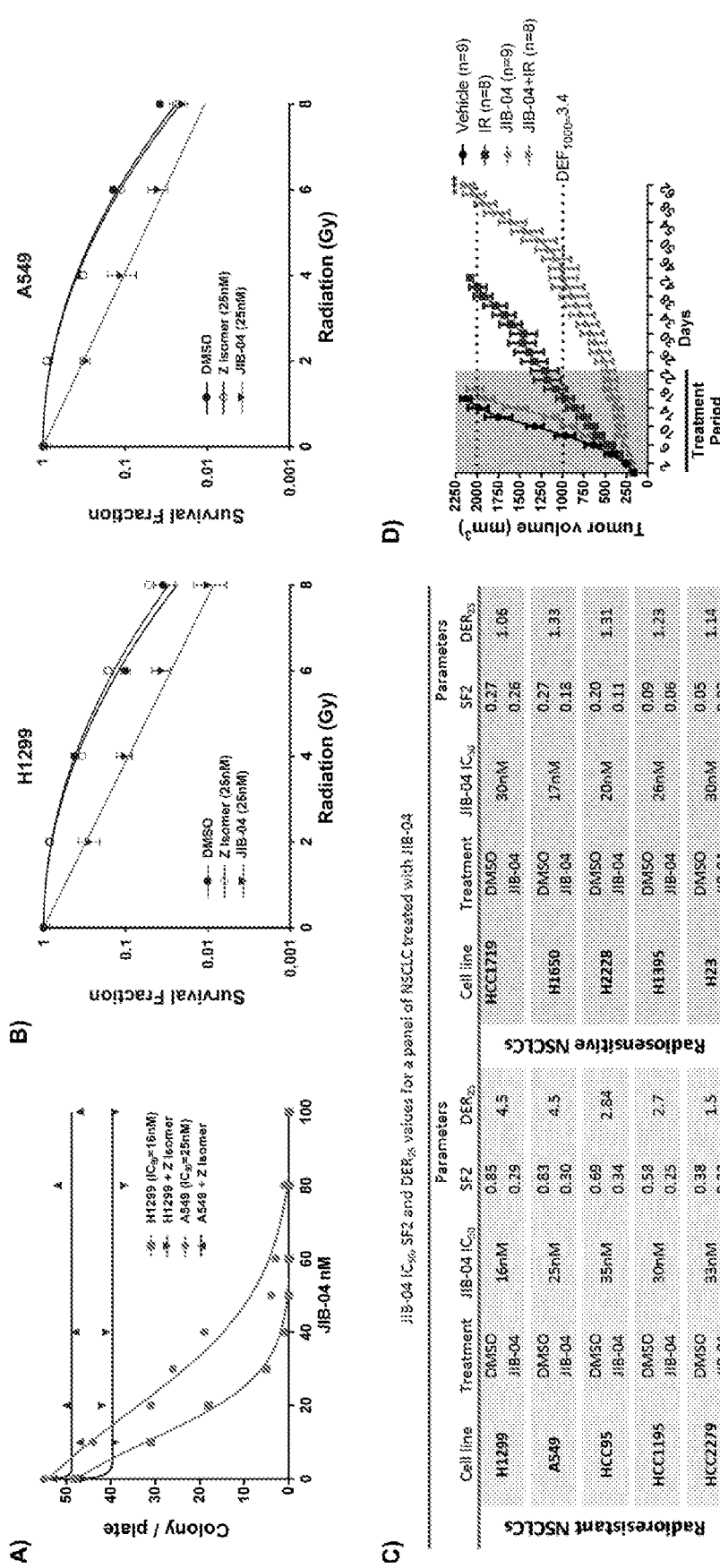
FIGS. 22A-22D. JIB-04 increased the sensitivity of radioresistant NSCLC cells and tumors to IR.
Figure 23:
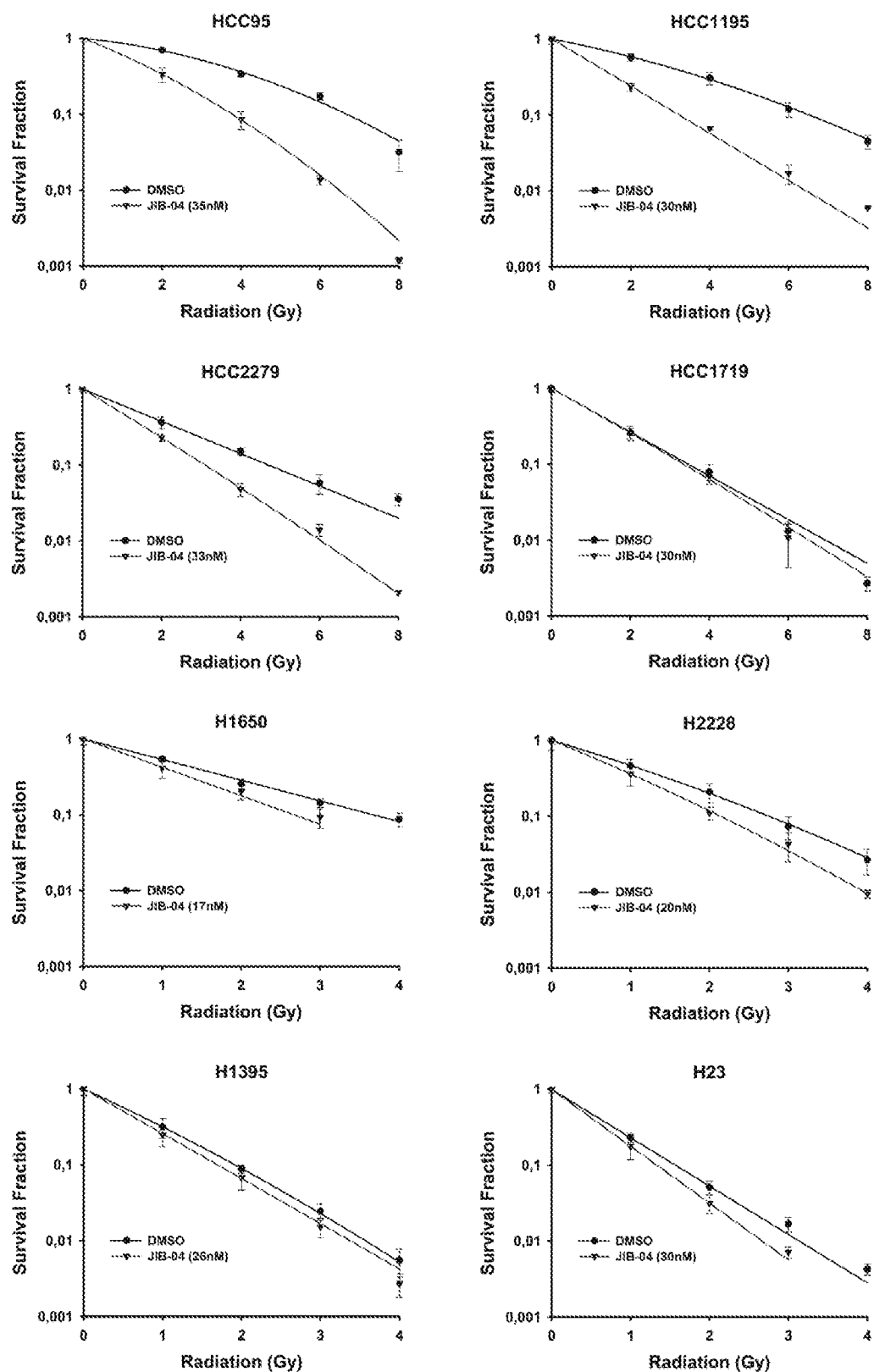
FIG. 23. JIB-04 increased the sensitivity of radioresistant but not radiosensitive NSCLC cells to IR. Clonogenic survival of radioresistant (HCC95, HCC1195 and HCC2279) and radiosensitive (HCC1719, H23, H1650, H1395 and H2228) NSCLC cell lines treated with JIB-04 or DMSO control and then irradiated as indicated. Graph represents three experiments for HCC1719 and one experiment for the other cell lines. Each condition was evaluated by triplicates and error bars represent SD.
Figures 30A, 30B:
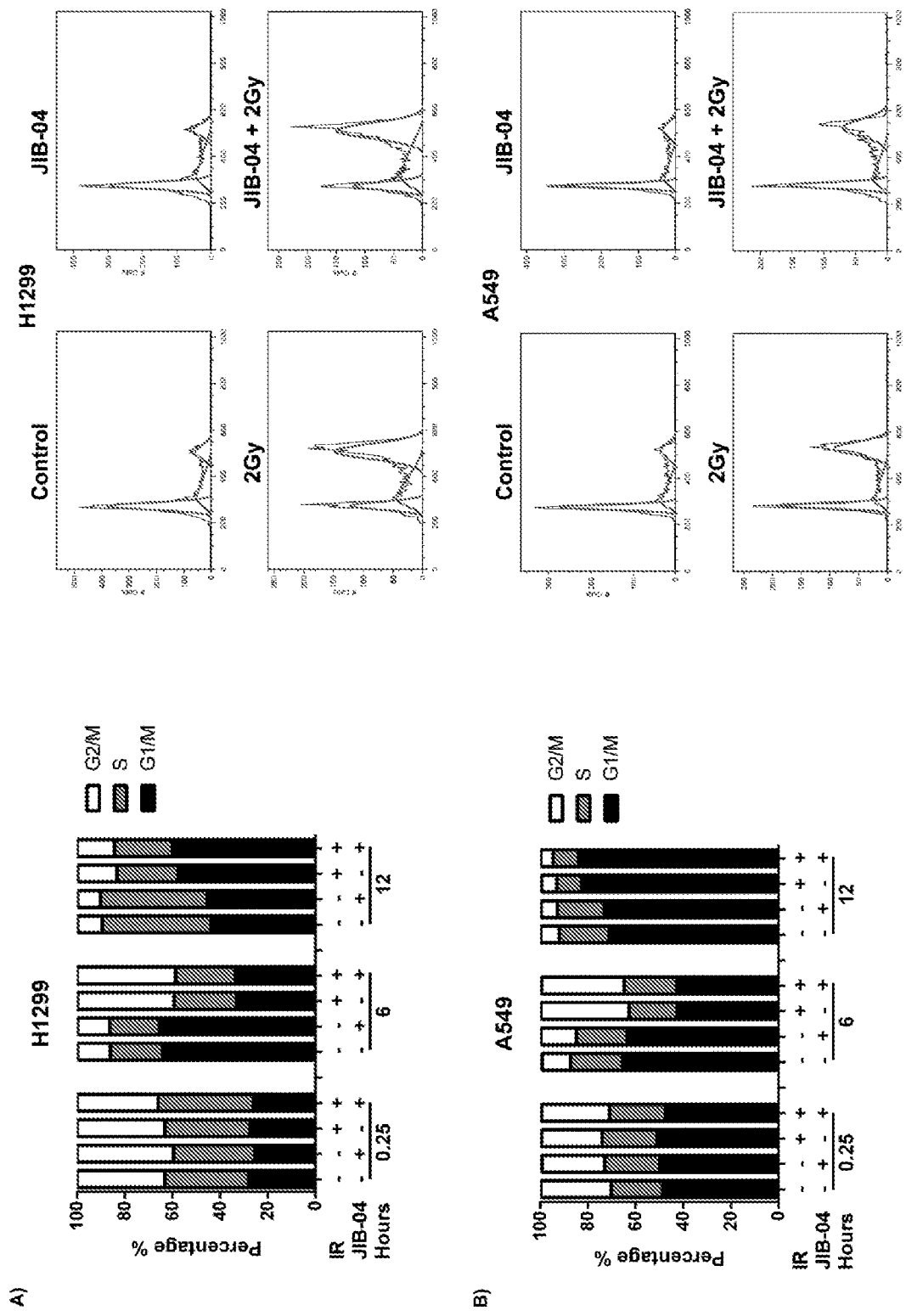
FIGS. 30A-30B. JIB-04's effect on DSB repair is not related with changes in G2-M checkpoint arrest or cell cycle distribution in NSCLC cells. H1299 (FIG. 30A) and A549 (FIG. 30B) cells were pre-treated with JIB-04 during 4 h followed by IR (2 Gy) and collected 15 min, 6 h and 12 h post-IR. Cells were stained with PI to detect distribution of cell cycle after the treatments. Quantification of the percentages of cells at the different stages of cell cycle in response to JIB-4, IR and JIB-4+IR (left panel). Data in the histograms represent cells from a single experiment with the percentages of cells in G1, S, and G2-M illustrated after 6 h of IR. Data are representative of two independent experiments.
Figure 35:
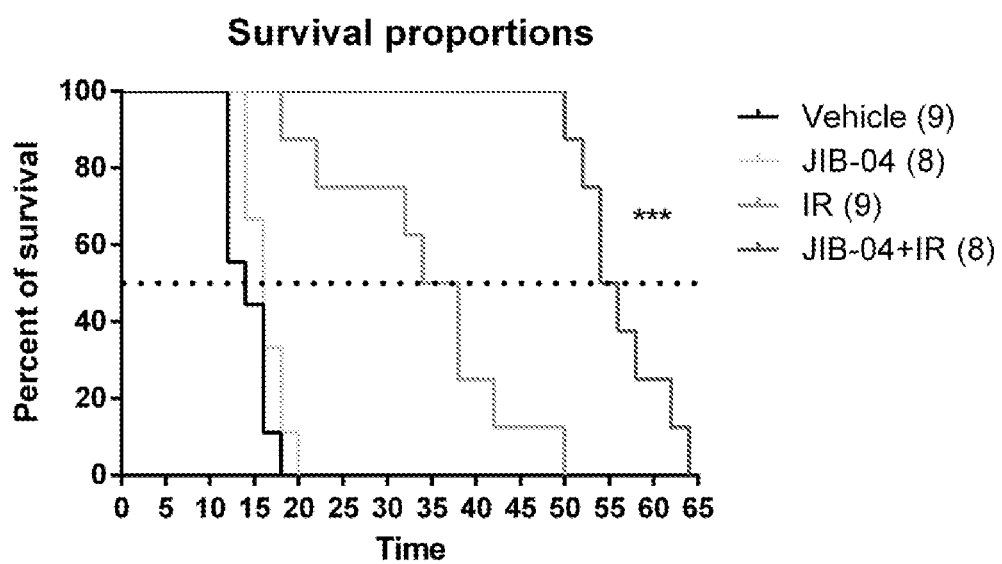
FIG. 35. JIB-04 increases radiation response in vivo in a sustained manner and prolongs survival of tumor bearing animals. The animals shown in FIG. 17D were followed post end of treatment on day 22. Survival was monitored and plotted in standard Kaplan-Meir curves. A significant increase in survival time was seen when JIB-04 was administered with IR.

In a particular aspect, the JmjC inhibitor is used in conjunction with radiation therapy. The current regiment for radiation therapy employs radiation alone or concurrent with cycles of a standard chemotherapy which is often limited due to toxicities to normal healthy cells. The use of a JmjC inhibitor to radiosenzitize cancer cells and not healthy cells can increase radiation response without general toxicity. In the current embodiments, it has been surprisingly found that doses of JmjC inhibitors that give robust radiosensitization do not cause any overt toxicity and are lower than the doses required to inhibit tumor growth without radiation under the same conditions (FIGS. 17D and 30). Furthermore, the combination of Jumonji inhibitor (JIB-04) followed by radiation results in a stronger effect than simply the addition of each therapy on its own and prolongs survival in tumor bearing mice (FIGS. 22D, 35). Examples of radiation toxicities that may be diminished by combined therapy with JIB-04 or analogous Jumonji inhibitor include but are not limited to: nausea, vomiting, hair loss, general weakness, skin rashes, pneumonitis, mucositis, orbital edema, brain edema, diarrhea, anemia, and other side effects or undesired consequences of exposure to therapeutic radiation.

The compounds of the present invention may precede, be co-current with and/or follow the other agents or radiation by intervals ranging from minutes to weeks. In embodiments where the agents or radiation are applied separately to a cell, tissue or organism, one would generally ensure that a significant period of time did not expire between the time of each delivery, such that the agents would still be able to exert an advantageously combined effect on the cell, tissue or organism. For example, in such instances, it is contemplated that one may contact the cell, tissue or organism with two, three, four or more modalities substantially simultaneously (i.e., within less than about a minute) with the JmjC inhibitor. In other aspects, one or more additional agents may be administered or provided within 1 minute, 5 minutes, 10 minutes, 20 minutes, 30 minutes, 45 minutes, 60 minutes, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 1 week, 2 weeks, 3 weeks, 4 weeks, 5 weeks, 6 weeks, 7 weeks, or 8 weeks or more, and any range derivable therein, prior to and/or after administering the JmjC inhibitor. For a specific example in cells and mice, a Jumonji inhibitor was administered first followed by radiation after 4 hours. The pre-administration of Jumonji inhibitor may give optimal radiosensitization compared to simultaneous administration or the reverse order.

Various combination regimens of the agents may be employed. Non-limiting examples of such combinations are shown below, wherein a JmjC inhibitor is "A" and a second agent or radiation is "B":

cancer that turns out to be chemotherapy- or radiation-resistant. Alternatively, a patient may have a recurring cancer. Without wishing to be bound by theory, the use a JmjC inhibitor in combination with another chemotherapy or radiation therapy can result in greater percent reduction in final tumor volumes by slowing tumor growth and/or decreasing tumor growth rate and/or decreasing metastasis or recurrence. A combination therapeutic regime including a JmjC inhibitor of the current invention could also provide a synergistic effect to prevent the emergence of drug tolerant persister colonies from cancerous cell lines and/or untreated tumors that would not only provide a new therapeutic opportunity for targeting cancer after development of drug resistance but also for possibly preventing the emergence of chemoresistant subpopulations in cancers treated with standard chemotherapy. In one embodiment, the combination chemotherapy is a taxane-platin combination therapy in combination with a JmjC inhibitor such as JIB-04 and/or GSK-J4 and the cancer is non-small cell lung cancer (NSCLC). In another embodiment, the combination therapy is a radiation therapy in combination with a JmjC inhibitor such as JIB-04 and the cancer is any radioresistant cancer.

In another embodiment, the cancer is any cancer with amplification and/or upregulation of Jumonji enzymes or higher than normal levels of Jumonji enzyme activity or deregulation of histone methylation pathways, and the therapy is JIB-04 or another Jumonji inhibitor alone or in combination with standard chemotherapy or radiotherapy for that cancer type. In yet another embodiment, the cancer is any cancer with an intact DNA repair capacity and the treatment is JIB-04 or another inhibitor of Jumonji demethylases other than H3K27 demethylase specific inhibitors, alone or in combination with radiotherapy.

In some embodiments, it is contemplated that JmjC inhibitor may be used as a therapy alone as a monotherapy and not in combination with any other therapeutic agent. In particular it is contemplated that JmjC inhibitor may be used without any additional therapeutic agent for the treatment and prevention of chemotherapy resistance in cancer.

F. ORGANISMS AND CELL SOURCE

Cells that may be used in many methods of the invention can be from a variety of sources. Embodiments include the use of mammalian cells, such as cells from monkeys, chimpanzees, rabbits, mice, rats, ferrets, dogs, pigs, humans, and cows. Alternatively, the cells may be from fruit flies, yeast, or *E. Coli*.

Methods of the invention can involve cells, tissues, or organs involving the heart, lung, kidney, liver, bone marrow, pancreas, skin, bone, vein, artery, cornea, blood, small intestine, large intestine, brain, spinal cord, smooth muscle, skeletal muscle, ovary, testis, uterus, and umbilical cord or any other cell type, tissue or organ from a mammal.

Moreover, methods can be employed in cells of the following type: platelet, myelocyte, erythrocyte, lympho-

| A/B/A | B/A/B | B/B/A | A/A/B | A/B/B | B/A/A | A/B/B/B | B/A/B/B |
|-------|-------|-------|-------|-------|-------|---------|---------|
| B/B/B/A | B/B/A/B | | A/A/B/B | A/B/A/B | | A/B/B/A | B/B/A/A |
| B/A/B/A | B/A/A/B | | A/A/A/B | B/A/A/A | | A/B/A/A | A/A/B/A |

In some embodiments, more than one course of therapy may be employed. It is contemplated that multiple courses may be implemented. In certain embodiments, a patient may have previously undergone radiation or chemotherapy for a cyte, adipocyte, fibroblast, epithelial cell, endothelial cell, smooth muscle cell, skeletal muscle cell, endocrine cell, glial cell, neuron, secretory cell, barrier function cell, contractile cell, absorptive cell, mucosal cell, limbus cell (from cornea), stem cell (totipotent, pluripotent or multipotent), unfertilized or fertilized oocyte, or sperm or cancer cell or any other disease cell.

G. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

To study the progression of NSCLC resistance to standard taxane-platin combination therapy, isogenic resistant NSCLC cell line variants were developed through long-term drug treatment using schedules of drug on/drug off cycles of therapy to mimic clinical treatment regimens. These models were then used to search for clinically relevant targets for drug resistant lung cancers by integrating genome-wide mRNA expression profiles of resistant cell line variants and the corresponding xenografts, and by evaluating the preclinical resistance signature for its ability to predict recurrence-free survival outcome in neoadjuvant chemotherapy treated NSCLC patients. Intriguingly, the studies uncovered epigenetic alterations in chemoresistant cells encompassing several different members of the Jumonjihistone lysine demethylase family. Without being bound by theory, these epigenetic mechanisms conferred a survival or adaptive advantage to chemotherapy treated cancer cells and may be therapeutically exploited to abrogate NSCLC cells that develop resistance to standard taxane-platin chemotherapy.

Example 1

Experimental Procedures
1. Cell Lines

NSCLC lines were obtained from the Hamon Cancer Center Collection (University of Texas Southwestern Medical Center). Cell lines have been DNA fingerprinted using PowerPlex 1.2 kit (Promega) and confirmed to be free of *mycoplasma* using e-Myco kit (Boca Scientific). Cells were maintained in RPMI-1640 (Life Technologies Inc.) with 5% FBS at 37° C. in a humidified atmosphere containing 5% $CO_2$.

2. In Vitro Drug Treatment

NSCLC lines were treated with paclitaxel+carboplatin combination, given in a ~2:3 wt/wt ratio, to mirror the clinical dosage values of ~225 mg/m2 and ~330 mg/m2, paclitaxel and carboplatin respectively. Note that considering the molecular weights of the two drugs, this translates to approximately a 1 to 3.4 molar ratio. Drugs were given in cycles, following a drug on/drug off treatment scheme. Each cycle consisted of 4-5 days of drug treatment and drug-free culturing for about 1-2 weeks or more to allow the surviving cells to repopulate the plate. Treatment was started with 2x-3xIC50 doses and doses were incremented with increasing treatment cycles, ultimately reaching ~30x-50xIC50 doses, depending on the cell line. Untreated parental cells were simultaneously maintained at all times for comparison. Cell viability was assessed in 96-well plates using standard MTS assays (Promega). Treatment duration in MTS assays was 4 days. Drugs were tested in two- or four-fold serial dilutions, totaling 8 different drug concentrations, with 8 replicates per concentration. Response was validated in multiple replicate plates (n≥3).

3. In Vivo Studies

Animals were housed under standard, sterile conditions at UTSW animal facility. All experiments were carried out under approved IACUC protocols and followed UTSW animal care procedures. For tumor growth rate studies and docetaxel+cisplatin drug response comparisons, 6-8 week old female NOD/SCID mice were used. For all subsequent in vivo drug response studies, 6 week old female athymic nude mice were used (Charles River Labs, Jackson Labs). Experimental details are provided in supplemental information.

4. Patient Tumors

NSCLC patient tumor dataset was obtained from MD Anderson Cancer Center (SPORE). This included both chemo-naïve and neoadjuvant treated tumors, and had complete histopathological and clinical annotation. Fresh frozen tumor samples from the time of resection were used for Illumina gene expression profiling and some were formalin-fixed, paraffin-embedded (FFPE) tumors for tissue microarrays (TMA).

5. Microarrays

Gene expression profiling was performed using Illumina HumanWG-6 V3 BeadArrays (for NSCLC patient tumors) or Illumina HumanHT-12 V4 BeadArrays (for cell lines and xenografts). Cell line and xenograft microarrays included biological replicates (Cell lines: 5 for parental, 3 for most resistant variant, 2 for each intermediate resistance timepoint; Xenografts: 3 tumors each for parental and resistant group). Data were pre-processed using the R package mbcb for background correction (Ding et al., 2008), then log-transformed and quantile-normalized with the R package preprocessCore or using in-house MATRIX software (MicroArrayTRansformation In eXcel). Microarray data can be found under GEO accession GSE77209.

6. Microarray Data Analysis

Log ratios, unpaired t-test p values and color-coded heat maps were obtained using MATRIX. For comparisons involving progressively resistant cell line series, analyses were performed using R package by fitting linear regression model on gene expression data against the log transformed $IC_{50}$ values as measures of drug response. We fitted beta-uniform mixture model to a set of p-values using the R package ClassComparison. Genes with p-values below the FDR cutoff of 0.1 were considered statistically significant. For xenograft data, differential gene expression analysis was performed by student's t-test. Using 35 gene signature, unsupervised hierarchical clustering (Eisen et al., 1998) was performed to separate neoadjuvant chemotherapy treated patients into two groups. Clustering was based on Euclidean distance matrix and maximum linkage method. Kaplan-Meier survival analysis and multivariate Cox regression were performed by R survival package and replotted using Graphpad Prism 6.00 (GraphPad Software, La Jolla, Calif. USA). R code is provided in Sweave report.

7. Statistical Methods

All statistical tests including two-way ANOVA with Sidak's multiple comparisons test, one-way ANOVA with Dunnett's multiple comparisontest, post-test for linear trend and unpaired t-tests were performed using GraphPad Prism 6.00. P values are represented as *$P<0.05$, $P<0.01$, *$P<0.001$ and ****$P<0.0001$. For drug treatments, dose response curves and $IC_{50}$ values were calculated using GraphPad Prism or in-house DIVISA (Database of InVItro Sensitivity Assays; L. Girard). For drug combination in colony formation, delta Bliss excess was calculated as shown previously (Wilson et al., 2014). Bliss expectation was calculated as A+B−(A×B), where A and B denote the fractional responses from drugs A and B given individually. The difference between Bliss expectation and observed response from combination of drugs A and B at the same doses is the delta Bliss excess.

8. Drugs

Cell lines were tested for response to several drugs including paclitaxel (Bedford Labs/Hikma Pharmaceuticals and also from Hospira, Lake Forest, Ill.), carboplatin (Sandoz Inc., Princeton, N.J. and from Sagent Pharmaceuticals, Schaumburg, Ill.), docetaxel (LC Laboratories, Woburn, Mass.), cisplatin (APP Pharmaceuticals, Schaumburg, Ill.), doxorubicin (Teva Parenteral, Irvine, Calif.), vinorelbine (Pierre Fabre Company, Castres, France), irinotecan hydrochloride (Sandoz Inc., Princeton, N.J.), gemcitabine (Eli Lilly and Company, Indianapolis, Ind.), pemetrexed (Eli Lilly and Company, Indianapolis, Ind.), fludarabine (Selleck Chemicals, Houston, Tex.), verapamil (Sigma-Aldrich), PGP-4008 (Santa Cruz Biotechnology), depsipeptide/romidepsin (ApexBio, Houston, Tex.), trichostatin A (Sigma-Aldrich, St. Louis, Mo.), GSK126 (Xcess Biosciences, San Diego, Calif.) and JIB-04 (Synthetic chemistry core at UT Southwestern). NU 9056, PFI 3, PRT 4165, SGC-CBP30, GSK-J5 and GSK-J4 were from Tocris Bioscience (Bristol, UK).

9. MTS Assays

Cell viability was assessed by standard MTS assays using Promega's CellTiter reagents. Eight drug concentrations given as two- or four-fold dilutions were tested for each chemotherapeutic agent. In addition, each experiment contained eight replicates per concentration and the entire assay was performed in multiple replicates (n≥3).

10. Colony Formation 400 cells were seeded per well in six well plates and treated with various drug concentrations the next day. After 2-3 weeks, colonies were stained with 0.5% crystal violet, 3% formaldehyde solution and counted both manually and automatically using Quantity One image analysis software (Bio-Rad).

11. Flow Cytometry

Cells were incubated with FITC- or APC-conjugated antibodies or appropriate isotype control antibody (BD Biosciences) at 4° C. for 30 min in dark. Cells were washed, resuspended in HBSS+ and stained with Propidium Iodide before flow cytometry. For cell cycle analysis, briefly cells were fixed in cold 70% EtOH and incubated at 37° C. for 30 min in staining buffer containing 50 µg/ml Propidium Iodide, 50 µg/ml RNAse A, 0.05% Triton X-100 and PBS. Flow cytometric profiling was performed on a FACScan or FACSCalibur flow cytometer (BD Biosciences) and analyzed using FlowJo software (Treestar).

12. Tritiated Docetaxel Accumulation Assay

Cells were exposed to [$^3$H]-docetaxel for different timepoints. Protein lysates were collected and quantified using BCA reagent. Samples were scintillated with Ecolume™ liquid scintillation cocktail. Drug accumulation was calculated as CPM/mg protein.

13. siRNA Knockdown

ABCB1 knockdown was achieved using three individual ABCB1 siRNAs (Qiagen) and LipofectamineRNAiMax (Invitrogen), following standard reverse transfection protocols. Silencing efficiency was detected using real-time PCR.

14. NSCLC Patient Tissue Microarray (TMA) and Immunohistochemistry (IHC)

FFPE tumor tissues were used to construct NSCLC tissue microarray #3 (TMA3) for immunohistochemistry. IHC staining was done using a Leica Bond autostainer, with rabbit monoclonal antibody for KDM3B (Cell Signaling Technology, clone C6D12, cat #3100, dilution 1:80). A human colon adenocarcinoma specimen was used as positive control. Stained samples were assigned an expression score by the pathologist.

15. In Vivo Studies

Parental and resistant NSCLC cell lines ($1\times10^6$ cells in PBS or RPMI for H1299; $5\times10^6$ cells in PBS/matrigel for H1355 and HCC4017) were injected subcutaneously into the right flank of mice. Tumor growth was monitored by caliper measurements and tumor volume was calculated by 0.5× length×width$^2$). Treatment was started when tumors reached ~150-200 mm3. Drug/Vehicle therapy was given to tumor volume matched pairs. Docetaxel (3 mg/kg) and cisplatin (3 mg/kg) were given i.p. once a week for 3 weeks. For JIB-04 studies, nude mice were randomized to receive either of 5, 20 or 50 mg/kg doses or vehicle, 3× per week for 2 weeks by gavage in 12.5% cremophor EL, 12.5% DMSO, aqueous suspension. For GSK-J4 studies, mice were given 100 mg/kg GSK-J4, every day, for 10 consecutive days or DMSO vehicle control, as used previously (Hashizume et al., 2014).

16. Gene Set Enrichment Analysis (GSEA) on Microarray Data

Ranked lists of differentially expressed genes from microarray analyses (fold change >=1.5, t-test p value <=0.05) were assessed by GSEAPreranked tool through the GSEA desktop application (http://www.broadinstitute.org/gsea/downloads.jsp). Curated gene sets (C2) from the Molecular Signatures Database v5.0/MSigDB (Subramanian et al., 2005) were interrogated. After filtering out genes that were not in the expression dataset, gene sets smaller than 15 genes or larger than 3000 genes were excluded from the analysis. GSEA was run using 1000 gene set permutations to generate False Discovery Rate (FDR). Default settings were used for normalizing the enrichment scores (NES).

17. ChIP-Seq Analysis of Histone H3K27Me3

H1299 parental and T18 cells at 80% confluency (~$1\times10^7$) were cross-linked with 1% formaldehyde for 10 minutes at 37° C., and quenched with 125 mM glycine at room temperature for 5 minutes. The fixed cells were washed twice with cold PBS, scraped, and transferred into 5 ml PBS containing Mini EDTA-free protease inhibitors (Roche). After centrifugation at 700 g for 4 minutes at 4° C., the cell pellets were resuspended in 1.5 ml ChIP lysis buffer (1% SDS, 10 mM EDTA, 50 mM Tris-HCl [pH 8.1] with protease inhibitors) and sonicated at 4° C. with a Bioruptor (Diagenode) (30 seconds ON and 30 seconds OFF at highest power for 2×15 minutes). The chromatin predominantly sheared to a fragment length of ~250-750 bp was centrifuged at 20,000 g for 15 minutes at 4° C. 100 µl of the supernatant was used for ChIP, and DNA purified from 30 µl of sheared chromatin was used as input. A 1:10 dilution of the solubilized chromatin in ChIP dilution buffer (0.01% SDS, 1.1% Triton X-100, 1.2 mM EDTA, 167 mM NaCl 16.7 mM Tris-HCl [pH 8.1]) was incubated at 4° C. overnight with 10 µg of a mouse monoclonal antibody anti-Histone H3K27me3 (Abcam, cat #ab6002). Immunoprecipitation was carried out by incubating with 40 µl pre-cleared Protein G Sepharose beads (Amersham Bioscience) for 1 hour at 4° C., followed by five washes for 10 minutes with 1 ml of the following buffers: Buffer I: 0.1% SDS, 1% Triton X-100, 2 mM EDTA, 20 mM Tris-HCl [pH 8.1], 150 mM NaCl, protease inhibitors; Buffer II: 0.1% SDS, 1% Triton X-100, 2 mM EDTA, 20 mM Tris-HCl [pH 8.1], 500 mM NaCl, protease inhibitors; Buffer III: 0.25 M LiCl, 1% NP-40, 1% deoxycholate, 1 mM EDTA, 10 mM Tris-HCl [pH 8.1]; twice with TE buffer [pH 8.0]. Elution from the beads was performed twice with 100 μl ChIP elution buffer (1% SDS, 0.1 M NaHCO$_3$) at room temperature (RT) for 15 minutes. Protein-DNA complexes were de-crosslinked by heating at 65° C. in 192 mM NaCl for 16 hours. DNA fragments from immunoprecipitated chromatin and input were purified using QiaQuick PCR Purification kit (QIAGEN) and eluted into 30 μl H2O according to the manufacturer's protocol after treatment with RNase A and Proteinase K.

For ChIP-Seq, barcoded libraries of ChIP and input DNA were generated with the TruSeq® ChIP Sample Preparation Kit (Illumina), and 50-nt single-end reads were generated with the HiSeq2000 system (Illumina). Sequence reads were aligned to the human reference genome (hg19) using Bowtie2 (v.2.2.5) (Langmead et al., 2009). Uniquely mapped reads with ≤2 mismatches to the reference sequence were retained for further analysis; for H1299 parental H3K27me3 and H1299 T18 H3K27me3, 26,100,406 and 29,586,658 reads were obtained, respectively and for H1299 parental input and H1299 T18 input, 26,995,155 and 25,187, 823 reads were obtained, respectively. ChIP-Seq enrichment plots were generated using ngs.plot tool (Shen et al., 2014). Aligned bam files are provided as input to Ngs.plot to calculate read count per million mapped reads over all the ENSEMBL annotated gene body regions in the human genome. For each ChIP-Seq sample, the average signal in −2 kb with respect to transcription start site (TSS), gene body and 2 kb downstream of transcription end site (TES) regions were subtracted from respective input sample signal and visualized in the enrichment plot.

18. Quantitative RT-PCR

Total RNA was isolated using RNeasy Plus Mini kit (Qiagen) and cDNA was generated using iScript cDNA synthesis kit (BioRad). For epigenetic enzymes, transcripts were detected by SYBR Green chemistry in real time quantitative PCR assays using validated primers. TBP and GAPDH were used as endogenous controls. For H1299 T18, cyclophilin B was used as control (since TBP and GAPDH showed DNA amplification and increased mRNA expression). For all non-epigenetic transcripts, TaqMan probes (Life Technologies) were utilized in multiplex with GAPDH internal reference gene. Additionally, a reference sample containing pooled RNA from normal human and tumor tissues (Stratagene) was used. PCR reactions were run using the ABI 7300 Real-time PCR System and analyzed with the included software. The comparative $C_T$ method was used to compute relative mRNA expression.

TABLE 1

SYBR Green Primers for Histone Lysine Demethylase Genes:

| Gene | Forward/Reverse Primer Sequence | RefSeq# |
|---|---|---|
| KDM1A | CTAATGCCACACCTCTCTCAACTC (SEQ ID NO: 1)<br>CTAATGCCACACCTCTCTCAACTC (SEQ ID NO: 2) | NM_015013.2<br>NM_015013.2 |
| KDM2A | TCCACCGGCTGATAAACCA (SEQ ID NO: 3)<br>AGCCGGAAGTCGGTCATGT (SEQ ID NO: 4) | NM_012308.1<br>NM_012308.1 |
| KDM2B | GCGCTCCCACCTCACTCA (SEQ ID NO: 5)<br>CCGAAGAGAAGCCGTCTATGC (SEQ ID NO: 6) | NM_001005366.1<br>NM_001005366.1 |
| KDM3A | GTGGTTTTCAGCAACCGTTATAAA (SEQ ID NO: 7)<br>CAGTGACGGATCAACAATTTTCA (SEQ ID NO: 8) | NM_018433.4<br>NM_018433.4 |
| KDM3B | TGCCCTTGTATCAGTCGACAGA (SEQ ID NO: 9)<br>GCACTAGGGTTTATGCTAGGAAGCT (SEQ ID NO: 10) | NM_016604.3<br>NM_016604.3 |
| KDM3C | TCTTCACCCGCACCATGAT (SEQ ID NO: 11)<br>AGACCTGCGTCGTGATGTAATG (SEQ ID NO: 12) | NM_004241.2<br>NM_004241.2 |
| KDM4A | TGCAGATGTGAATGGTACCCTCTA (SEQ ID NO: 13)<br>CACCAAGTCCAGGATTGTTCTCA (SEQ ID NO: 14) | NM_014663.2<br>NM_014663.2 |
| KDM4B | GGCCTCTTCACGCAGTACAATAT (SEQ ID NO: 15)<br>CCAGTATTTGCGTTCAAGGTCAT (SEQ ID NO: 16) | NM_015015.2<br>NM_015015.2 |
| KDM4C | GAATGCTGTCTCTGCAATTTGAGA (SEQ ID NO: 17)<br>CAACGGCGCACATGACAT (SEQ ID NO: 18) | NM_015061.2<br>NM_015061.2 |
| KDM4D | CTGGGTGTATCCTCTGCATATAGAAC (SEQ ID NO: 19)<br>GCAGAGAATGTCCTCAGTGTTTAGAA (SEQ ID NO: 20) | NM_018039.2<br>NM_018039.2 |
| KDM5A | TGTGTTGAGCCAGCGTATGG (SEQ ID NO: 21)<br>CCACCCGGTTAAAAGCAGACT (SEQ ID NO: 22) | NM_005056.2<br>NM_005056.2 |
| KDM5B | TCCATCAGCTTGTGACCATCAT (SEQ ID NO: 23)<br>GTGGTAGGCTCTTGGAAATGTAATC (SEQ ID NO: 24) | NM_006618.3<br>NM_006618.3 |
| KDM5C | GAGGAGGGCTCAGGTAAGAGAGA (SEQ ID NO: 25)<br>TGGCAACAGCGAGGACAG (SEQ ID NO: 26) | NM_004187.3<br>NM_004187.3 |
| KDM5D | CAACCATGCAACTTCGAAAGAA (SEQ ID NO: 27)<br>CCCCACGGGAGCATACTTG (SEQ ID NO: 28) | NM_001653.3<br>NM_001653.3 |

TABLE 1-continued

SYBR Green Primers for Histone Lysine Demethylase Genes:

| | Forward/Reverse Primer Sequence | RefSeq# |
|---|---|---|
| KDM6A | CACAGTACCAGGCCTCCTCATT (SEQ ID NO: 29) | NM_021140.2 |
| | TCACTATCTGAGTGGTCTTTATGATGACT (SEQ ID NO: 30) | NM_021140.2 |
| KDM6B | CGGAGACACGGGTGATGATT (SEQ ID NO: 31) | NM_001080424.1 |
| | CAGTCCTTTCACAGCCAATTCC (SEQ ID NO: 32) | NM_001080424.1 |
| KDM7A | GTCCATGGGAAGAGGACATCTT (SEQ ID NO:33) | NM_030647.1 |
| | GATCATTATCTTTCGCTCTCCATTC (SEQ ID NO: 34) | NM_030647.1 |
| JARID2 | TGTTCACAACGGGCATGTTT (SEQ ID NO: 35) | NM_004973.2 |
| | TTGTGTTTTTGAACAGGTTCCTTCT (SEQ ID NO: 36) | NM_004973.2 |

Radiosensitization Methods

20. Cell Lines

Human NSCLCs cell lines A549, H23, H1299, H1395, H1650, H2228, HCC95, HCC1195, HCC1719, HCC2279, HCC4017 and the immortalized non-cancerous Human bronchial epithelial cells (HBEC30KT), were kindly provided by Dr John D. Minna at University of Texas Southwestern Medical Center, Dallas, Tex. Cancer cell lines were maintained in RPMI media with 5% fetal bovine serum and HBEC30KT cells were cultured in KSFM media with EGF and pituitary extract (KSFM supplements from Gibco) in a humidified 37° C. incubator with 5% C02. All cell lines were routinely tested for *mycoplasma* and fingerprinted.

21. Antibodies

Anti-phospho-Histone γH2AX (Ser139), anti-Tri-Methyl-Histone H3 (Lys9) and anti-Tri-Methyl-Histone H3 (Lys4) antibodies were from Millipore; 53BP1 antibody was from Cell Signaling Technology, Inc.; Anti-Rad51 and anti-DNAPKc p-T2609 antibodies were obtained from Abcam. Fluorescent dye-conjugated secondary antibodies were obtained from Invitrogen Corp and IRDye-conjugated secondary antibodies from LI-COR Biosciences.

22. Colony Formation Assays

Clonogenic cell survival of cells treated with JIB-04, a pan-inhibitor of the Jumonji demethylase superfamily or GSKJ-4 a specific inhibitor GSK-J4 of the H3K27me3/me2-demethylases JMJD3/KDM6B and UTX/KDM6A alone or in combination with IR were analyzed by means of standard colony formation assay. The Inactive Z isomer of JIB-04, GSK-J5 and DMSO were used as controls. Cells were serially diluted to appropriate concentrations and plated into 60-mm dish in triplicate for 4 h. Then cells were treated with the indicated drugs, and irradiated 4 hours later with graded doses of radiation for concurrent treatment or irradiated and 4 hours later the drugs added for post-treatment. All cells were irradiated at room temperature in ambient air using a 137Cs source (Mark 1-68 irradiator, JL Shepherd & Associated). Surviving colonies were stained with crystal violet approximately 10 to 14 days later and colonies formed with more than 50 cells were counted. Clonogenic fraction of irradiated cells was normalized to the plating efficiency of unirradiated controls. The data are presented as the mean±SD. The curve $S=e^{-(\alpha D+\beta D2)}$ was fitted to the experimental data using a least square fit algorithm using the program Sigma Plot 11.0 (Systat Software, Inc.).

23. Tumor Growth Delay

H1299 NSCLC cells were injected subcutaneously (5×106 cells in 100 µL) into the right posterior leg of female athymic nude mice (nu/nu, 5-6 weeks old). Treatment was initiated when the subcutaneous tumors reached an average size of 150 to 200 mm³. Mice were treated with JIB-04 (50 mg/kg/day) by oral gavage or with vehicle (12.5% Cremophor EL, 12.5% DMSO as an aqueous suspension) as control; radiation was administered 4 hours after treatment. The treatment regimen consisted of a total of 12 doses of drug and/or ionizing radiation given every other day. Tumor growth delay and the dose enhancement factor were then determined. Body weight and general health were monitored every other day during the drug-treatment period and afterward. Standard survival criteria was applied to ensure animals including severe lethargy, 20% weight loss, tumor burden >2,000 mm³ and difficulty breathing. Survival data was analyzed using GraphPad Prism software. Animal experiments were carried out under approved IACUC protocols and followed UTSW animal care procedures.

24. Immunofluorescence Staining

NSCLCs were seeded onto Lab-Tek II Chamber Slides (Thermo Fisher) and 24 hours later pretreated with JIB-04 or DMSO for 4 h. Then cells were exposed to a total dose of 2 Gy (γH2AX and 53BP1) or 10 Gy (RAD-51 and DNAPKcs p-T2609) radiation. For knockdown and overexpression experiments H1299 cells were transfected using the Amaxa Nucleofector; program X-005. Specifically, 3×10⁶ were transfected with siRNA duplexes targeting JMJD2A, JMJD2B, Jarid1A, Jarid1b, scrambled siRNA (250 nM final concentration) or expression vectors pCMVHA-JMJD2A, pCMVHA-JMJD2B, pCMVHA-Jarid1A, pCMVHA-Jarid1B, PC-2 for 72 hours, followed by quantification of expression or irradiation. Then, cells were fixed in 4% formaldehyde/PBS for 15 min, permeabilized with 0.5% Triton X-100 for 15 min on ice, and blocked with 5% bovine serum albumin in PBS for 1 h. The slides were incubated with an antibody against phospho-Histone γH2AX (1:1000, 3 h at room temperature), 53BP1 (1:500, 3 h at room temperature), Rad-51 (1:500, 48 hs 4° C.) or DNAPKcs p-T2609 (1:500, 48 hs 4° C.). Alexa Fluor 488-conjugated goat anti-Rabbit, Alexa Fluor 455-conjugated goat anti-mouse or rhodamine red-conjugated goat anti-mouse secondaries antibodies were used (1:1000, 1 h at room temperature). Slides were mounted in a Vectashield mounting medium containing 4′,6-diamidino-2-phenylindole (DAPI). Cells were analyzed on a Zeiss upright fluorescent microscope.

25. Green Fluorescent Protein NHEJ and HR Assay

The green fluorescent protein assay was performed as described by Seluanov et al. To generate reporter cell lines 2 million H1299 cells were transfected with 0.5 µg of linearized NHEJ-I, or HR reporter constructs using the Amaxa Nucleofector; program X-005. G418, at 1 mg/ml, was added to the media 1 day post-transfection. Then Transient expression of the I-SceI endonuclease was used to generate a DNA DSB at the integrated GFP gene sequences. Briefly, H1299 cells containing the NHEJ or the HR constructs treated by 4 h with JIB-04 or DMSO were transfected with the pCMV3xnls-I-SceI (5 μg, functional endonuclease) and a pN1-mCherry plasmid (0.05 μg) as transfection control as previously stated. For the analysis of NHEJ and HR cells were harvested, resuspended in ~1 ml 1×PBS, put on ice, and run on a BD FACScan instrument. GFP and mCherry fluorescence was analyzed using FlowJo software. Red-versus-green was plotted and DNA repair efficiency was calculated from the number of GFP-positive cells divided by the number of cells mCherry-positive cells.

26. Cell Cycle Analysis

NSCLCs were seeded in 6 wells plate, 24 h latter cells were pretreated with JIB-04 or DMSO for 4 h and exposed to a total dose of 2 Gy. Then cells were collected and fixed using 75% ethanol at ~20° C. for at least 24 hours. The cells were resuspended with PBS and incubated with 20 μl 1 mg/ml RNase A (Sigma) and 25 μg ml/ml propidium iodide (Sigma) for 30 min at room temperature. Experiment was done by triplicate, 20,000 cells were counted and the proportion of cells of different phase was analyzed using the software Flowjo.

27. Histone Demethylase Activity

For Histone demethylase activity determination $2\times10^6$ H1299 cells were seeded in P150 plates. After 24 h cells were pretreated with JIB-04 or DMSO for 4 h, irradiated with a total dose of 8 Gy of radiation. Then cells were sonicated (3×4 sec) and equal amounts of protein were incubated with a histone H3K4me3 or H3K9me3 substrate in a reaction buffer containing cofactors for 1 h at 37° C. Finally specific immune-detection of the H3K4me2 or H3K9me2 product using the Epigentek kit P-3081 for H3K9me3 demethylation and P-3083 for H3K4me3 demethylation. Background readings were given by heat inactivated extracts.

28. Immunoprecipitation

For Histone demethylase activity determination $10\times10^6$ H1299 cells were seeded in P150 plates. Next day cells were preincubated with JIB-04 for 4 h and then irradiated with 20 Gy. Media was removed from cells, washed with PBS and fixed with 3% w/v PFA, 2% w/v sucrose in PBS for 1 min. Then cells were washed, scraped into media, pelleted by centrifugation (at 500 g for 2 min) and washed with Phosphatase inhibitor 1×, 1 μM Wortmannin (WM) and protease inhibitors 1× (Sigma). Cell pellets were re-suspended in 2.5× the packed cell volume (PCV) of Nucleosome Preparation Buffer (NPB, 10 mM HEPES [pH 7.9], 10 mM KCl, 1.0 mM $CaCl_2$, 1.5 mM $MgCl_2$, 0.34 M sucrose, 10% glycerol, 1 mM DTT, 0.1% Triton X-100) containing Phosphatase inhibitor, 1 μM Wortmannin (WM) and protease inhibitors (Sigma) and 100 U ml-1 micrococcal nuclease (MNase) and incubated at 370 C for 45 min (note: WM is required to block in vitro DNA-PK/ATM activation by MNase-produced DSBs). An equal volume of Nucleosome Solubilization Buffer (NSB=Nucleosome preparation buffer+2% [v/v] NP-40, 2% [v/v] Triton X-100, 600 mM NaCl) was then added. Samples were then vortexed, sonicated briefly and centrifuged at 10,000 rpm for 10 min. The resulting supernatants were incubated with 2 μl of anti-gH2AX monoclonal antibody for overnight at 40 C with rotation. Immunocomplexes were pulled down by adding 45 μl of protein G-sepharose for 3 h at 40° C., washed three times with wash buffer (1×NPB+1×NSB), resuspended in 2×SDS sample buffer and incubated at >70° C. for 2 h (to reverse cross-links). Protein levels on samples were quantified and equal amounts of protein run on 4-12% SDS acrylamide gels. Protein was transferred to nitrocellulose membranes and blotted for phospho-Histone γH2AX (Ser139), Tri-Methyl-Histone H3 (Lys9) and Tri-Methyl-Histone H3 (Lys4). IRDye 680RD and IRDye 800 CW (LI-COR Biosciences) secondary antibodies were used and images were captured with the Odyssey infrared imaging system. Quantification was done using the using ImageJ software (National Institute of Health, NIH)

29. Statistical Analyses

Unpaired 2-sided Student's t test, one-way analysis of variance following by post tests or Kruskal-Wallis and Dunn's post-tests (GraphPad Prism Software) were used for statistical analyses. Clonogenic survival curves were modeled with the linear quadratic equation ($S=e^{-[\alpha D+\beta D2]}$) for radiation treatment and a four-parameter variable slope regression for drug toxicity. Differences with p values lower than 0.05 were considered as statistically significant.

Example 2

Long-Term Paclitaxel+Carboplatin Treated NSCLC Cell Lines Develop Progressive Increases in Chemoresistance To establish in vitro models of lung cancer chemoresistance, NSCLC cell lines were treated with paclitaxel+carboplatin standard chemotherapy combination given in a clinically relevant 2:3 taxane-platin ratio. Our ongoing tests of >100 NSCLC lines identified NCI-H1299 and NCI-H1355 among a group of NSCLC cell lines that were 100-500 fold more sensitive (had lower $IC_{50}$ values) in 5 day MTS assays, than the most resistant NSCLC lines, and were thus selected as "parental" cells to develop drug resistant variants. Clinical annotations and driver oncogenotypes for these cell lines are listed in Tables 2 and 3.NCI-H1299 and NCI-H1355 cells were treated long-term for >6 months with increasing doses of paclitaxel+carboplatin doublet. Treatment was given in cycles of drug on (4 days)/drug off (1-2 weeks). Cells were characterized intermittently for their platin-taxane drug response phenotypes after different treatment cycles, with T[n] denoting cell line variant developed after 'n' cycles of doublet therapy. H1299 isogenic variant series were thus developed consisting of T5, T10, T15 and T18, and H1355 isogenic cell line series with T4, T8, T13 and T16 resistant variants. These long-term treated variants showed progressive increase in resistance to paclitaxel+carboplatin with increasing treatment cycles (FIGS. 1A, 1C), reaching ~53-fold and ~79-fold increases in $IC_{50}$ in H1299 T18 and H1355 T16, respectively (FIGS. 1B, 1D). Drug resistance was also validated in liquid colony formation assays involving continuous exposure over 2-3 weeks to paclitaxel+carboplatin combination treatment (FIGS. 1E-1H).

TABLE 2

Figures 11A, 11B, 11C, 11D, 11E, 11F, 11G, 11H:
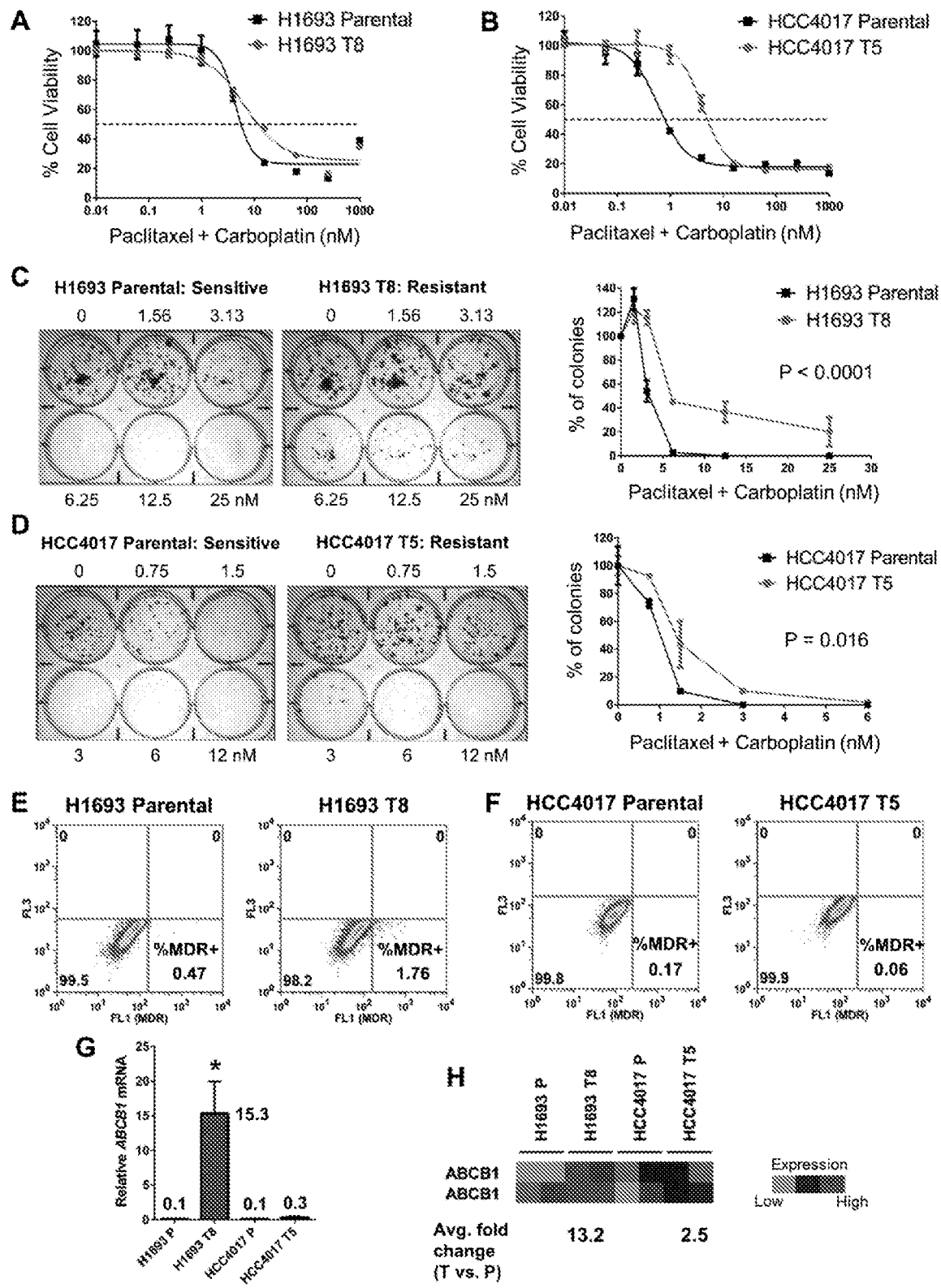
FIGS. 11A-11H. H1693 T8 and HCC4017 T5 cell line variants exhibit paclitaxel+carboplatin resistance, but HCC4017 T5 cells do not show increased MDR1 expression.

Clinical annotations of NSCLC cell lines; Related to FIGS. 1, 11.

| NSCLC Cell Line | NSCLC Subtype | Stage | Age | Race | Gender | Smoking Pack Years (PY) |
|---|---|---|---|---|---|---|
| NCI-H1299 | Large Cell Carcinoma | IIIA | 43 | Caucasian | M | 50 |
| NCI-H1355 | Adeno-carcinoma | IV | 53 | Caucasian | M | 100 |
| NCI-H1693 | Adeno-carcinoma | IIIB | 55 | Caucasian | F | 80 |
| HCC4017 | Large Cell Carcinoma | IA | 62 | Caucasian | F | Ex-smoker (76 PY) |

TABLE 3

Oncogenotypes of NSCLC cell lines; Related to FIGS. 1, 11.

| Cell Line | TP53 | KRAS | NRAS | LKB1 | EGFR |
|---|---|---|---|---|---|
| NCI-H1299 | HD | WT | Mutant | WT | WT |
| NCI-H1355 | Mutant | Mutant | WT | Mutant | WT |
| NCI-H1693 | Mutant | WT | WT | WT | WT |
| HCC4017 | Mutant | Mutant | WT | WT | WT |

WT = wild-type,
HD = homozygous deletion

Example 3

Figures 2A, 2B, 2C, 2D, 2E, 2F, 2G, 2H:
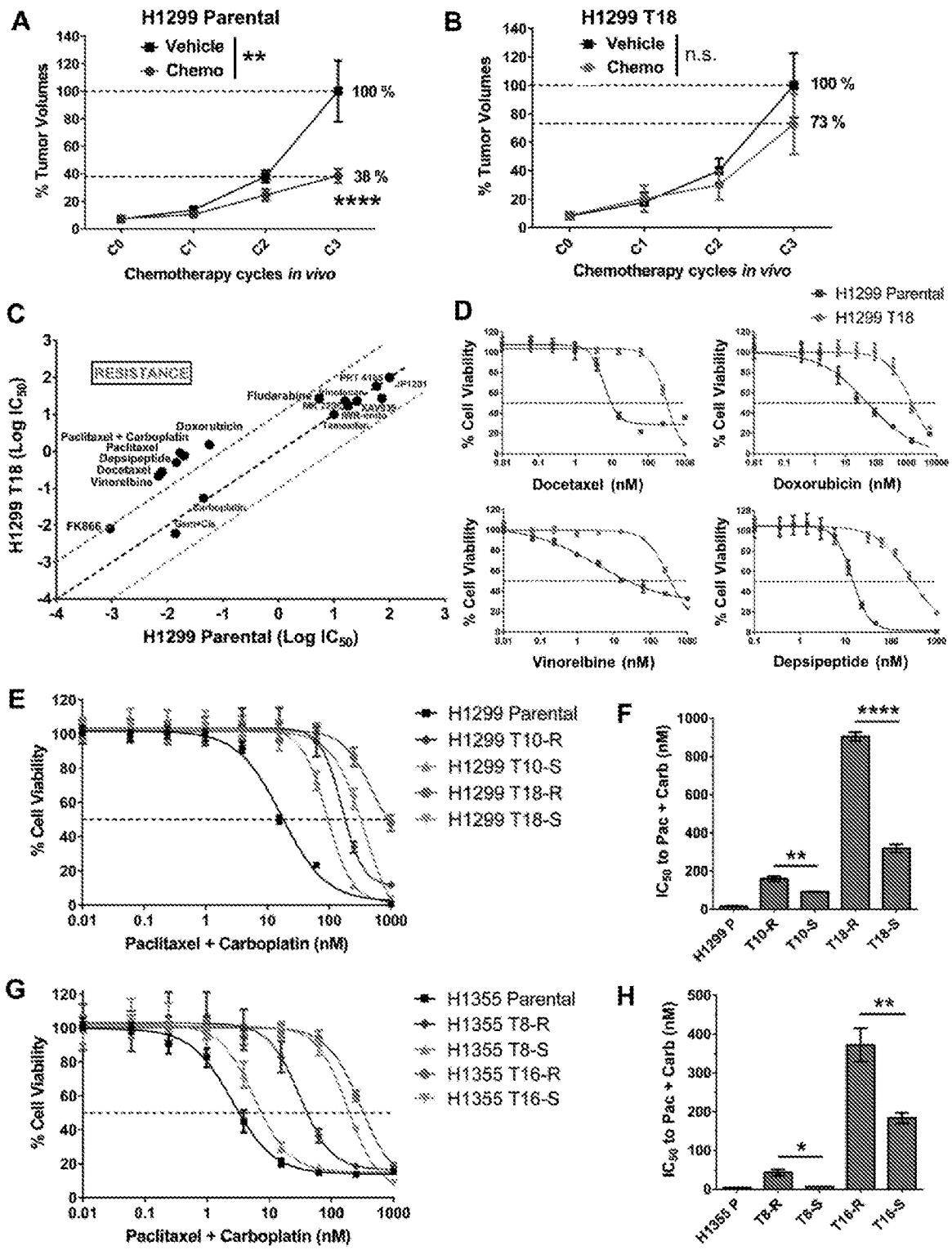
FIGS. 2A-2H. Paclitaxel+carboplatin resistant variants exhibit cross-resistance and display partial reversibility in resistance upon extended drug-free culturing.

Resistant Cell Line Variants Show Decreased Response to Taxane+Platin Chemotherapy In Vivo, Cross-Resistance to Multiple Drugs In Vitro, and Partial Reversal of Chemoresistance Upon Extended Drug-Free Culturing To validate the taxane-platin resistance phenotype in vivo, subcutaneous xenografts of H1299 parental and H1299 T18 cells were developed and treated the tumor bearing mice with 3 cycles of taxane+platin chemotherapy. While H1299 parental xenografts treated with docetaxel+cisplatin therapy showed a dramatic reduction in tumor burden compared to the vehicle-treated group (two-way ANOVA, **P=0.002), H1299 T18 tumors showed a non-significant response, confirming resistance (FIGS. 2A-2B). This also confirmed the presumption that the tumors were cross-resistant to docetaxel+cisplatin standard therapy (drugs that are functionally equivalent to paclitaxel+carboplatin).

Figures 9A, 9B, 9C, 9D, 9E:
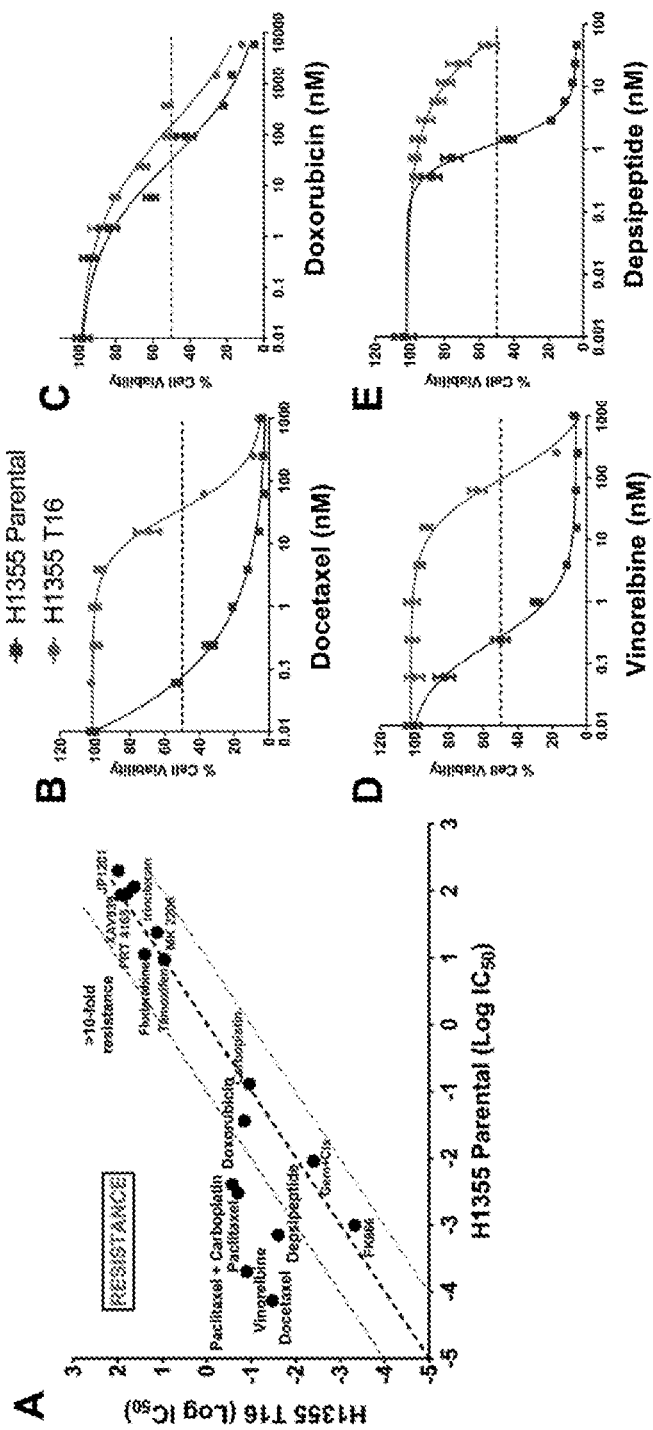
FIGS. 9A-9E. H1355 T16 paclitaxel+carboplatin resistant cell line shows multi-drug resistance phenotype.
Figures 10A, 10B, 10C, 10D, 10E, 10F, 10G, 10H:
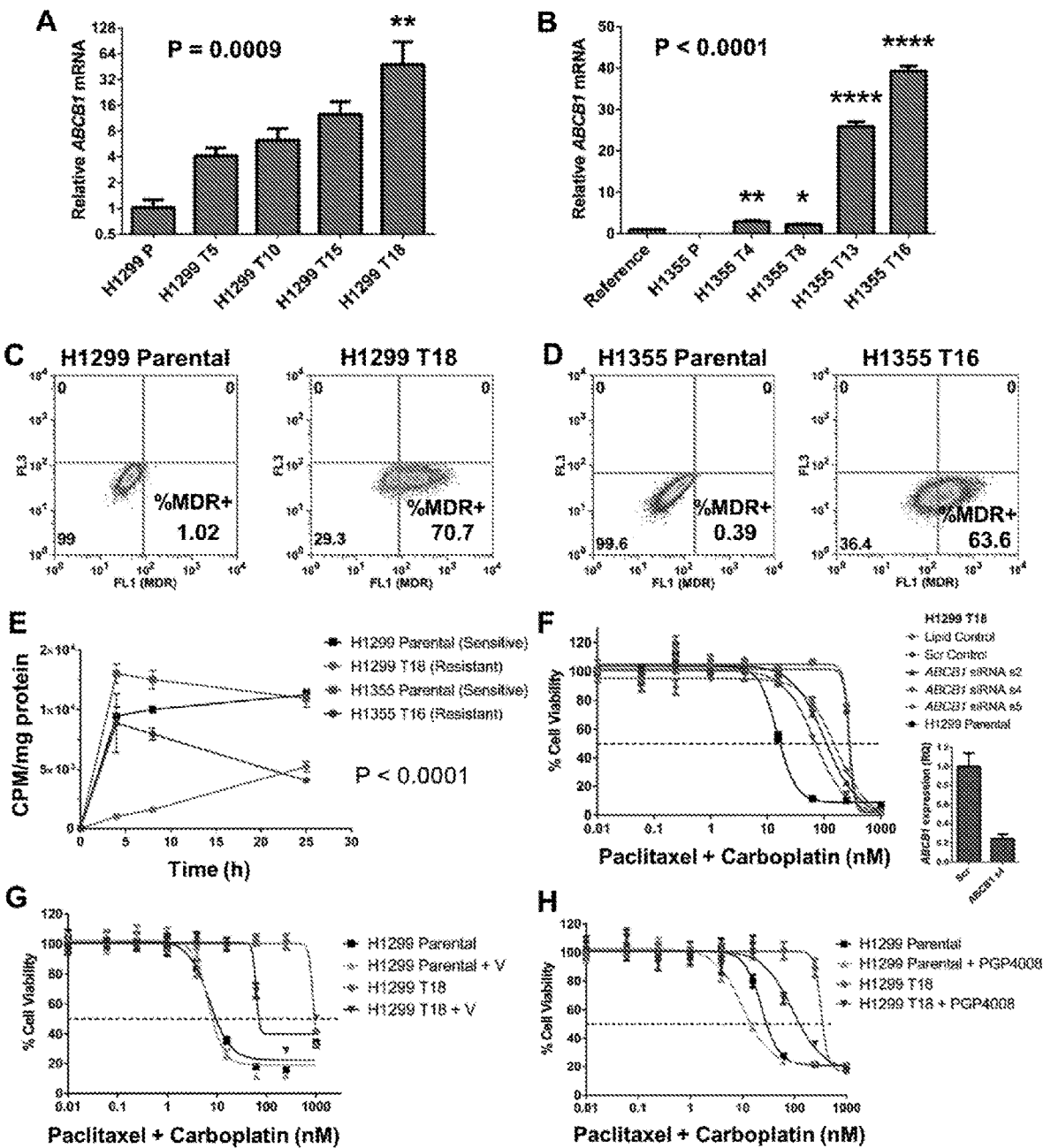
FIGS. 10A-10H. Chemoresistant cells express ABCB1/MDR1 drug transporter and show partial reversal of resistance upon MDR1 inhibition.

Consistent with previously published reports that suggested the involvement of MDR1 in taxane resistance (Lemontt et al., 1988; Roninson et al., 1986), increased mRNA and protein expression of MDR1/PgP/ABCB1 were detected in both H1299 and H1355 resistant variants (FIGS. 10A-10D). To characterize the multi-drug resistance phenotype, several standard and targeted chemotherapeutic agents were tested (FIG. 2C). Resistant variants were found to be cross-resistant to docetaxel, doxorubicin, vinorelbine and depsipeptide which are known MDR1 substrates (FIGS. 2D, 9). As expected, MDR1 expression in resistant variants corresponded with reduced intracellular docetaxel accumulation (FIG. 10E). However, MDR1/ABCB1 siRNA knockdown in H1299 T18 cells only partially reversed taxane-platin resistance (FIG. 10F). Also, pharmacological inhibition of MDR transporter using verapamil or PGP4008 showed incomplete reversal of drug resistance (FIGS. 10G-10H), suggesting collateral non-MDR1 mediated resistance mechanisms. Furthermore, when the panel of drug resistant NSCLC cell line models by long-term paclitaxel+carboplatin treatment of sensitive NCI-H1693 and HCC4017 cell lines was expanded, it was found that both cell lines exhibited development of taxane-platin resistance (FIGS. 11A-11D), but HCC4017 T5 resistant variant did not show increased MDR1 mRNA or protein expression (FIGS. 11E-11H). These findings led to further investigation of non-MDR phenotypic and molecular changes in taxane-platin resistant NSCLC variants. Among these was the observation that extended drug-free culturing of H1299 and H1355 chemo-resistant cell lines for >4 months resulted in partial reversal of resistance, as indicated by the shift in drug response curves (FIG. 2E, 2G) and significant decrease in IC50 values (FIG. 2F, 2H).

Example 4

Figures 3A, 3B, 3C, 3D, 3E, 3F:
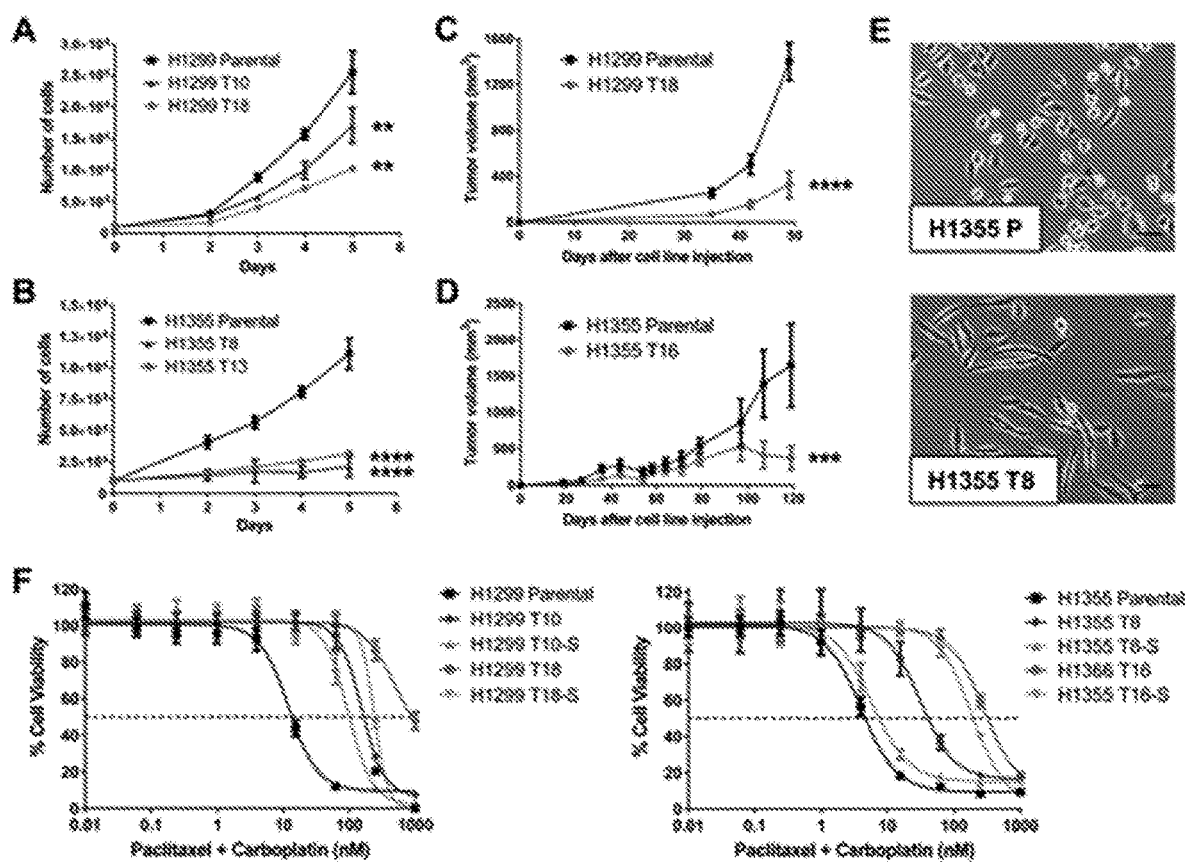
FIGS. 3A-3F. Resistant variants show several phenotypical alterations and exhibit reversible drug resistance.

Resistant Cells Exhibit Several Phenotypic Alterations and Reversible Drug Resistance Both H1299 and H1355 drug resistant variants showed slower cell growth in vitro compared to parental cells (FIGS. 3A-3B). To test if this difference persisted in vivo, equal number of parental and resistant cells were injected subcutaneously in NOD/SCID mice and monitored tumor volumes for 2-4 months. While there was no difference in tumor take rate or histology of these xenografts, tumors from both H1299 and H1355 resistant variants grew significantly slower compared to parental tumors (FIGS. 3C-3D). Slow-cycling cells have been previously linked to evasion of response to multiple chemotherapies (Roesch et al., 2013; Stewart et al., 2007).

Figures 12A, 12B, 12C:
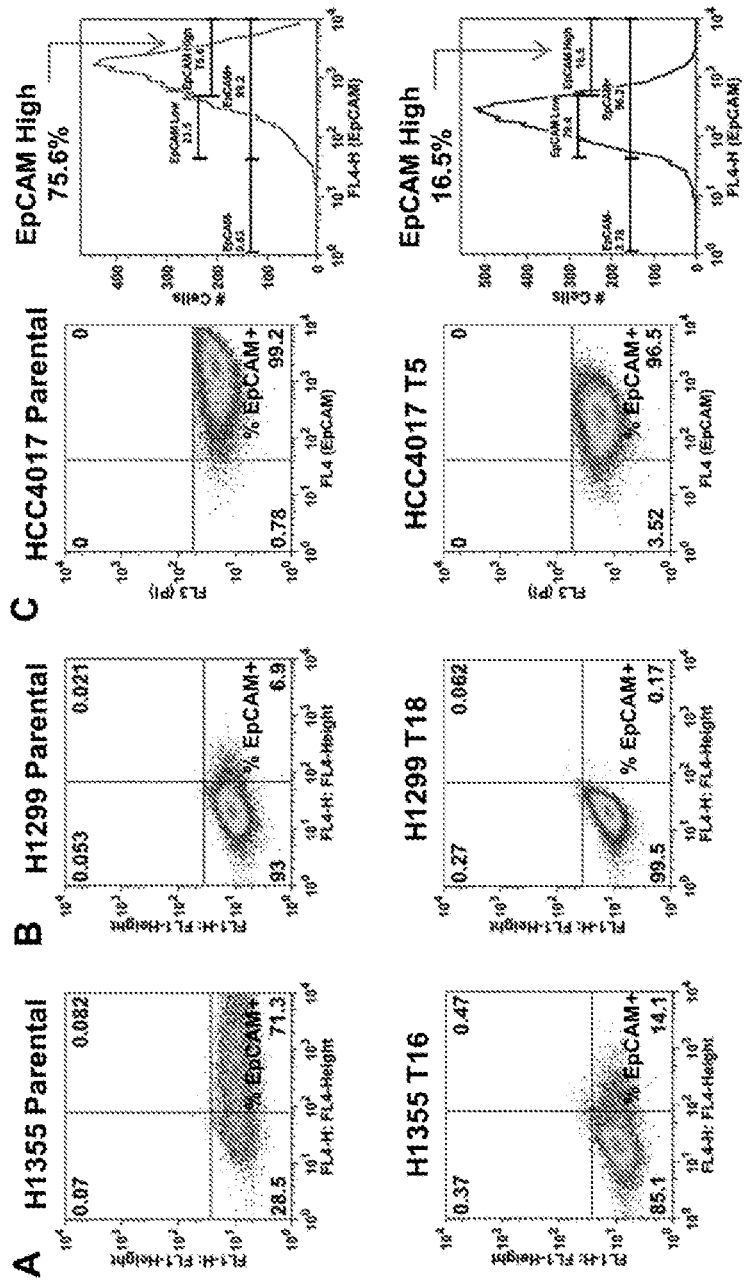
FIGS. 12A-12C. Drug resistant cell lines exhibit decrease in percentage of cells expressing the epithelial cell adhesion marker, EpCAM.

Additionally, the H1355 variant showed an epithelial-to-mesenchymal shift in morphology (EMT) and a decreased EpCAM+ population with the acquisition of drug resistance (FIGS. 3E and S4). Similarly, H1299 and HCC4017 resistant variants exhibited a significant decrease in percentage of cells expressing EpCAM (FIG. 12). EMT has been previously described in the context of resistance to EGFR TKIs (Rho et al., 2009; Thomson et al., 2005) as well as standard chemotherapies including gemcitabine, oxaliplatin and paclitaxel (Voulgari and Pintzas, 2009). Since EMT is a reversible process, these findings suggested the possibility of transient transcriptional re-wiring during development of drug resistance.

Upon drug-free culturing for >4 months, resistant variants showed a partial reversal in chemoresistance as indicated by a decrease in drug response $IC_{50}$ (FIG. 3F). Highly resistant cells (H1299 T18, H1355 T16) as well as variants with intermediate resistance (H1299 T10, H1355 T8) showed this partial reversibility. These observations were suggestive of alterations in the epigenetic landscape of drug treated cells, some of which could be lost in the absence of drug stress whereas others might be stably inherited to maintain the new altered cellular state.

Example 5

Figures 4A, 4B, 4C, 4D, 4E, 4F, 4G, 4H:
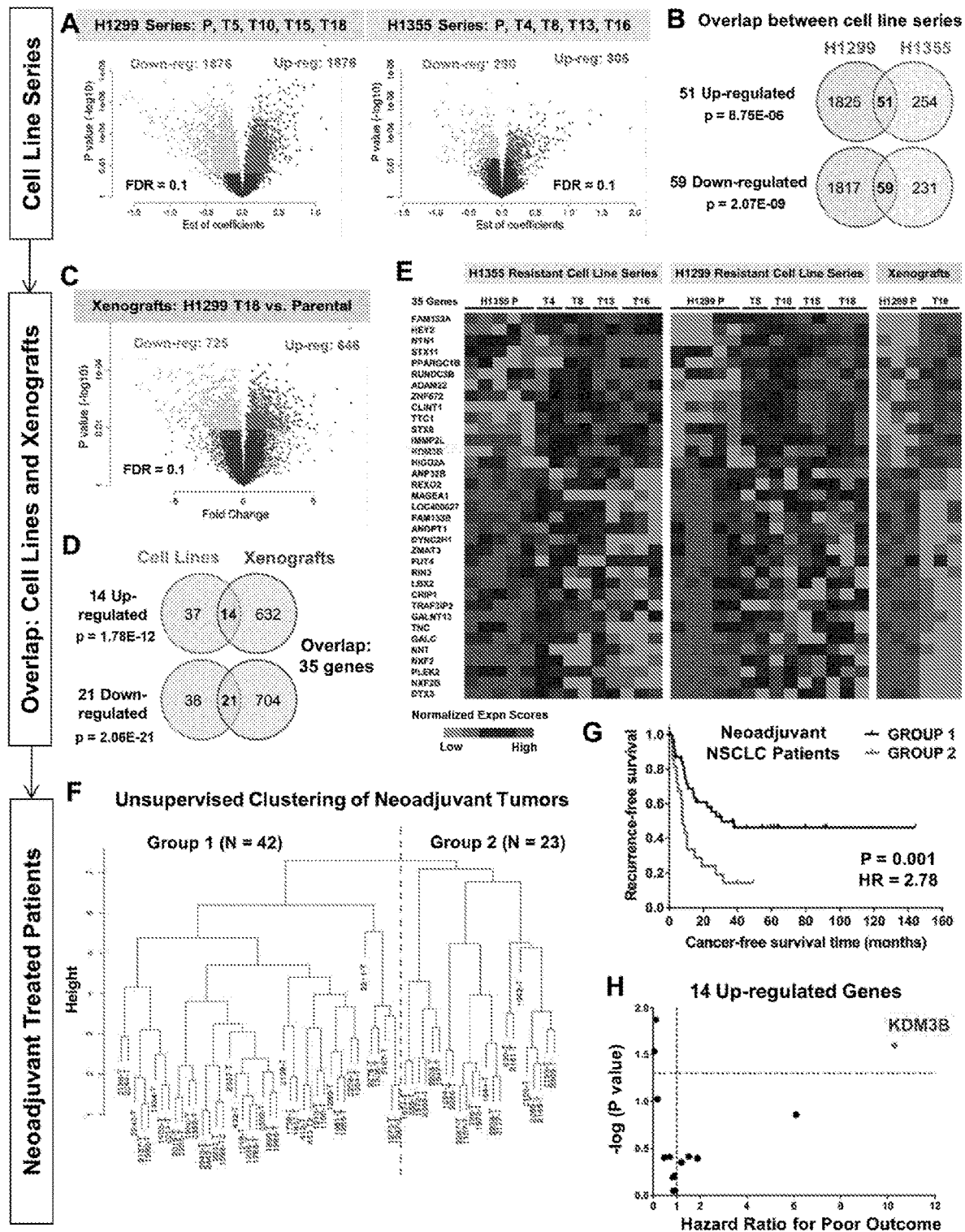
FIGS. 4A-4H. Gene signature from chemoresistant preclinical models clusters neoadjuvant treated NSCLC patients based on relapse-free outcome, and identifies KDM3B as a significant contributor to poor recurrence-free survival.

Gene Expression Profiles of Pre-Clinical Models Yield a Resistance-Associated Gene Signature To investigate the molecular changes accompanying development of NSCLC resistance to standard chemotherapy, genome-wide mRNA expression profiling was performed of progressively resistant, isogenic cell line series. A linear regression model was fitted on microarray data to systematically identify genes which showed a consistent increase or decrease in expression with increasing drug resistance represented by log transformed $IC_{50}$ values. 3752 differentially expressed genes were identified in the H1299 resistant series and 595 genes in the H1355 resistant series at a false discovery rate (FDR) of 0.1 (FIG. 4A). To obtain the most conservative identification of differentially expressed genes, it was asked which gene changes (in resistant compared to parental cells) were common between the two tumor lines and between in vitro and in vivo (xenograft) grown tumor cells. 51 up-regulated and 59 down-regulated genes overlapped between the H1299 and H1355 cell line models (FIG. 4B), while intersection with xenograft tumor expression profiles (H1299 T18 versus H1299 parental xenografts, FIG. 4C) narrowed this list to 14 up-regulated and 21 down-regulated genes whose expression changes were sustained in vivo (FIG. 4D). These 35 genes (FIG. 4E) formed the pre-clinical resistance gene signature.

Example 6

35-Gene Pre-Clinical Resistance Signature Predicted Recurrence-Free Survival in Neoadjuvant Treated NSCLC Patients and Identified KDM3B as an Important Correlate of Poor Outcome In order to evaluate clinical relevance, 35-gene resistance signature on 65 NSCLC patients who had received platin-based standard chemotherapy were tested, predominantly given as taxane+platin doublets (Table 4) prior to resection of their tumors. Resected tumor samples were expression profiled by microarrays. Using the 35-gene resistance signature, unsupervised hierarchical clustering was found to separate the 65 chemotherapy-treated patient tumors into two major groups (FIG. 4F). Kaplan-Meier survival analysis revealed that these groups showed significant differences in recurrence-free survival (FIG. 4G). Group 2 showed significantly worse cancer recurrence-free prognosis than Group 1 patients (P=0.0012, Hazard ratio=2.78; adjusted for clinical covariates, Table 5).

TABLE 4

Clinical annotations of patient tumor dataset; Related to FIG. 4 and 13.

| | Chemo-treated [a] (before surgical resection; neoadjuvant) | Chemo-naïve (at the time of surgical resection) |
|---|---|---|
| Total | 66 | 209 |
| Platin + Taxane doublet [b] | 56 | — |
| Other platin-based doublets [c] | 10 | — |
| Diagnosis | | |
| Adenocarcinoma | 31 | 152 |
| Squamous cell carcinoma | 23 | 57 |
| Other | 12 | 0 |
| Gender | | |
| Males | 36 | 112 |
| Females | 30 | 97 |
| Stage | | |
| I | 18 | 115 |
| II | 15 | 35 |
| III | 28 | 58 |
| IV | 5 | 1 |
| Smoking history | | |
| Yes | 58 | 186 |
| No | 8 | 20 |
| Unknown | 0 | 3 |
| Race | | |
| Caucasian | 59 | 185 |
| African American/Asian/Hispanic | 7 | 24 |

[a] Neoadjuvant treated patient dataset was used for evaluating 35-gene pre-clinical resistance signature. Cancer-free survival data was available for 65 out of 66 patients. Hence one sample was excluded from clustering and cancer-free survival analyses shown in FIG. 4. Annotation of excluded sample: Adenocarcinoma, Male, Stage IV, Non-smoking, and Caucasian.
[b] Carboplatin + Paclitaxel (N = 25), Cisplatin + Docetaxel (N = 24), Carboplatin + Docetaxel (N = 7).
[c] Carboplatin or Cisplatin with Etoposide/Gemcitabine/Pemetrexed/Navelbine.

TABLE 5

Cox multivariate analysis on cancer-free survival to test for bias from clinical covariates; Related to FIG. 4.

| | coef | exp(coef) | se(coef) | z | P value |
|---|---|---|---|---|---|
| Two Groups/Clusters [a] | 1.63 | 5.10 | 0.49 | 3.35 | 0.0008 |
| Histology (Squamous) | −0.23 | 0.80 | 0.50 | −0.46 | 0.64 |
| Histology (Non Sq) | 0.37 | 1.45 | 0.47 | 0.78 | 0.43 |
| Age | 0.02 | 1.02 | 0.03 | 0.88 | 0.38 |
| Smoking history (Y) | −0.93 | 0.40 | 0.67 | −1.39 | 0.16 |
| Gender (M) | −0.21 | 0.81 | 0.43 | −0.49 | 0.62 |
| Race (Asian or Pacific Islander) | −0.28 | 0.76 | 1.52 | −0.18 | 0.85 |
| Race (Caucasian) | −0.87 | 0.42 | 0.80 | −1.09 | 0.28 |
| Race (Hispanic) | −0.13 | 0.88 | 1.29 | −0.10 | 0.92 |
| Adjuvant therapy (Y) | −1.03 | 0.36 | 0.50 | −2.07 | 0.04 |
| Neoadjuvant (Pac + Carb) | 0.53 | 1.69 | 0.52 | 1.01 | 0.31 |
| Stage (II) | −0.24 | 0.79 | 0.59 | −0.40 | 0.69 |
| Stage (III) | 1.00 | 2.73 | 0.50 | 2.02 | 0.04 |
| Stage (IV) | 0.95 | 2.59 | 0.67 | 1.43 | 0.15 |

[a] Clustering of patients into two groups was the most significant contributor to the cancer-free survival difference (P = 0.0008).

To further evaluate the individual contribution of the 35 genes in the signature, Cox multivariate regression was used (Table 6). Amongst the genes that were up-regulated in pre-clinical resistance models, the gene that showed the largest hazard risk for poor recurrence-free survival outcome in neoadjuvant treated NSCLC patients was the histone lysine demethylase, KDM3B (P value=0.025, hazard ratio=10.28, FIG. 4H).

TABLE 6

Multivariate analysis of 35 gene signature towards cancer recurrence-free survival of 65 neoadjuvant treated NSCLC patients; Related to FIG. 4.

| Genes | coef | exp(coef) | se(coef) | z | P value |
|---|---|---|---|---|---|
| KDM3B [a] | 2.33 | 10.28 | 1.04 | 2.24 | 0.025 |
| ADAM22 | 1.81 | 6.10 | 1.22 | 1.48 | 0.14 |
| IMMP2L | 0.64 | 1.89 | 0.76 | 0.84 | 0.40 |
| NTN1 | 0.42 | 1.52 | 0.48 | 0.87 | 0.38 |
| FAM133A | 0.19 | 1.20 | 0.24 | 0.76 | 0.44 |
| STX11 | −0.06 | 0.94 | 0.41 | −0.15 | 0.88 |
| HEY2 | −0.11 | 0.89 | 0.23 | −0.50 | 0.62 |
| HIGD2A | −0.15 | 0.86 | 1.15 | −0.13 | 0.89 |
| RUNDC3B | −0.17 | 0.84 | 0.37 | −0.47 | 0.64 |
| PPARGC1B | −0.34 | 0.71 | 0.39 | −0.86 | 0.39 |
| TTC1 | −0.75 | 0.47 | 0.88 | −0.85 | 0.40 |
| ZNF672 | −1.72 | 0.18 | 1.03 | −1.67 | 0.094 |
| STX8 | −2.12 | 0.12 | 0.86 | −2.47 | 0.014 |
| CLINT1 | −2.99 | 0.05 | 1.37 | −2.18 | 0.029 |
| NNT [b] | 3.02 | 20.41 | 0.89 | 3.40 | 0.001 |
| NXF2B | 2.71 | 14.96 | 1.65 | 1.64 | 0.10 |
| TRAF3IP2 | 1.36 | 3.89 | 0.90 | 1.52 | 0.13 |
| DTX3 | 0.88 | 2.41 | 0.32 | 2.73 | 0.006 |
| REXO2 | 0.82 | 2.28 | 1.08 | 0.76 | 0.44 |
| LBX2 | 0.69 | 2.00 | 0.35 | 2.00 | 0.046 |
| FUT4 | 0.70 | 2.00 | 0.85 | 0.82 | 0.41 |
| GALNT13 | 0.52 | 1.68 | 0.38 | 1.37 | 0.17 |
| CRIP1 | 0.48 | 1.62 | 0.41 | 1.18 | 0.24 |
| TNC | 0.45 | 1.58 | 0.27 | 1.68 | 0.092 |
| MAGEA1 | 0.39 | 1.47 | 0.22 | 1.78 | 0.075 |
| ANGPT1 | 0.21 | 1.23 | 0.35 | 0.59 | 0.55 |
| RIN3 | 0.18 | 1.19 | 0.41 | 0.43 | 0.67 |
| GALC | 0.10 | 1.11 | 0.65 | 0.16 | 0.88 |
| PLEK2 | −0.09 | 0.92 | 0.27 | −0.32 | 0.75 |
| ZMAT3 | −0.24 | 0.78 | 0.89 | −0.27 | 0.79 |
| LOC400027 | −0.32 | 0.73 | 0.51 | −0.62 | 0.54 |
| DYNC2H1 | −0.72 | 0.48 | 0.45 | −1.61 | 0.11 |
| ANP32B | −0.80 | 0.45 | 0.76 | −1.06 | 0.29 |

TABLE 6-continued

Multivariate analysis of 35
gene signature towards cancer recurrence-free survival of 65
neoadjuvant treated NSCLC patients; Related to FIG. 4.

| Genes | coef | exp(coef) | se(coef) | z | P value |
|---|---|---|---|---|---|
| FAM133B | −1.68 | 0.19 | 1.32 | −1.27 | 0.20 |
| NXF2 | −1.96 | 0.14 | 1.31 | −1.50 | 0.13 |

[a] KDM3B was up-regulated in resistant cell lines and xenografts, and showed the most significant, positive correlation with poor cancer recurrence-free survival (expcoeff/Hazard ratio = 10.28, P value = 0.025).
[b] Though NNT expression had a high positive correlation in this multivariate analysis, it was actually down-regulated in the pre-clinical resistant models and was hence not selected for subsequent studies.

Example 7

Figures 5A, 5B, 5C, 5D, 5E, 5F, 5G:
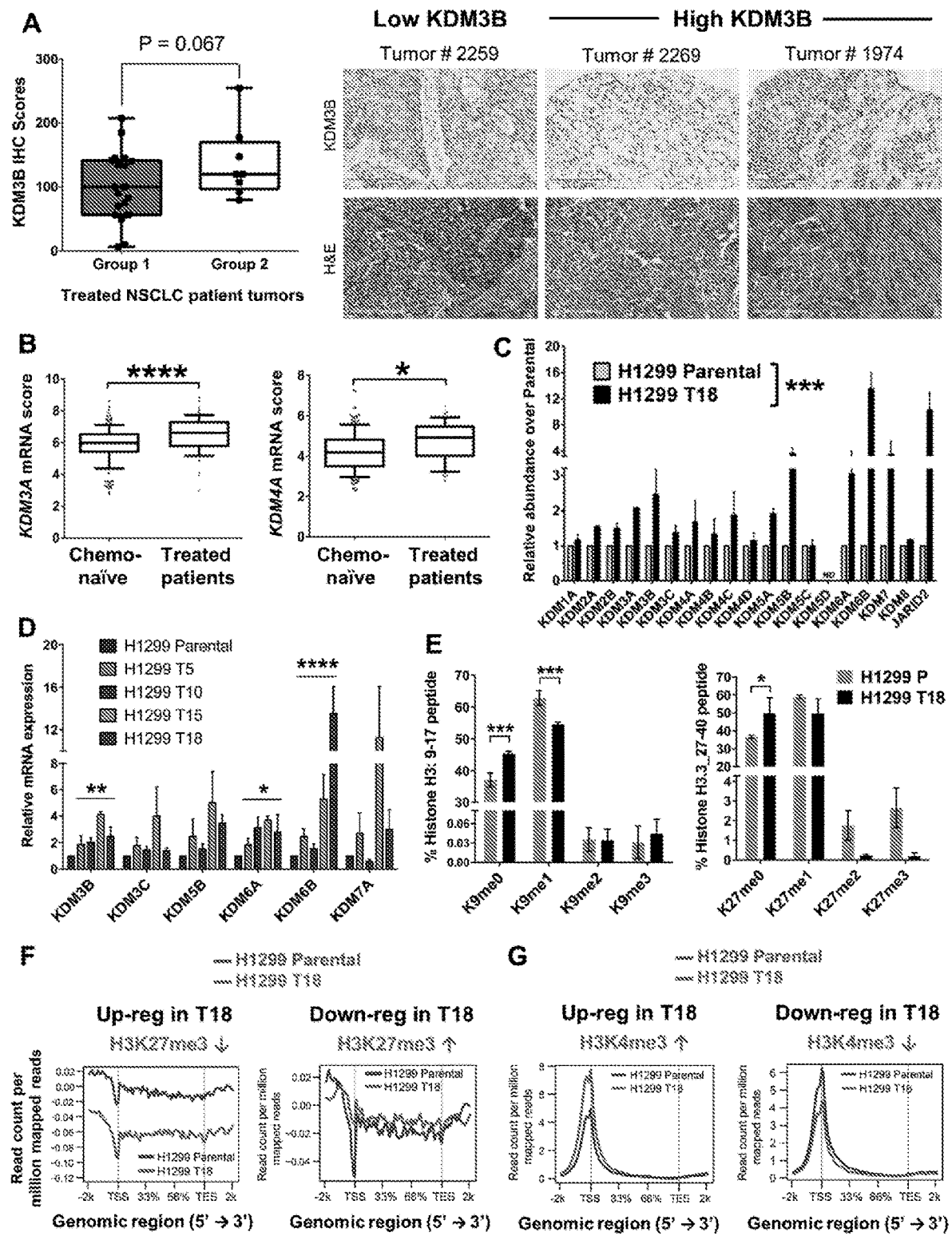
FIGS. 5A-5G. Neoadjuvant-treated NSCLC patient tumors and chemoresistant cell lines exhibit elevated expression of several histone lysine demethylases (KDMs) and altered histone methylation levels.
Figures 13A, 13B, 13C:
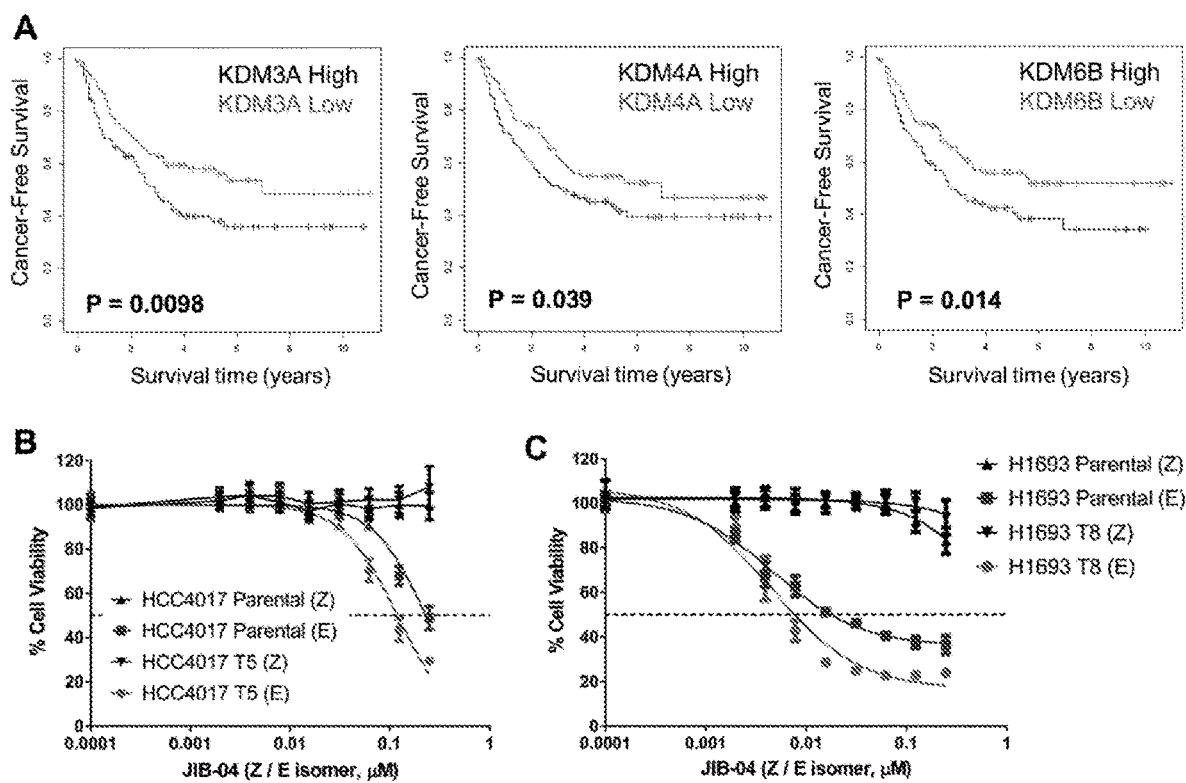
FIGS. 13A-13C. High KDM expression correlate with poor recurrence-free survival in NSCLC patients, and chemoresistant NSCLC cells show increased sensitization to KDM inhibitor JIB-04.

Chemotherapy Treated NSCLC Tumors Show Increased KDM Expression and Neoadjuvant Treated NSCLC Tumors Show Increased KDM Expression The KDM3B expression difference was first verified in chemotherapy treated patient tumors by immunohistochemistry (IHC) of tumors available in a tissue microarray format (TMA). Group 2 patients (who had poor recurrence-free survival) showed higher overall KDM3B IHC scores compared to Group 1 patients (FIG. 5A). mRNA expression was then evaluated for other members of the histone lysine demethylase (KDM) family in the patient microarray dataset. NSCLC patient tumor cells surviving standard chemotherapy showed higher overall KDM3A and KDM4A mRNA expression compared to chemo-naïve tumors (FIG. 5B). Importantly, high KDM3A, KDM4A and KDM6B mRNA expression in the entire cohort of 275 NSCLC patients (neoadjuvant treated+chemo-naïve, annotated in Table 4) correlated with significantly worse recurrence-free prognosis (FIG. 13A).

KDM3B protein levels were evaluated in the same cohort of neoadjuvant chemotherapy treated NSCLC tumors by immunohistochemistry (IHC) of specimens available in a tissue microarray format (TMA). Group 2 patients (who had poor recurrence-free survival) showed higher overall KDM3B IHC scores compared to Group 1 patients (FIG. 5A). The mRNA expression of other members of the KDM enzyme family in the NSCLC patient microarray dataset (66 neoadjuvant treated+209 chemo-naïve) was then evaluated. NSCLC patient tumor cells surviving standard neoadjuvant chemotherapy were found to express higher overall KDM3A and KDM4A mRNA levels compared to chemo-naïve tumors (FIG. 5B, P value adjusted for clinical variables by multivariate analysis).

Example 8

Resistant Cells Show Increased Expression of JumonjiC Histone Lysine Demethylases and Reduced Levels of H3K27Me3 Across Transcribed Regions of the Genome The above findings, coupled with the previously described reversible resistance phenotypes, emphasized the existence of an altered epigenetic landscape in taxane+platin resistance. Therefore histone lysine demethylase expression was measured in H1299 T18 resistant cell line compared to H1299 Parental cells and found general upregulation of several members of the JumonjiC enzyme family (FIG. 5C, Table 7). Specifically, strong upregulation of H3K27me3 demethylases was noted including KDM6A and 6B (FIG. 5C). Concomitant with these changes, overall decrease in H3K27 trimethylation across transcribed regions of the genome was observed in H1299 T18 resistant cells (FIG. 5D). The entire progressively resistant H1299 series was queried and found a consistent increase in mRNA expression of multiple Jumonji KDMs with increasing drug resistance (FIG. 5E).

TABLE 7

Fold change of mRNA expression for
histone lysine demethylase (KDM) gene family in taxane-
platin resistant NSCLC cell lines; Related to FIGS. 5.

| | Fold Change (Resistant/Parental) [a] | |
|---|---|---|
| KDM Genes | H1299 T18 | H1355 T16 |
| KDM1A | 1 | 1 |
| KDM2A | 2 | 1 |
| KDM2B | 2 | 1 |
| KDM3A | 2 | 1 |
| KDM3B | 3 | 2 |
| KDM3C | 1 | 1 |
| KDM4A | 2 | 1 |
| KDM4B | 1 | 1 |
| KDM4C | 2 | 1 |
| KDM4D | 1 | 1 |
| KDM5A | 2 | 1 |
| KDM5B | 4 | 1 |
| KDM5C | 1 | 1 |
| KDM5D | — | — |
| KDM6A | 3 | 4 |
| KDM6B | 14 | 2 |
| KDM7 | 4 | — |
| KDM8 | 1 | 1 |
| JARID2 | 10 | 1 |

[a] Expression determined by qRT-PCR; Fold changes are rounded off to the nearest digit.
— indicates expression was not detectable.

Example 9

Figures 6A, 6B, 6C, 6D, 6E, 6F, 6G, 6H:
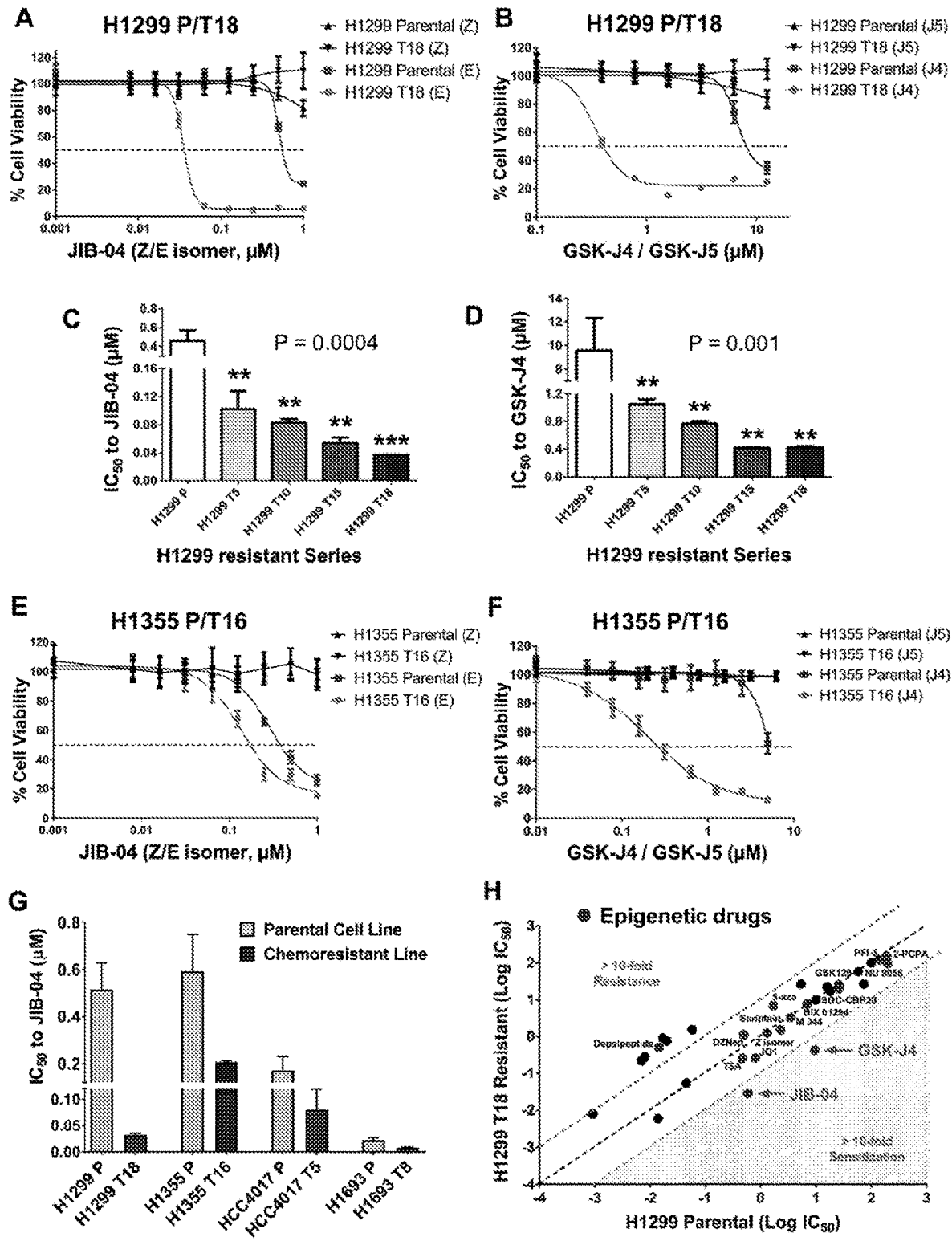
FIGS. 6A-6H. Taxane+platin chemoresistant cell lines show increased sensitivity to the JmjC KDM inhibitors JIB-04 and GSK-J4, and not to other epigenetic drugs.

Chemoresistant Cells are Hyper-Sensitized to JumonjiC Lysine Demethylase Inhibitors To test the survival dependency of chemo-resistant cells on these KDMs, a pan-JumonjiC (JmjC) histone lysine demethylase inhibitor was employed, JIB-04 (Wang et al., 2013). H1299 T18 cells were several-fold hyper-sensitized to JIB-04 compared to parental cells (FIG. 6A). By contrast, there was no viability loss in drug resistant or parental cells with the epigenetically inactive Z isomer of JIB-04. The KDM6A/KDM6B inhibitor, GSK-J4, was further tested (Kruidenier et al., 2012). Again, H1299 T18 showed higher sensitivity to GSK-J4 compared to parental cells and there was no effect on cell viability with the inactive GSK-J5 isomer (FIG. 6B).

To investigate whether increased KDM expression and pharmacological sensitivity was directly correlated with increase in drug resistance, the entire H1299 resistant series was queried. Correspondingly, a consistent decrease in $IC_{50}$ values to JIB-04 and GSK-J4 was observed as cells progressed from H1299 Parental to H1299 T18 resistant variant (FIGS. 6C-6D), suggesting a new epigenetic vulnerability, pharmacologically targetable with Jumonji inhibitors, co-develops with resistance to the chemotherapy doublet.

To explore the universality of increased sensitivity of taxane+platin chemo-resistant NSCLC cells to JmjC KDM inhibitors, other resistant cell line variants were tested.

H1355 T16 that had up-regulation of KDM genes (Table 7) showed higher sensitivity to JIB-04 (FIG. 6E) and GSK-J4 (FIG. 6F), compared to H1355 parental cell line. Overall, all tested taxane-platin resistant cell line variants including HCC4017 T5 and H1693 T8 were more sensitive to JIB-04 than parental cells (FIGS. 6G, 13B-13C).

Figures 7A, 7B, 7C, 7D, 7E, 7F, 7G, 7H:
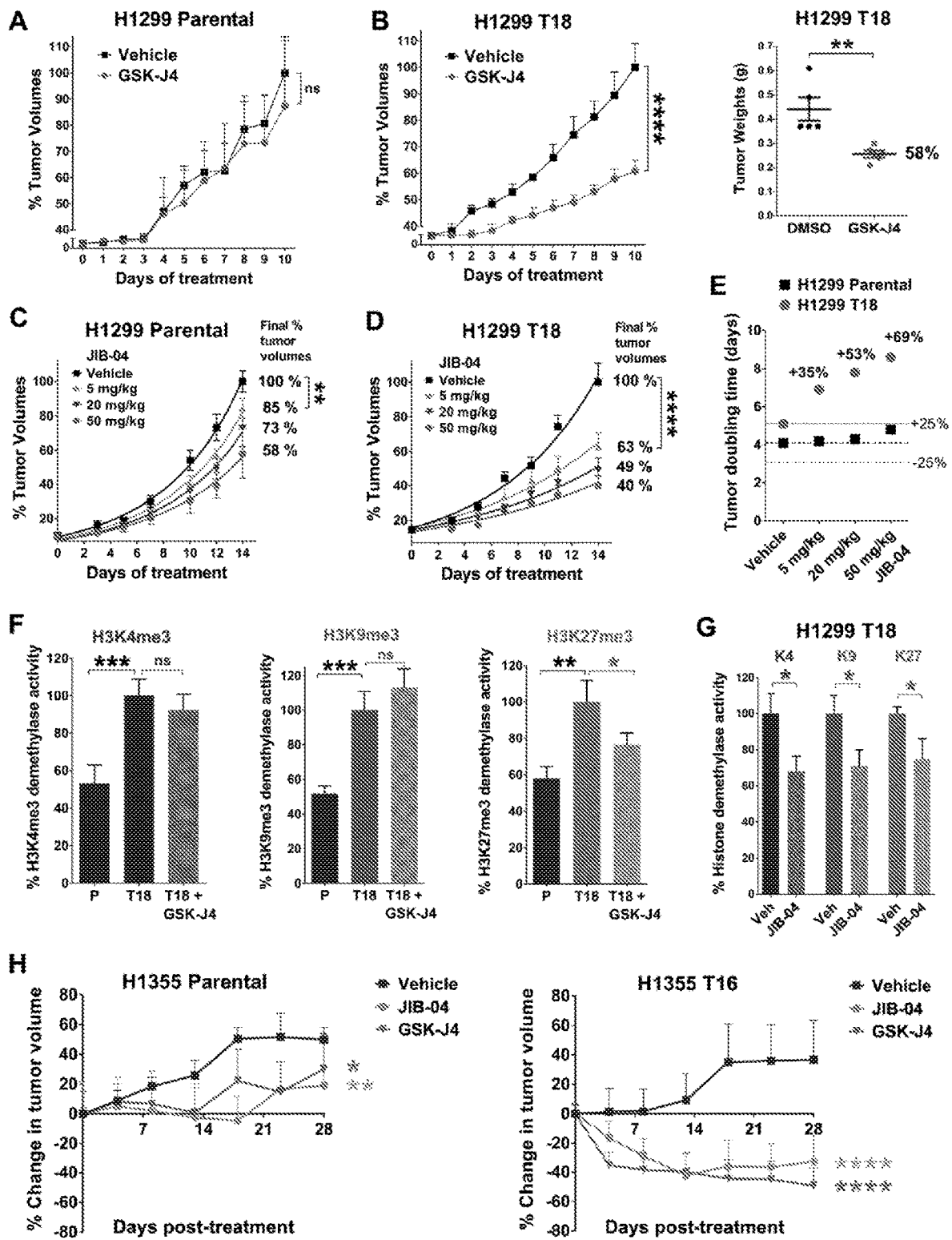
FIGS. 7A-7H. JmjC inhibitor-treated chemoresistant tumors exhibit reduced histone lysine demethylase activity and increased response to GSK-J4 and JIB-04 in vivo.
Figures 14A, 14B, 14C, 14D, 14E, 14F, 14G, 14H, 14I, 14J, 14K, 14L:
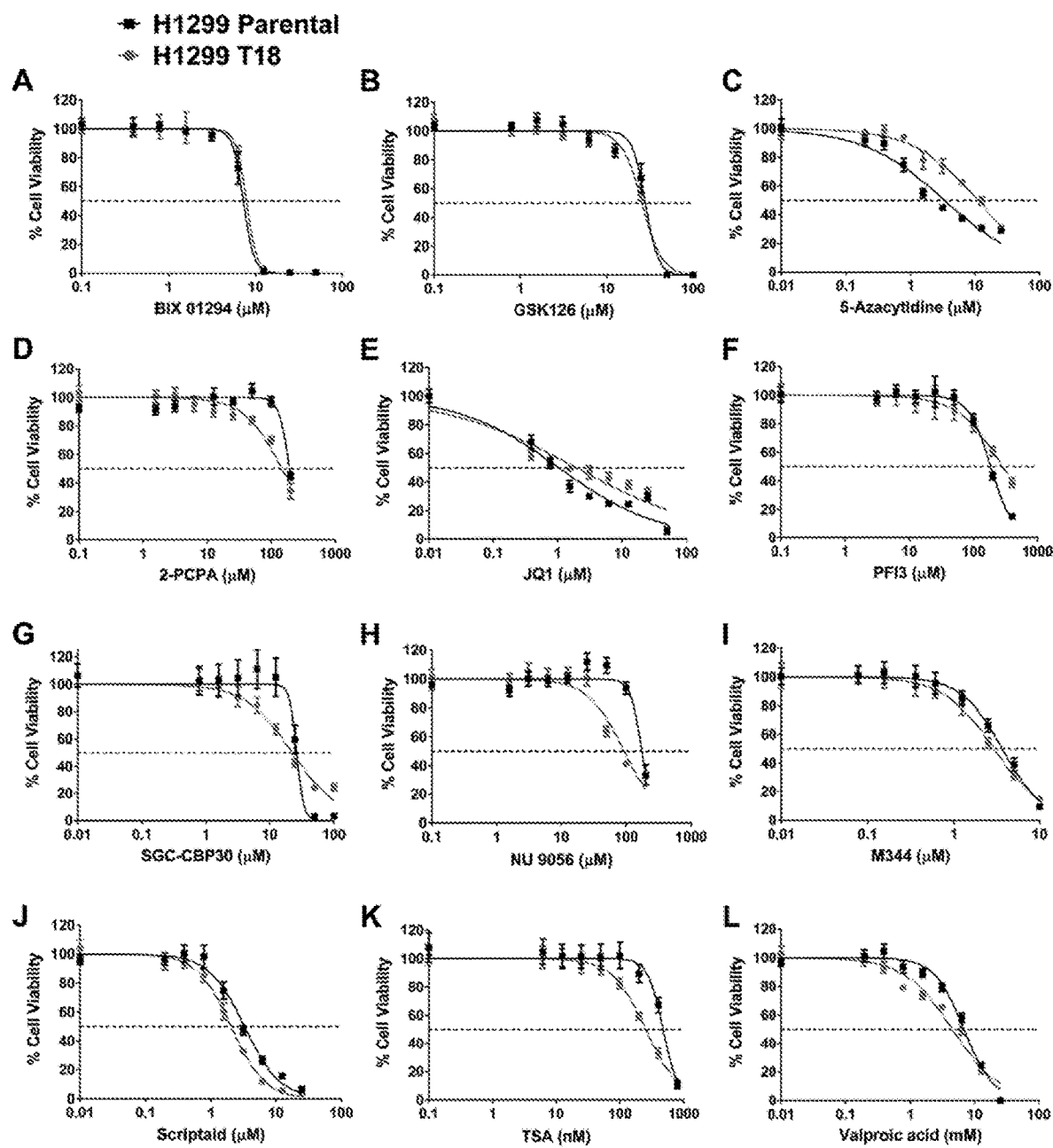
FIGS. 14A-14L. Response of H1299 T18 versus H1299 Parental to epigenetic inhibitors H1299 T18 cells did not show hyper-sensitization to other classes of epigenetic drugs: Inhibitors of HMTs (FIGS. 14A-14C), LSD1 (FIG. 14D), BRD (FIGS. 14E-14G), HATs (FIG. 14H) or HDACs (FIGS. 14I-14L).
Figures 21A, 21B, 21C, 21D, 21E:
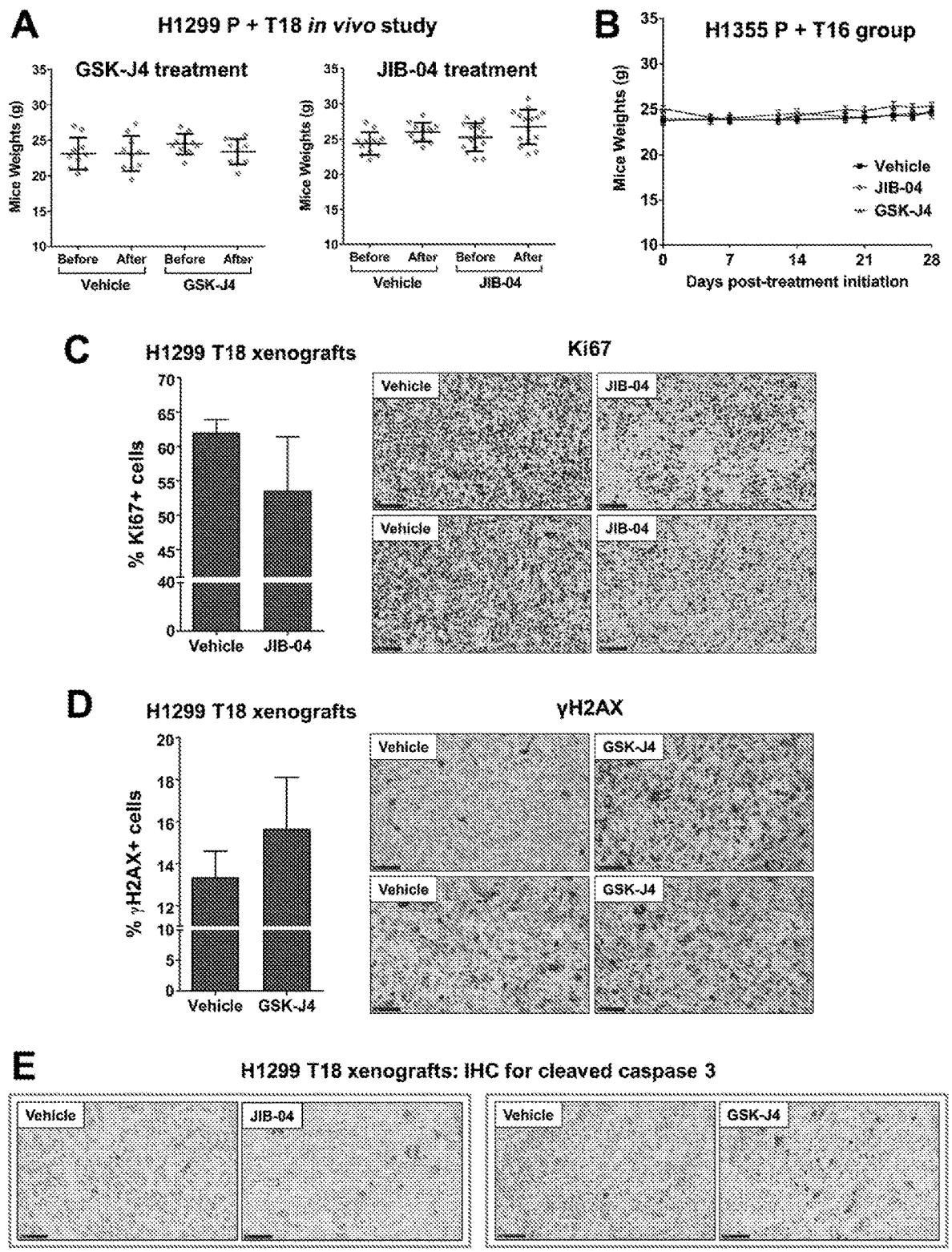
FIGS. 21A-21E. JmjC inhibitor treatment reduced cell proliferation and increased DNA damage in H1299 T18 xenografts, without causing any drug associated toxicity in mice receiving therapy.

In order to investigate whether this epigenetic vulnerability in taxane+platin chemo-resistant cells was specific to JumonjiC histone demethylase inhibitors, compounds were evaluated that target other epigenetic modifying proteins including histone methyltransferases (HMT), LSD1 demethylase, histone acetyltransferases (HAT), histone deacetylases (HDAC), DNA methyltransferases (DNMT) as well as bromodomain inhibitors. Significant differences in $IC_{50}$ between parental cells and taxane-platin resistant variants were not observed for these drugs (FIGS. 6H, 14, Table 8). These studies with JIB-04 and GSK-J4 have thus uncovered a specific, targetable epigenetic vulnerability that can be exploited therapeutically to treat NSCLCs that develop resistance to standard taxane+platin chemotherapy and potentially also intrinsically resistant tumors.

vivo, subcutaneous xenografts of H1299 Parental and H1299 T18 were established, and compared their response to GSK-J4 or JIB-04. After 10 days of treatment, GSK-J4 caused a significant reduction in average tumor volume selectively in H1299 T18 xenografts (P<0.0001) and not in H1299 Parental tumors (FIG. 7A). GSK-J4 treated T18 tumors also showed a significant decrease in final tumor weights compared to vehicle treated animals (P=0.007) whereas there was no significant drug-induced decrease in H1299 parental tumors (FIG. 7B). For the JIB-04 study, tumor bearing mice were randomized to receive 5 mg/kg, 20 mg/kg or 50 mg/kg treatment or vehicle. At all tested doses, JIB-04 resulted in greater percent reduction in final tumor volumes of H1299 T18 xenografts compared to H1299 Parental (FIG. 7C). JIB-04 treatment preferentially slowed T18 tumor growth and decreased tumor growth rate as seen by increased tumor doubling times compared to its effects on H1299 parental tumors (FIG. 7D). There was also a significant decrease in final tumor weights of 50 mg/kg JIB-04-treated H1299 T18 xenografts (P=0.045, FIG. 7E), without causing any toxicity or mice body weight loss (FIG. 21A).

TABLE 8

Selectivity Ratio (SR) of chemo-resistant cells to various standard, targeted and epigenetic therapies; Related to FIG. 6.

| Drug Class | | Drugs | H1299 T18 SR | H1355 T16 SR |
|---|---|---|---|---|
| MDR1 substrates | Taxanes | Paclitaxel + Carboplatin | 0.02 | 0.01 |
| | | Paclitaxel | 0.03 | 0.02 |
| | | Docetaxel | 0.03 | 0.002 |
| | Anthracycline | Doxorubicin | 0.04 | 0.25 |
| | Vinca alkaloid | Vinorelbine | 0.03 | 0.002 |
| | HDAC | Depsipeptide | 0.05 | 0.03 |
| Other standard and targeted chemotherapies | NAMPT | FK866 | 0.1 | 2.1 |
| | Platinum drug | Carboplatin | 0.8 | 1.2 |
| | Nucleoside metabolic + platin | Gemcitabine + Cisplatin | 2.3 | 2.3 |
| | Akt | MK-2206 | 0.7 | 1.8 |
| | SMAC mimetic | JP1201 | 1.0 | 2.0 |
| | Estrogen receptor agonist/antagonist | Tamoxifen | 1.0 | 1.0 |
| | Wnt | XAV939 | 2.7 | 1.0 |
| | Topoisomerase | Irinotecan | 1.1 | 2.7 |
| | Bmi1/Ring1A | PRT 4165 | 1.0 | 1.4 |
| Epigenetic drugs | DNMT | 5-azacytidine | 0.2 | 2.6 |
| | Bromodomain | SGC-CBP30 | 1.3 | 0.9 |
| | | JQ1 | 0.6 | 6.6 |
| | | PFI 3 | 1.1 | 2.5 |
| | HAT | NU 9056 | 2.0 | 1.0 |
| | HDAC | M344 | 1.1 | 1.8 |
| | | Valproic acid | 1.4 | 1.3 |
| | | Scriptaid | 1.5 | 1.4 |
| | | Trichostatin A | 1.8 | 2.6 |
| | HMT | BIX 01294 | 0.9 | 1.9 |
| | | DZNep | 0.5 | 1.7 |
| | | GSK 126 | 1.0 | 0.8 |
| | LSD1 | 2-PCPA | 1.3 | 1.8 |
| | JIB 04 Control | Z isomer (Inactive) | 1.1 | 1.0 |
| | JmjC KDMs | JIB-04 (E; Active) | 20.3 | 2.8 |
| | | GSK J4 | 22.3 | 10.4 |

Selectivity Ratio SR = [$IC_{50}$ of Parental]/[$IC_{50}$ of Resistant]
SR < 1 implies that variant cell lines (H1299 T18 and H1355 T16) are cross-resistant to these drugs
SR = 1 indicates no change in drug response between parental and variant cell lines
SR > 1 implies sensitization of chemo-resistant variants to these drugs; values denote fold reduction in $IC_{50}$ values Example 10

Chemoresistant Tumors Show Increased Response to GSK-J4 and JIB-04 In Vivo

To validate the sensitivity of taxane-platinchemoresistant NSCLC cells to JmjC histone demethylase inhibitors in For the JIB-04 study, tumor-bearing mice were randomized to receive 5 mg/kg, 20 mg/kg or 50 mg/kg treatment or vehicle. At all tested doses, JIB-04 resulted in greater percent reduction in final tumor volumes of H1299 T18 xenografts compared to H1299 Parental (FIGS. 7C-7D). JIB-04 treatment preferentially slowed T18 tumor growth and decreased tumor growth rate as seen by increased tumor doubling times (FIG. 7E), without any appreciable toxic effects on treated mice (FIG. 21A).

To evaluate whether the targeted KDM enzymatic activity was reduced in the JmjC inhibitor-treated tumors in vivo, the inventors measured histone demethylase activity in drug-treated and vehicle-control tumor lysates by ELISA. Chemoresistant H1299 T18 xenografts showed higher histone H3K4me3, H3K9me3 and H3K27me3 demethylase activity compared to H1299 Parental tumors (FIG. 7F), in agreement with increased KDM expression. KDM6 inhibitor GSK-J4 significantly inhibited H3K27me3 demethylase activity in H1299 T18 xenografts (FIG. 7F, right), without reducing H3K4me3 or H3K9me3 demethylase activity (FIG. 7F, left and middle panels). Pan-JmjC KDM inhibitor JIB-04 significantly inhibited H3K4me3, H3K9me3 as well as H3K27me3 demethylase activity in H1299 T18 xenografts (FIG. 7G). IHC analysis revealed that JIB-04 treatment resulted in reduction of % Ki67+ cells in T18 xenografts (FIG. 21C), suggesting decreased cell proliferation, whereas GSK-J4 increased the % γH2AX+ cells in T18 tumors (FIG. 21D), indicating increased DNA damage. JIB-04 and GSK-J4 treated tumors exhibited focally increased cleaved caspase 3 staining in some tumor regions (FIG. 21E). Altogether, the results confirmed reduction of the targeted KDM enzymatic activity with cytostatic/cytotoxic effects in JmjC inhibitor-treated chemoresistant xenografts.

The inventors then validated the hypersensitivity of chemoresistant tumors to JIB-04 and GSK-J4 in an additional in vivo model, comparing treatment response in H1355 Parental versus H1355 T16 xenografts. JmjC-inhibitor treated H1355 Parental xenografts continued to grow in volume throughout the 28 days of treatment (FIG. 7H, left), whereas drug-treated H1355 T16 tumors exhibited significant tumor shrinkage (FIG. 7H, right). No appreciable toxicity was seen in JIB-04 or GSK-J4 treated mice (FIG. 21B).

These pre-clinical studies confirm the enhanced sensitivity of taxane+platinchemoresistant tumors to JIB-04 and GSK-J4 in vivo, and provide proof-of-principle for potential use of JmjC demethylase inhibitors for targeting drug resistant NSCLCs in the clinic. Results also suggest the potential use of Jumonji inhibitors against tumors intrinsically resistant to platin/taxane chemotherapy.

Example 11

Figures 15A, 15B, 15C, 15D:
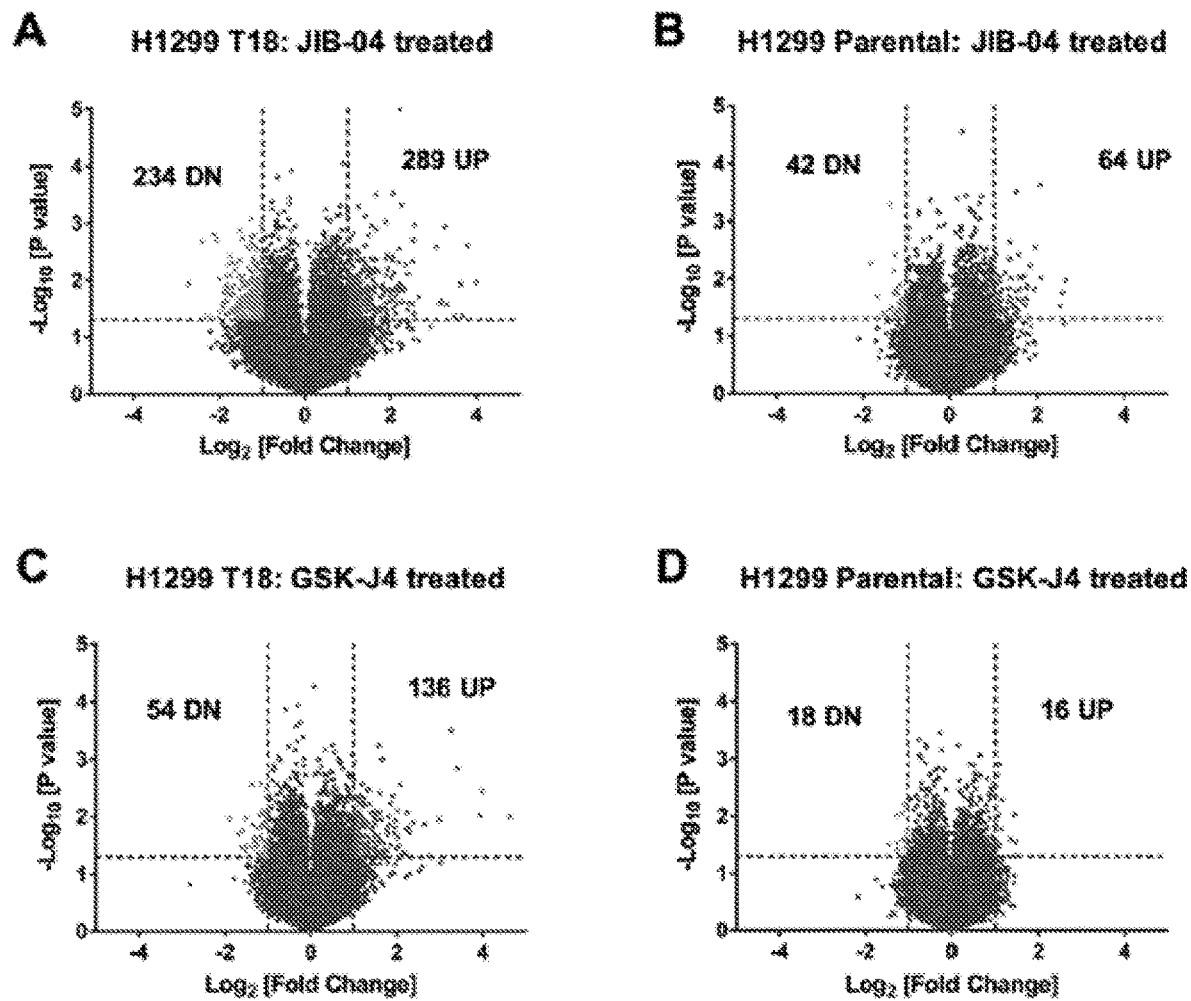
FIGS. 15A-15D.
Figures 16A, 16B:
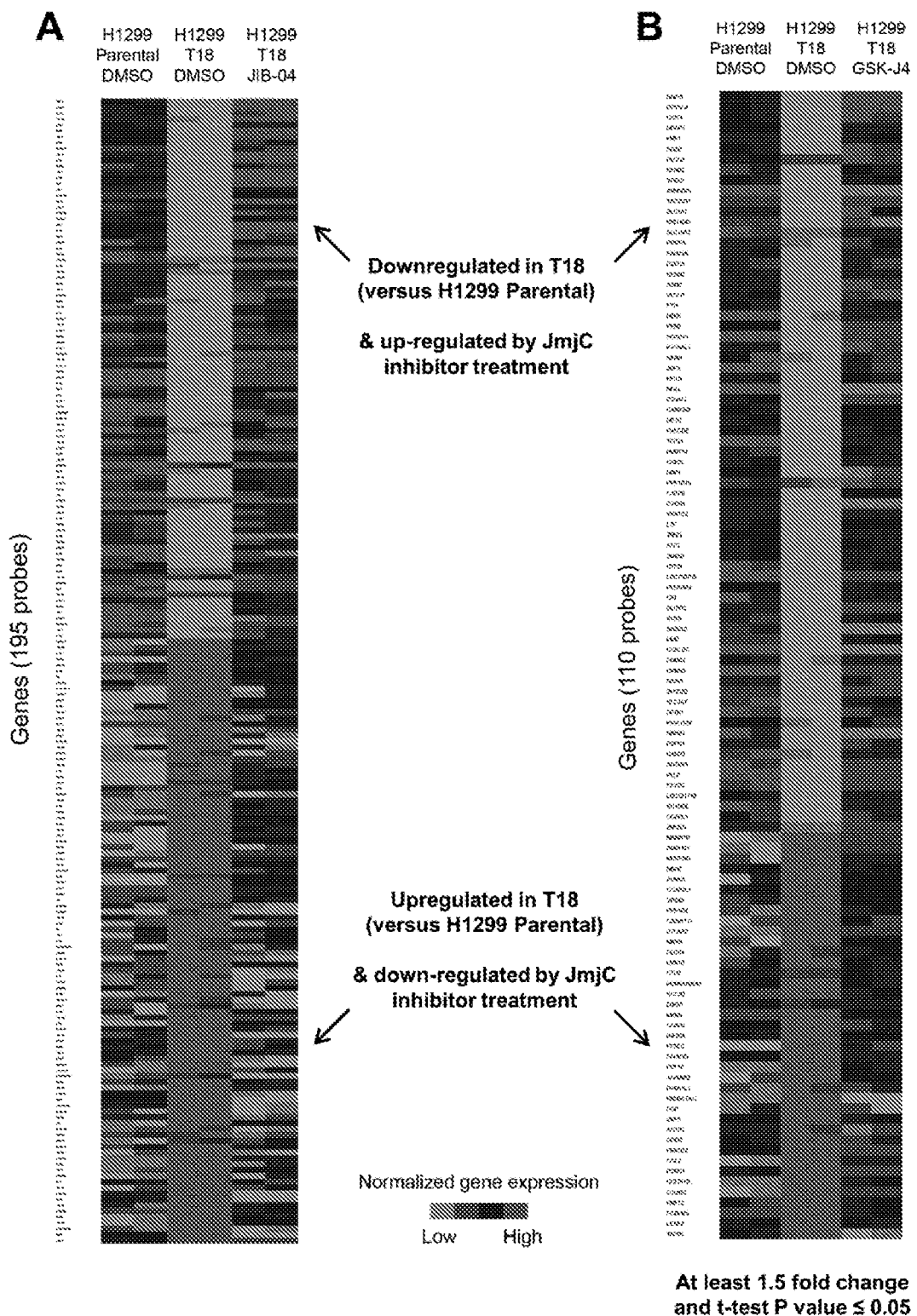
FIGS. 16A-16B.

JIB-04 or GSK-J4 Treatment Results in Reversal of Transcriptional Programs in Taxane-Platin Chemoresistant Cells In agreement with the selective killing of chemo-resistant cells with JmjC KDM inhibitors, it was observed that short-term 24 h treatment with 0.2 μM JIB-04 (FIGS. 15A-15B) or 1 μM GSK-J4 (FIGS. 15C-15D) led to gene expression changes selectively in H1299 T18 resistant cells with minimal transcriptomic changes in H1299 Parental cells (2-fold change cutoff, P value <=0.05). Importantly, JmjC inhibitor treatment of H1299 T18 caused transcriptional reprogramming and partially reversed expression changes that were seen after development of taxane-platin resistance (FIG. 16). Further, gene set enrichment analysis (GSEA) using curated gene sets from molecular signatures database (Subramanian et al., 2005) revealed a subset of transcriptional programs in H1299 T18 cells upon treatment with JmjC inhibitors, with a significant overlap between JIB-04 and GSK-J4 treatments (FIG. 17A, Venn diagram). Out of the 214 gene sets that were depleted after resistance development in H1299 T18 cells, 38 gene sets (~20%) were enriched (reversed) by both JIB-04 and GSK-J4. These 38 overlapping gene sets (Table S8) included functionally relevant categories such as genes with H3K4me3 and H3K27me3 marks (MSigDB, M1941) (Meissner et al., 2008) shown in FIG. 17A, left panel, as well as SUZ12 ChIP-on-chip targets, indicative of genes regulated by H3K27me3 (MSigDB, M9898, see Table S8) (Ben-Porath et al., 2008). Also included in the overlap were apoptotic gene sets such as MDM4 target genes, TP63 target genes and TP53 target genes. A gene set representing genes up-regulated in apoptotic tissues (MSigDB, M5681, MDM4 target genes) (Martoriati et al., 2005) enriched by both JmjC inhibitors is shown in FIG. 17A, right panel.

To gain insights into the H3K4me3 and H3K27me3 dynamics revealed by GSEA (FIG. 17A, left), the inventors performed detailed promoter bivalency analyses of the ChIP-seq data. The inventors first identified H3K4me3 and H3K27me3 bivalent gene promoters in H1299 Parental and H1299 T18 cells. Genes were classified as bivalent if both H3K4me3 signal and H3K27me3 signal were ≥4-fold over input in the TSS±500 bp region. The inventors found that there was an overall decrease in the total number of bivalent genes in H1299 T18 compared to Parental cells (Bar graph in FIG. 17B), correlating with increased KDMs in T18. The inventors saw that a great majority of these genes (~80%) showed at least a 2-fold signal loss. The inventors next classified the "bivalency lost" genes by loss of H3K4me3, loss of H3K27me3 or loss of both marks (Pie chart in FIG. 17B). The inventors found that many of the genes which had lost their bivalency in H1299 T18 compared to H1299 Parental, regained these marks (at least a 1.5-fold increase) after short-term GSK-J4 or JIB-04 treatment of T18 cells (shown by category in FIG. 17C).

Figure 20A:
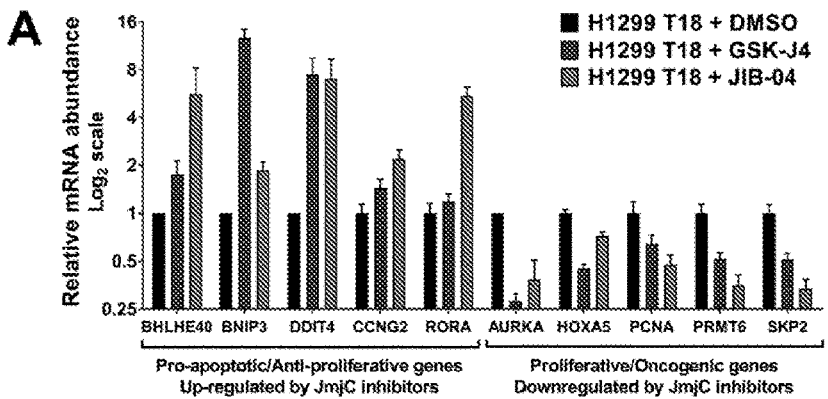
FIGS. 20A-20F. JmjC inhibitor treatment causes upregulation of pro-apoptotic genes and down-regulation of proliferative genes, without altering MDR1 expression or histone methylation in short-term treated H1299 T18 cells.
Figure 20B:
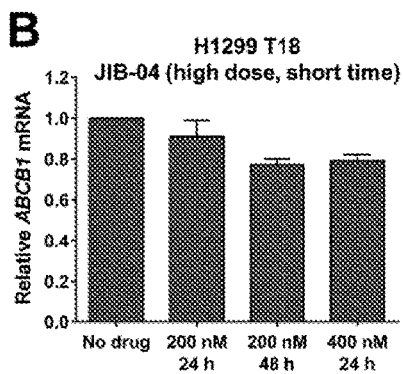
Figure 20C:
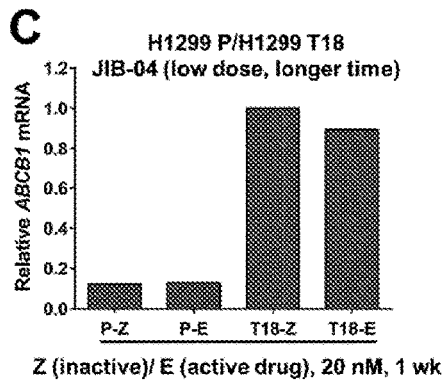
Figure 20D:
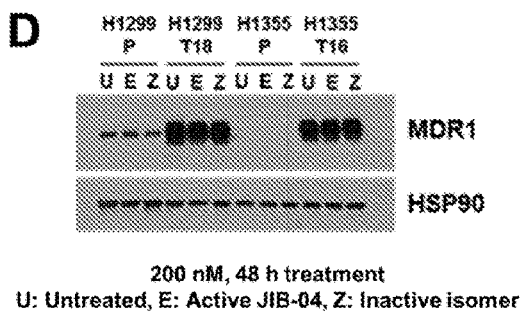
Figure 20E:
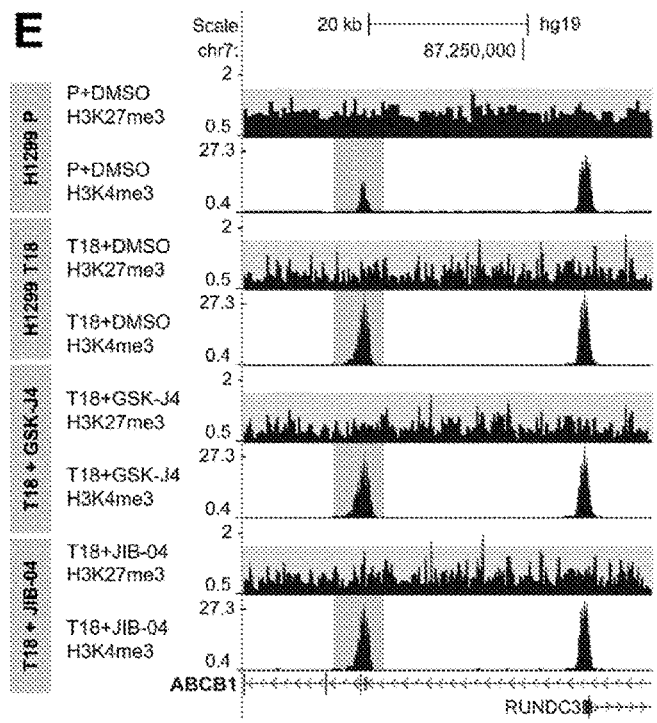
Figure 20F:
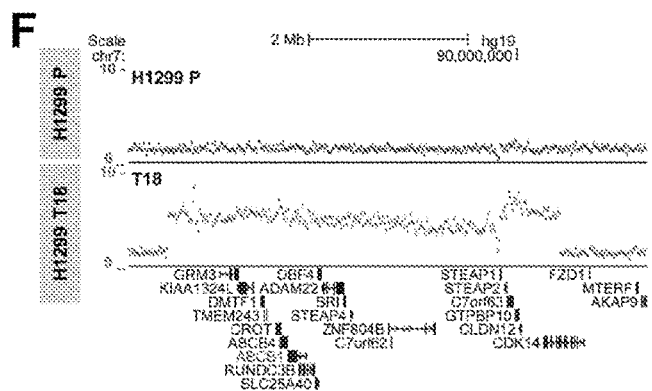

To validate the apoptotic gene set enrichment uncovered by GSEA from the microarray data, the inventors queried known apoptotic genes from the Martoriati gene set (FIG. 17A, right) in the RNA-seq dataset. As shown in FIG. 17D, these pro-apoptotic genes were found to be significantly up-regulated by short-term JmjC inhibitor treatment of T18 cells. Additionally, these and some other pro-apoptotic/anti-proliferative genes were confirmed by qRT-PCR to be up-regulated by both JIB-04 and GSK-J4, whereas proliferative/oncogenic genes were found to be significantly down-regulated in JmjC inhibitor-treated T18 cells (FIG. 20A). ChIP-seq traces of sample pro-apoptotic genes up-regulated by JmjC inhibitors, DDIT4 and BNIP3, are shown in FIGS. 17E and 17F, respectively, exhibiting greater enrichment of the H3K4me3 activating mark. In contrast, histone marks at the MDR1 locus were not altered by Jumonji inhibitor treatment nor was MDR1 expression as expected from its genetic amplification (FIGS. 20B-20F). The expression of MDR1 was not altered by treatment with JIB-04 or GSK-J4 in H1299 T18 cells.

Example 12

JmjC KDM Inhibitors Synergize with Taxane-Platin Standard Chemotherapy and Prevent Emergence of Drug Tolerance from Parental Populations Given the hypersensitivity of chemoresistant cells to JmjC KDM inhibitors, and the transcriptional reprogramming seen in resistant cells, the inventors asked whether JIB-04 or GSK-J4 would synergize with standard taxane+platin chemotherapy in killing chemoresistant clones. Using JIB-04 or GSK-J4 doses that were pre-determined to not cause complete growth inhibition as single agents, the inventors found that both of these drugs were effective in causing synergistic growth inhibition of H1299 T18 chemoresistant colonies that would otherwise survive taxane+platin chemotherapy (indicated by positive delta Bliss in FIGS. 8A-8B).

Figures 8A, 8B, 8C, 8D, 8E:
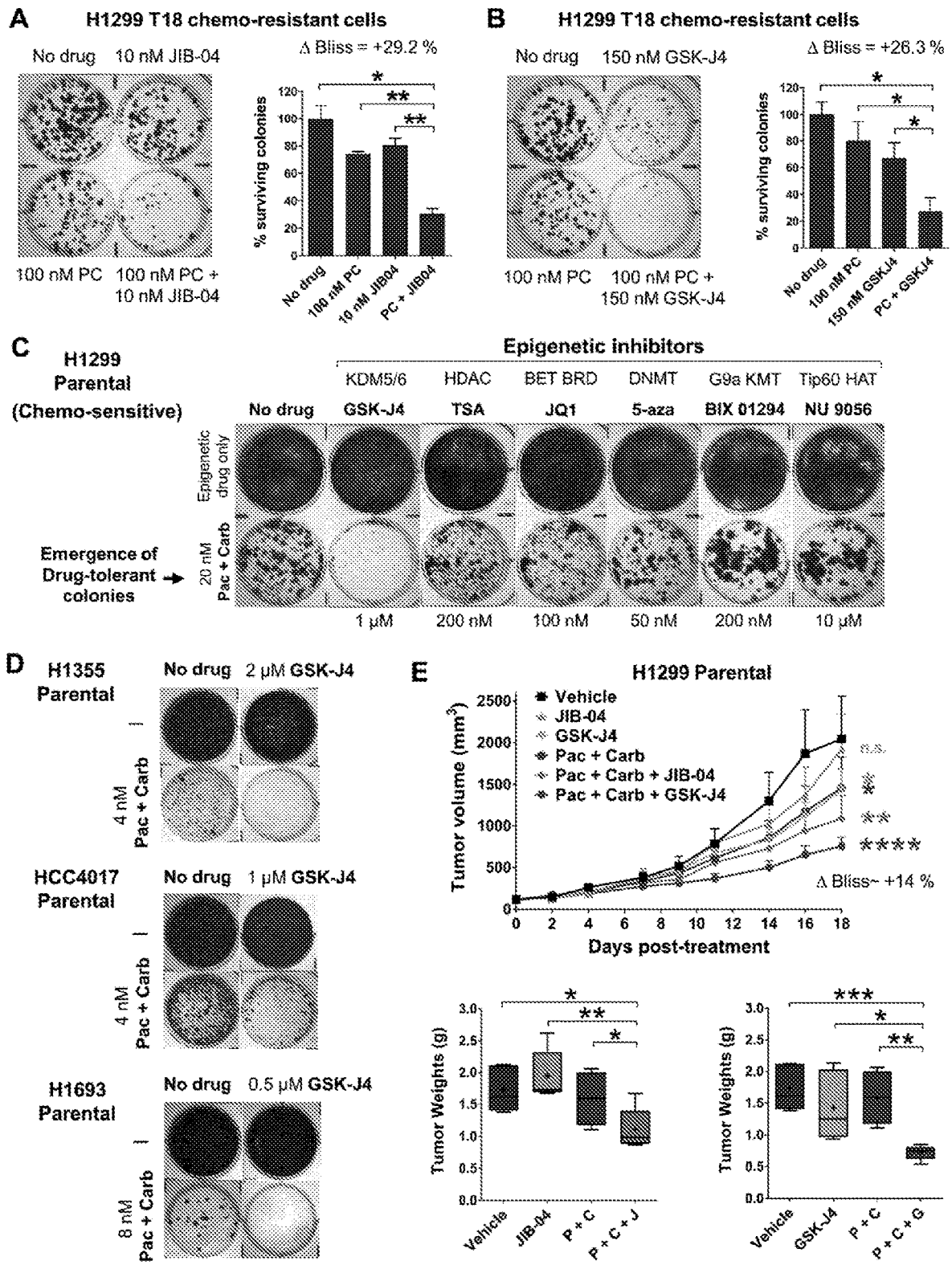
FIGS. 8A-8E. JmjC KDM inhibitors synergize with paclitaxel+carboplatin standard chemotherapy in blocking emergence of drug tolerance from chemo-sensitive NSCLCs in vitro and in vivo.

The inventors also investigated the possibility of blocking the emergence of drug-tolerant colonies from taxane-platin sensitive, chemo-naïve parental cell lines. H1299 Parental cells were exposed to paclitaxel+carboplatin doublet under conditions that allowed for a surviving subpopulation. The inventors evaluated the impact of sub-lethal doses of various epigenetic compounds in inhibiting survival and colony forming ability of these taxane-platin 'persister' cells (FIG. 8C). Only the JmjC KDM inhibitor GSK-J4 prevented the emergence of drug-tolerant persister colonies from H1299 Parental cells, whereas inhibitors of other epigenetic enzymes did not (FIG. 8C). Next, the inventors assessed the ability of GSK-J4 in blocking the outgrowth of persister colonies from other chemo-sensitive NSCLC cell lines. H1355, HCC4017 and H1693 Parental cells were exposed to their respective pre-determined paclitaxel+carboplatin doublet concentrations that allowed for a surviving subpopulation. Sub-lethal doses of GSK-J4 inhibited the outgrowth of these taxane-platin drug-tolerant colonies (FIG. 8D).

The inventors therefore evaluated the impact of JmjC KDM inhibitors in vivo in combination with standard taxane-platin chemotherapy in achieving better therapeutic outcomes from chemo-sensitive, parental tumors. Combination of JIB-04 or GSK-J4 with paclitaxel+carboplatin chemotherapy resulted in significantly greater tumor growth inhibition than single agents with a synergistic response in H1299 Parental xenografts (FIG. 8E, top panel, positive delta Bliss). There was significant reduction in final tumor burden compared to either therapy alone (FIG. 8E, bottom, tumor weights), without any appreciable toxicity in treated mice.

Example 13

Figures 18A, 18B, 18C, 18D, 18E:
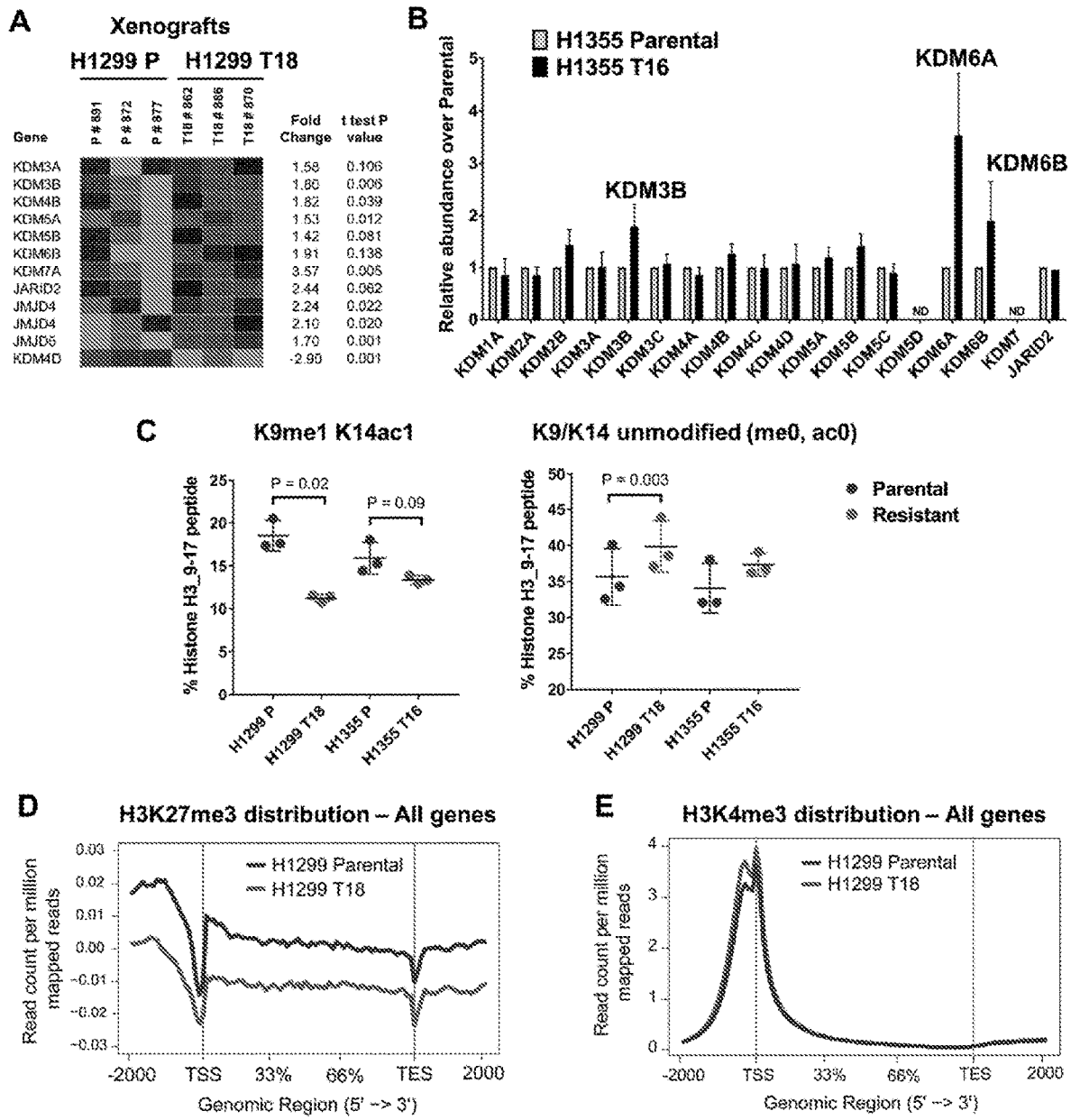
FIGS. 18A-18E. Chemoresistant NSCLC cells exhibit increased KDM expression and altered histone methylation levels by mass spectrometry and ChIP-sequencing.
Figures 19A, 19B, 19C, 19D, 19E:
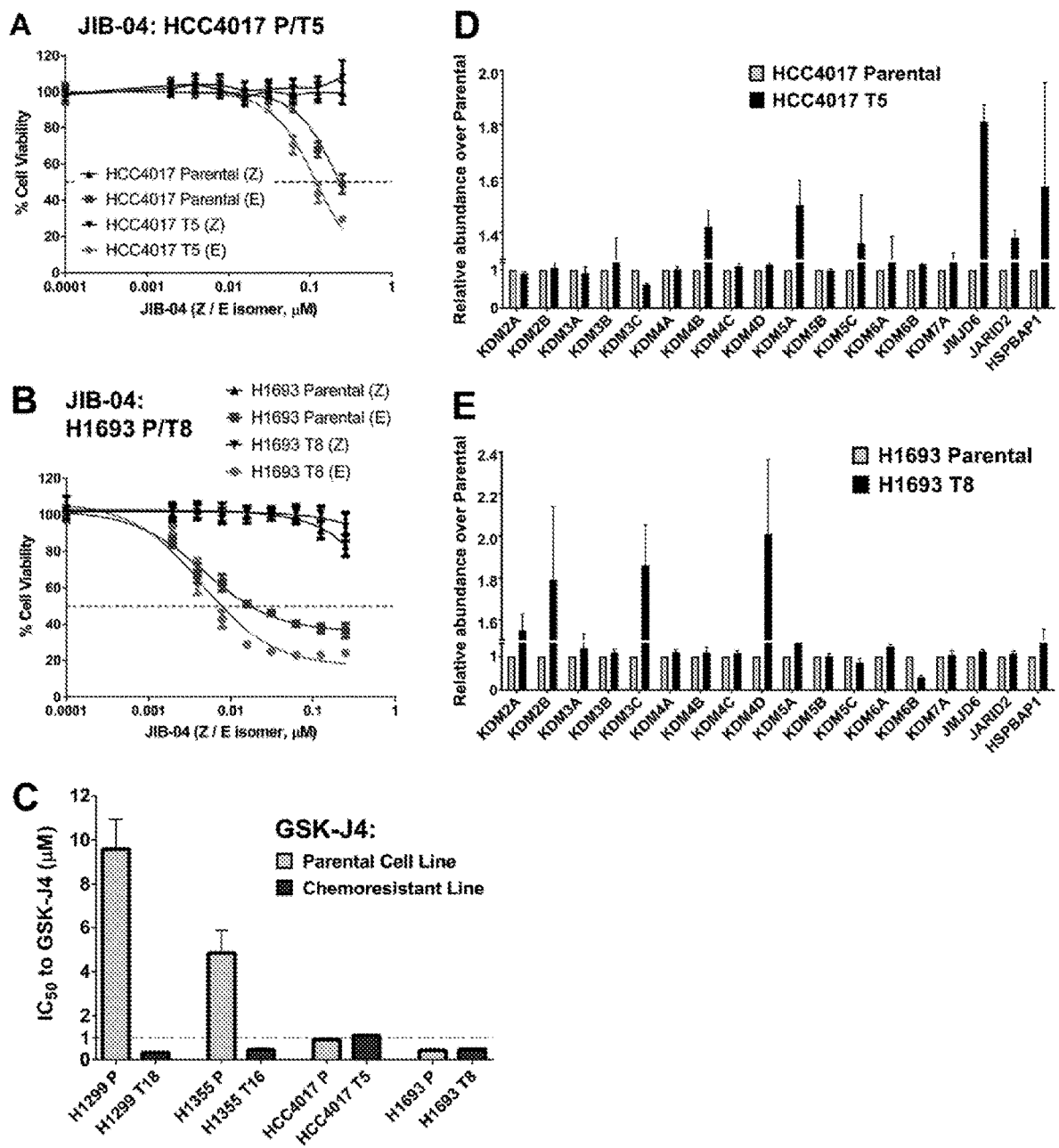
FIGS. 19A-19E. HCC4017 T5 and H1693 T8 chemoresistant cells show increased sensitivity to the pan-KDM inhibitor JIB-04, but not to the KDM6 specific inhibitor GSK-J4.

Inhibition of Jumonji Enzymes with JIB-04 Enhances the Response of Cancer Cells to Radiation, Linearizing it Whether inhibition of Jumonji enzymes would enhance the response to radiation due to the underlying connection between the epigenetic landscape, histone modifications and DNA repair was evaluated. To this end, radioresistant NSCLC lines H1299 or A549 were treated with JIB-04 and 4 h later exposed the cells to increasing levels of ionizing radiation in standard colony formation assays. As can be seen in FIGS. 22A-22D, colony formation IC50 doses of JIB-04 were first calculated (FIG. 22A) then used in combination with radiotherapy. Only the active E-isomer of JIB-04 had a radiosensitization/radioenhancement effect. This effect was very robust (FIG. 22B), linearizing the response and decreasing the survival fraction at 2 Gy of radiation (SF2) of all radioresistant NSCLC liens tested while not affecting already radiosensitive lines (FIGS. 22C, 18). Moreover, treatment of tumor bearing mice with the combination of JIB-04 and IR gave synergistic robust inhibition of tumor growth compared to either treatment alone and this therapeutic response was maintained even weeks after treatment ended (FIG. 22D).

Figures 24A, 24B:
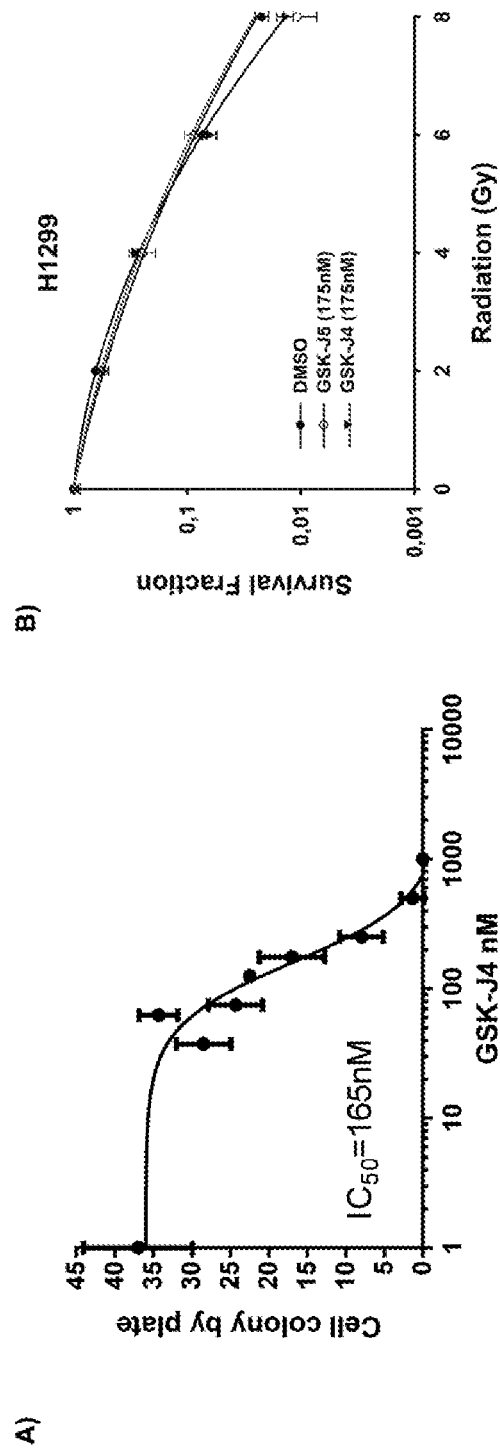
FIGS. 24A-24B. GSK-J4, a preferentially H3K27me3 demethylase inhibitor, doesn't affect the sensitivity of H1299 cells to IR.

The Jumonji H3K27me3 demethylase inhibitor GSK-J4 did not have this effect and failed to radiosensitize NSCLC H1299 or A549 (FIG. 24). This suggested that the sensitization effect was mediated by inhibition of other Jumonji demethylases including targets of JIB-04.

Example 14

Radioenhancement/Radiosensitization is Optimal with JIB-04 Pre-Treatment

Figures 25A, 25B:
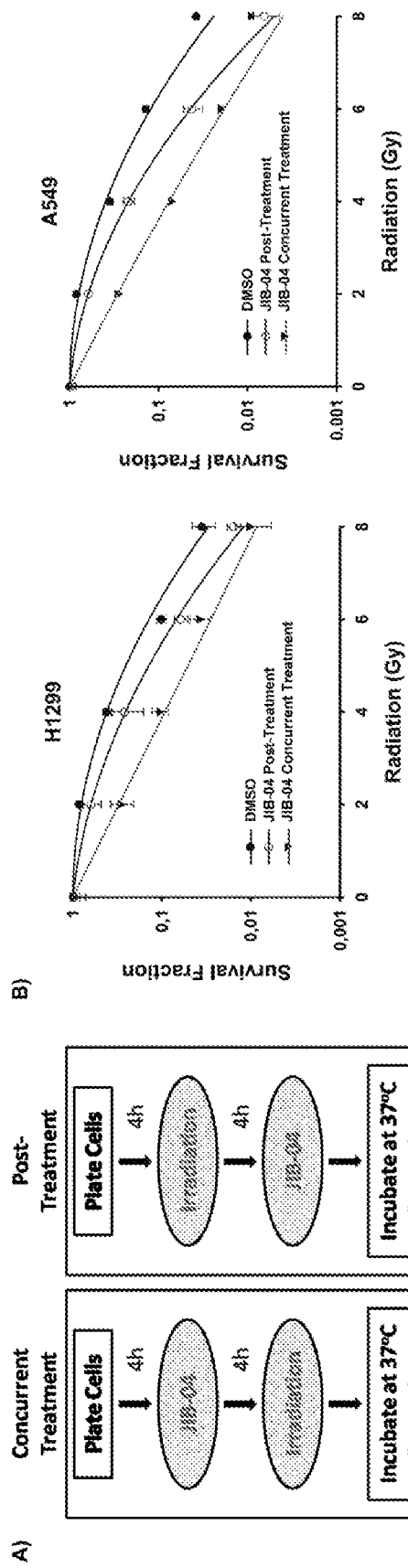
FIGS. 25A-25B. Concurrent treatment of NSCLC cells with JIB-04 reduces clonogenic survival while post-treatment reduces the JIB-04 efficiency as a radiosensitizer.
Figures 26A, 26B:
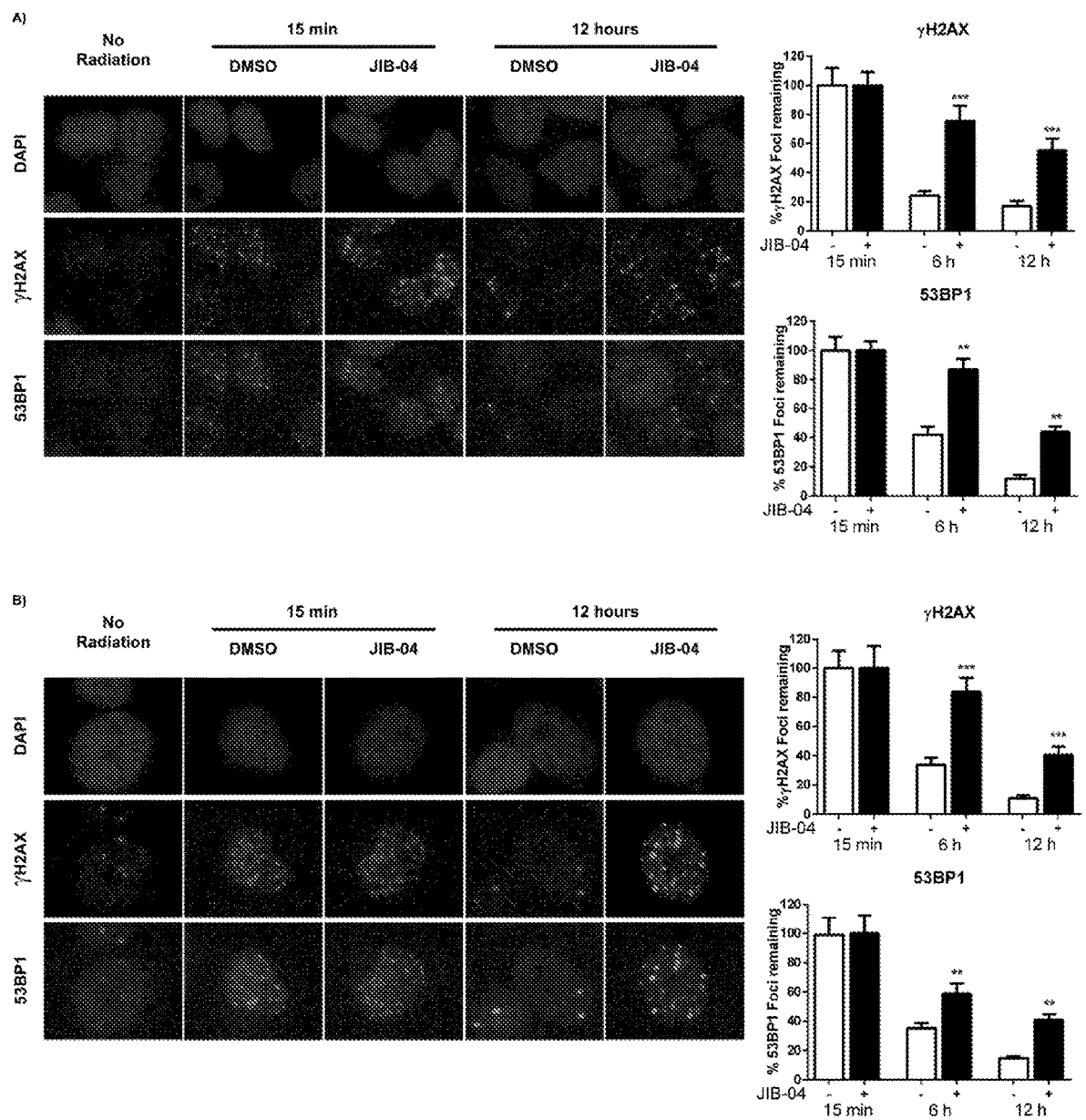

To evaluate optimal timing of Jumonji inhibition to obtain radiosensitizing effects, essentially what was described above for FIGS. 17A-17D was "compared concurrent," to post-treatment in which JIB-04 was administered 4 h post-irradiation rather than prior to irradiation. Sensitization was observed under both conditions but was significantly more robust when administering JIB-04 first in NSCLC lines (FIG. 25).

Example 15

γH2AX and 53BP1 Foci Resolution after IR are Delayed by JIB-04 but not by GSK-J4 Treatment in Cancer Cells To investigate the mechanisms that may contribute to radiosensitization, the effects of JIB-04, a pan-inhibitor of Jumonji enzymes which show radiosensitized, or of GSK-J4, reported to mainly inhibit H3K27 demethylases which do not show radiosensitize was evaluated on the DNA repair process. Repair proficient NSCLC cells H1299 and A549 were pretreated for 4 h with colony formation $IC_{50}$ doses of Jumonji inhibitors and then exposed to IR in the continuous presence of drug. It was found that ATM signaling occurred normally initiating the DNA damage signaling cascade and inducing γH2AX foci formation in JIB-04 and GSK-J4 treated cells (FIGS. 21A-21B and not shown). Resolution of γH2AX foci, however, was significantly impaired in the presence of Jumonji inhibitor JIB-04 with >30% of foci remaining unresolved in JIB-04 treated cells even at late time points (FIGS. 21A-21B). Similarly, 53BP1 foci resolution was defective in cells treated with IR and JIB-04 compared to IR alone (FIGS. 21A-21B). These defects were not observed in GSK-J4 treated cells. Again, the JIB-04 induced defects on γH2AX and 53BP1 foci resolution were seen in all radioresistant NSCLC lines in parallel with radiosensitization induced by the drug but not by cancer cells already sensitive to radiation (FIGS. 21C, 17C). Overall, this suggests H3K4/K9/K36 or H4K20 demethylase but not H3K27 demethylase involvement in radiosensitization.

Example 16

Figures 27A, 27B, 27C:
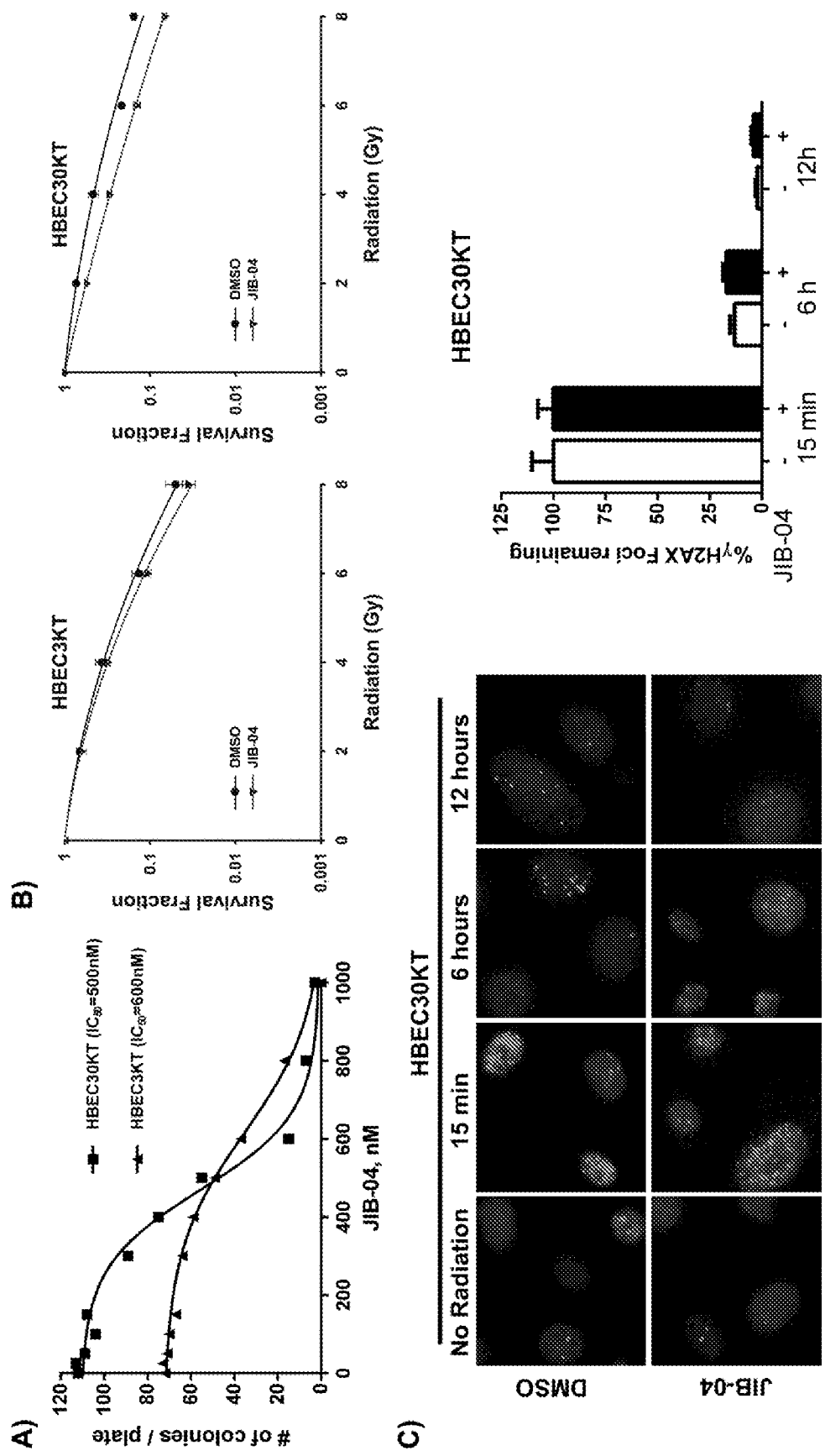
FIGS. 27A-27C. JIB-04 increased the sensitivity of radioresistant cells in a cancer-selective manner.

Inhibition of Jumonji Enzymes with JIB-04 does not Radiosensitize Nor Affect the DNA Repair Dynamics of Normal Cells To evaluate whether the effect of JIB-04 on DNA repair dynamics described above was cancer-selective, IC50 doses of JIB-04 in colony formation assays of immortalized normal human bronchial epithelial cells HBEC3KT and HBEC30KT were calculated (FIG. 27A). Then these doses of JIB-04 were used to pretreat cells 4 h prior to radiation and survival was measured. Remarkably, JIB-04 did not radiosensitize these normal cells (FIG. 27B), suggesting its effects are cancer-specific. In agreement with these findings, γH2AX foci formation in response to IR and foci resolution over a time course showed no defects, indicating that the DNA repair deficiency triggered by JIB-04 is also cancer-selective (FIG. 27C). Thus both the anti-proliferative effects of this Jumonji inhibitor as previously reported by us, as well its impact on DNA repair dynamics and radiosensitization appear to be restricted to cancer cells.

Example 17

JIB-04 Lowers the Efficiency of NHEJ and HR

To further understand the reasons for the delayed resolution of IR-induced damage seen in cancer cells in the presence of JIB-04, the efficiency of repair by non-homologous end joining (NHEJ) and homologous recombination (HR) were measured, the two main mechanisms of cellular DSB repair. Established plasmid-based reporter systems were used for this purpose. H1299 cells containing the stably integrated NHEJ or HR constructs depicted in FIG. 28A were transfected with an I-Sce1 expression vector and an mCherry plasmid to control for transfection efficiency. Transfected cells treated with JIB-04 or vehicle were then assayed for GFP expression by FACs as a measure of repair efficiency. As demonstrated in FIGS. 28B and C both NHEJ and HR were significantly inhibited in the presence of JIB-04 to approximately 50% or less of normal levels. These results were confirmed in other cell line models, including U2OS osteosarcoma cells, which gave highly similar results (FIG. 29) and also indicated that the JIB-04 induced defects in DNA repair and the observed radiosensitization are generalizable to other cancer types. This was also confirmed in a prostate cancer cell line, LNCap, where it was also observed defects in γH2AX foci resolution in response to JIB-04 treatment and IR (data not shown). Taken together, these results point to a common upstream defect caused by JIB-04 in the repair of DSBs, affecting both NHEJ and HR efficiency across cancers. To validate this, the cell cycle and then recruitment of repair factors to sites of DSBs were measured next.

Example 18

JIB-04 Doses that Cause DNA Repair Defects and Radiosensitization do not Affect Cell Cycle Distribution It was established that JIB-04 induced defects in DNA repair dynamics were not the result of JIB-04 altering the distribution of cells through the cell cycle nor of impeding the signature G2/M arrest cause by IR, as seen in FIG. 30. Indeed neither H1299 nor A549 cells treated with JIB-04 at doses and time points that alter γH2AX foci resolution shown any alteration in cell cycle distribution compared to DMSO treated cells with or without radiation treatment. Thus the JIB-04 effects observed above cannot be solely nor mainly due to cell cycle effects caused by inhibitor treatment.

Example 19

Recruitment of RAD51 and of DNA-PKcs are Diminished by JIB-04

Figure 31:
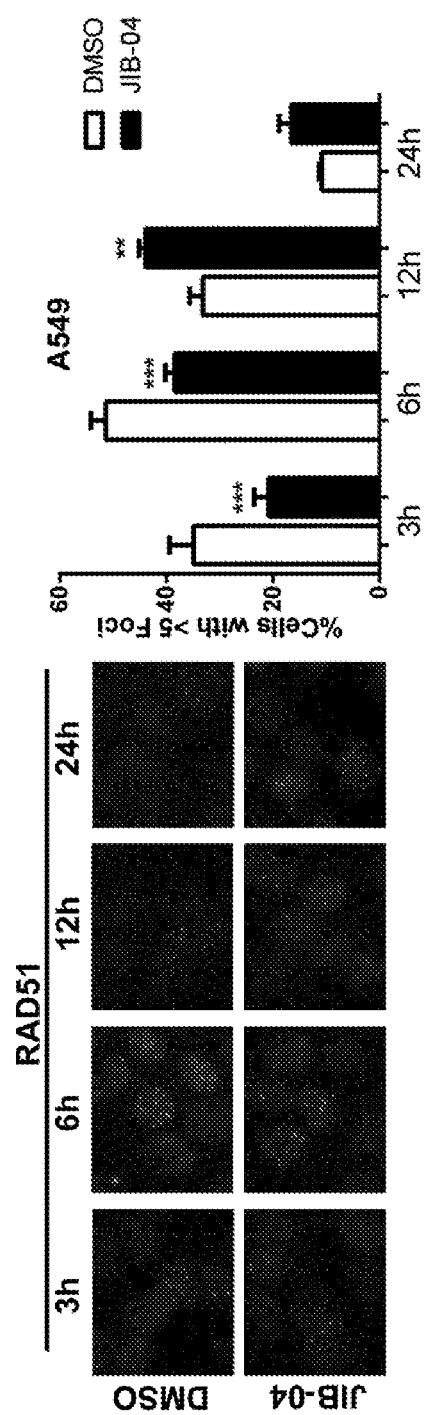
FIG. 31. JIB-04 delays RAD-51 foci formation and resolution during HR. RAD-51 foci kinetics in H1299 cells. Cells were incubated with (black bar) or without (white bar) JIB-04 for 4 h (25 nM), irradiated (10 Gy), immunostained for RAD-51 and then foci per nucleus counted for each time point (>100 nuclei counted). RAD-51 representative immunofluorescence images are shown on left panel. Foci formation and resolution kinetic was obtained by plotting the %±SEM of cells with more that 5 foci against time, in the right panel. *p<0.001, p<0.01 vs control, ANOVA. Data is representative of one of two experiments.
Figures 32A, 32B:
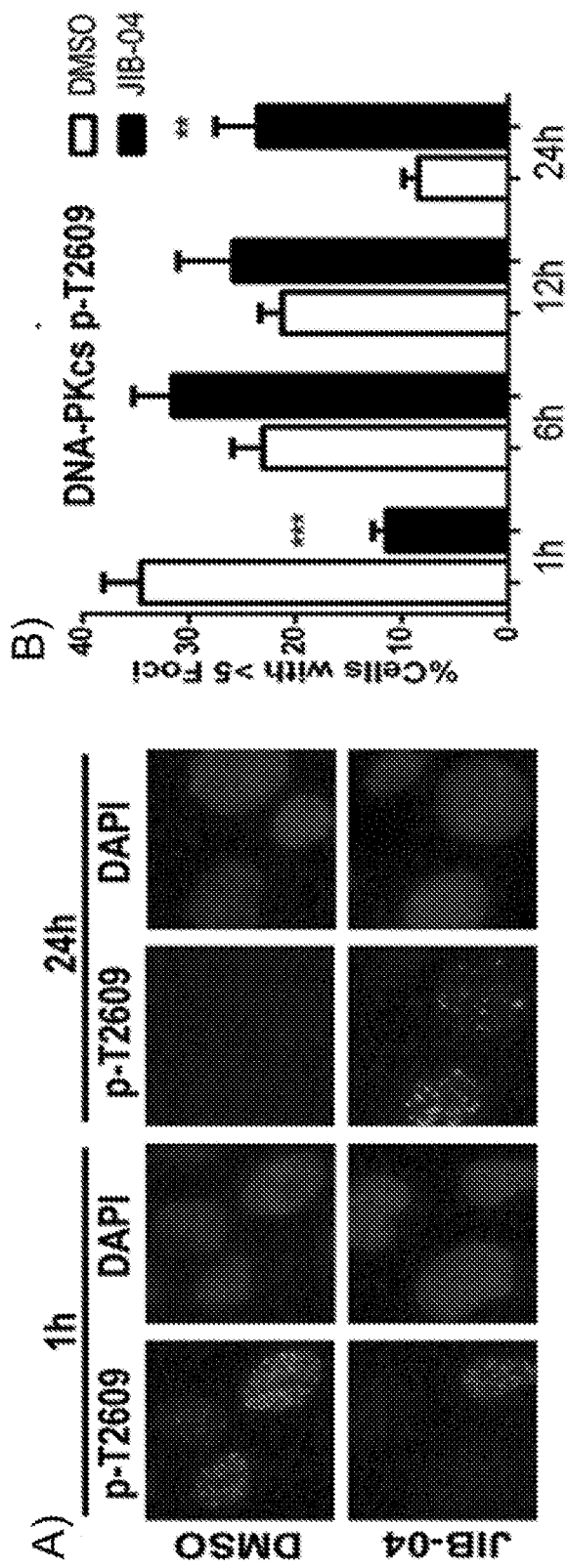
FIGS. 32A-32B. JIB-04 delays DNA-PKcs p-T2609 foci formation and resolution during NHEJ. DNA-PKcs p-T2609 kinetics in H1299. Cells were incubated with (black bar) or without (white bar) JIB-04 for 4 h (16 nM), irradiated (10 Gy), immunostained for DNA-PKcs p-T2609 and then foci per nucleus counted for each time point (>100 nuclei). Representative immunofluorescence of DNA-PKcs p-T2609 are shown (FIG. 32A) and quantified (FIG. 32B). Foci formation and resolution kinetic was obtained by plotting the %+SEM of cells with more that 5 foci against time. *p<0.001, p<0.01 *p<0.05 vs control, ANOVA. Data is representative of one of two experiments.

To determine if factors that mediate HR were not effectively recruited to sites of damage in the presence of JIB-04, RAD51 foci formation and resolution was measured over a time course. JIB-04 treatment significantly diminished RAD51 recruitment and in addition impaired foci resolution, with a large percentage of foci remaining at late time points (FIG. 31). A similar behavior was observed in H2199 cells (not shown).

DNA-PKcs gets recruited to DSBs to mediate repair by NHEJ. Since it was observed decreased efficiency of DNA repair by NHEJ after IR in cells treated with JIB-04, the recruitment of this NHEJ repair factor to DSBs was measured. H1299 cells treated with IR alone readily recruited DNA-PKcs to sites of damage by 1 h and these foci were largely resolved by 24 h (FIG. 27). In strong contrast, cells treated with JIB-04 and IR showed a robust deficiency in DNA-PKcs recruitment with foci not forming until 6 h post IR. In addition, the majority of DNA-PKcs foci remained unresolved even 24 h post irradiation (FIG. 27). Thus, JIB-04 impaired the timely recruitment of DNA-PKcs to sites of damage and blocked their resolution. Collectively, these data confirm that JIB-04 affects an aspect of DSB repair common to both NHEJ and HR.

Example 20

Figures 28A, 28B, 28C:
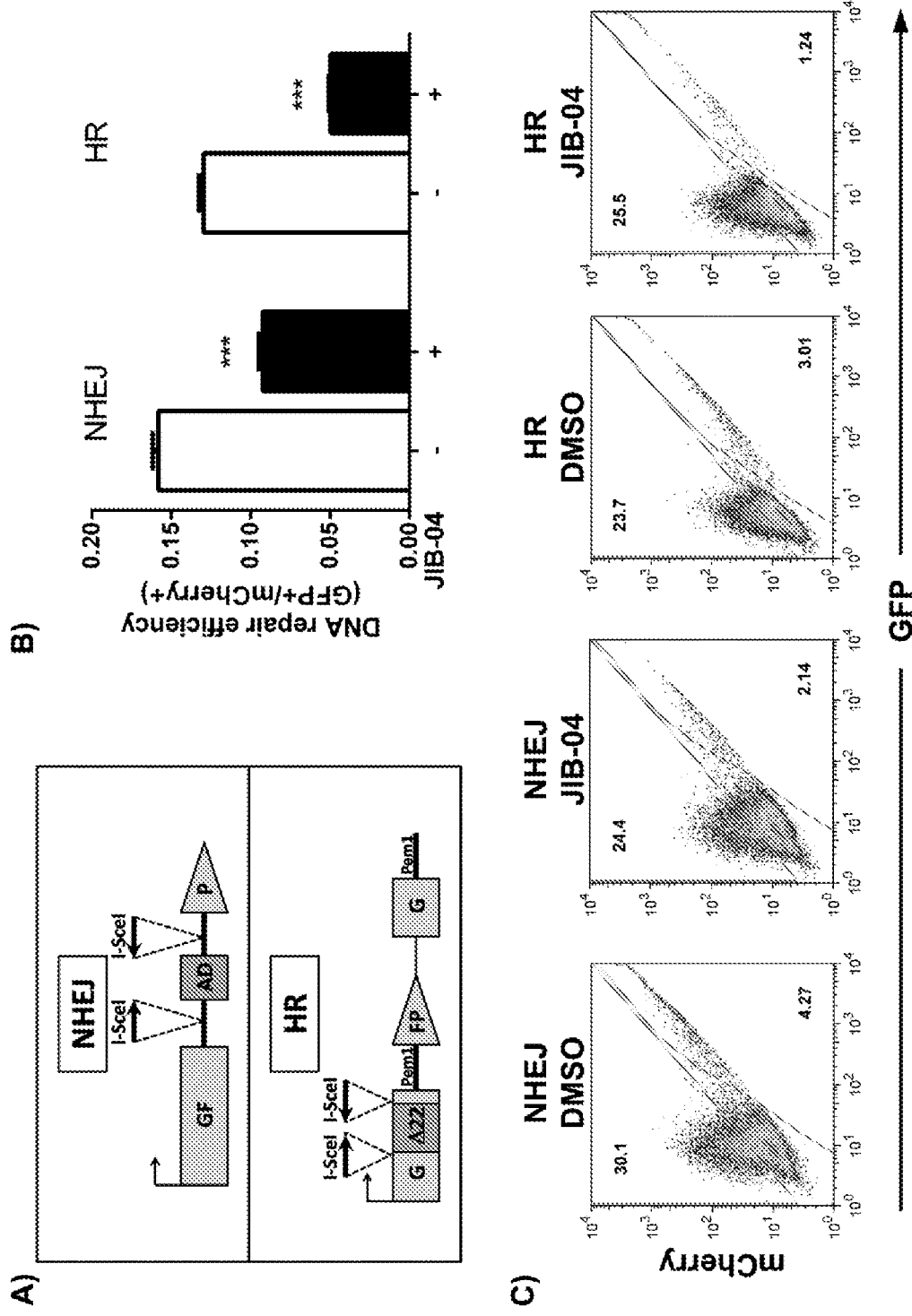
FIGS. 28A-28C. JIB-04 inhibits non-homologous end joining (NHEJ) and homologous recombination (HR) repair.
Figures 33A, 33B, 33C, 33D:
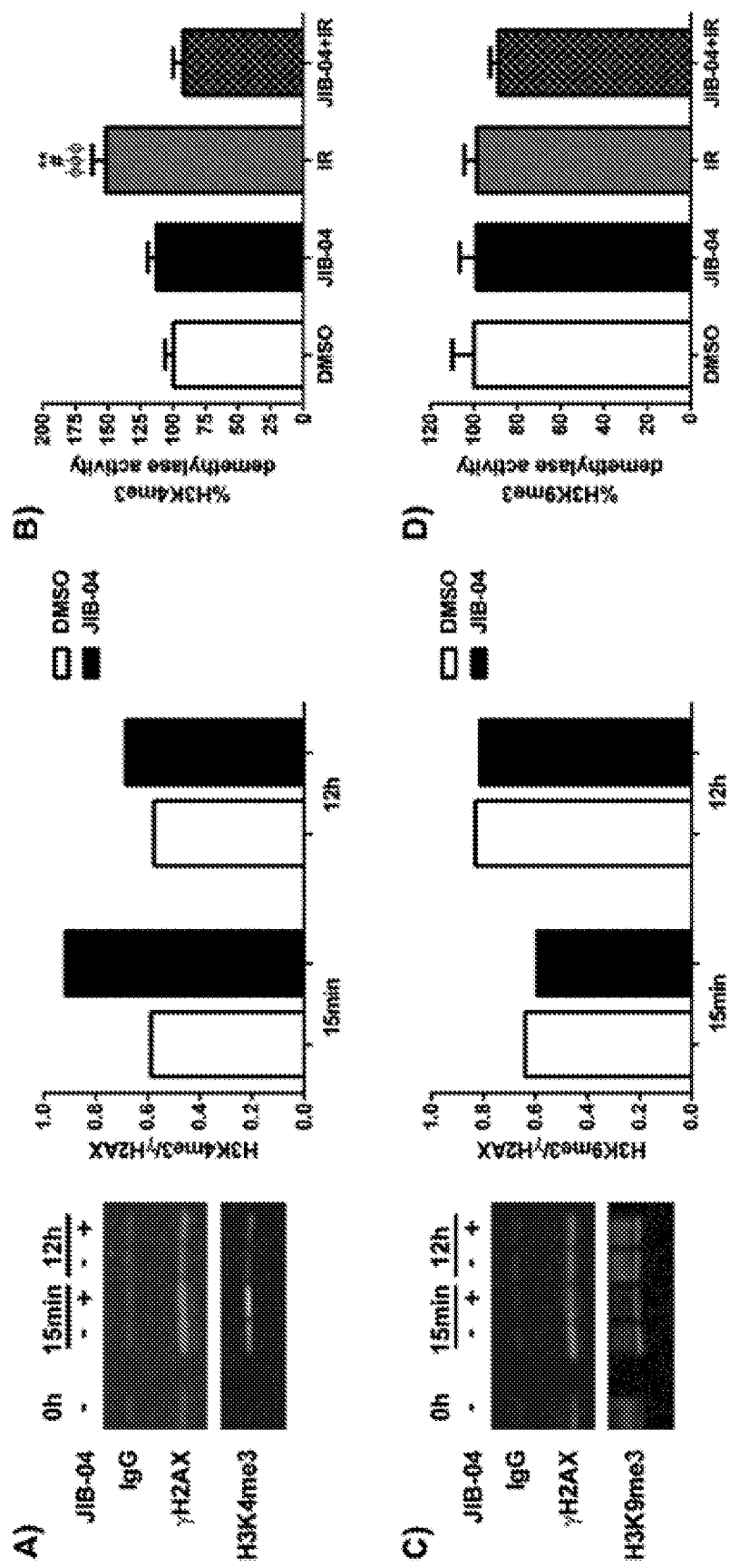
FIGS. 33A-33D. JIB-04 inhibits H3K4me3 demethylation at DSBs. Cells were incubated with (black bar) or without (white bar) JIB-04 for 4 h, irradiated (20 Gy), lysed and nucleosomes solubilized. γH2AX was immunoprecipitated from 2 mg of soluble nucleosome extract, and blotted for γH2AX and H3K4me3 (FIG. 33A) or H3K9me3 (FIG. 33C). The immunoblot data were quantified and expressed as the ratio H3K4me3 signal/γH2AX signal (FIG. 33A, right panel) or H3K9me3 signal/γH2AX signal (FIG. 33C, right panel). H1299 cells were pre-treated with JIB-04 during 4 h followed by IR (8 Gy) and collected at 15 min after radiation. Cellular extracts were prepared and H3K4me3 (FIG. 33B) or H3K9me3 (FIG. 33D) demethylase activity measured. Values are expressed as %+SEM of DMSO treated controls. **p<0.01 vs DMSO, #p<0.05 vs JIB-04 and ΦΦΦp<0.001 vs JIB-04+IR. Data is representative of one of three experiments.
Figures 34A, 34B, 34C:
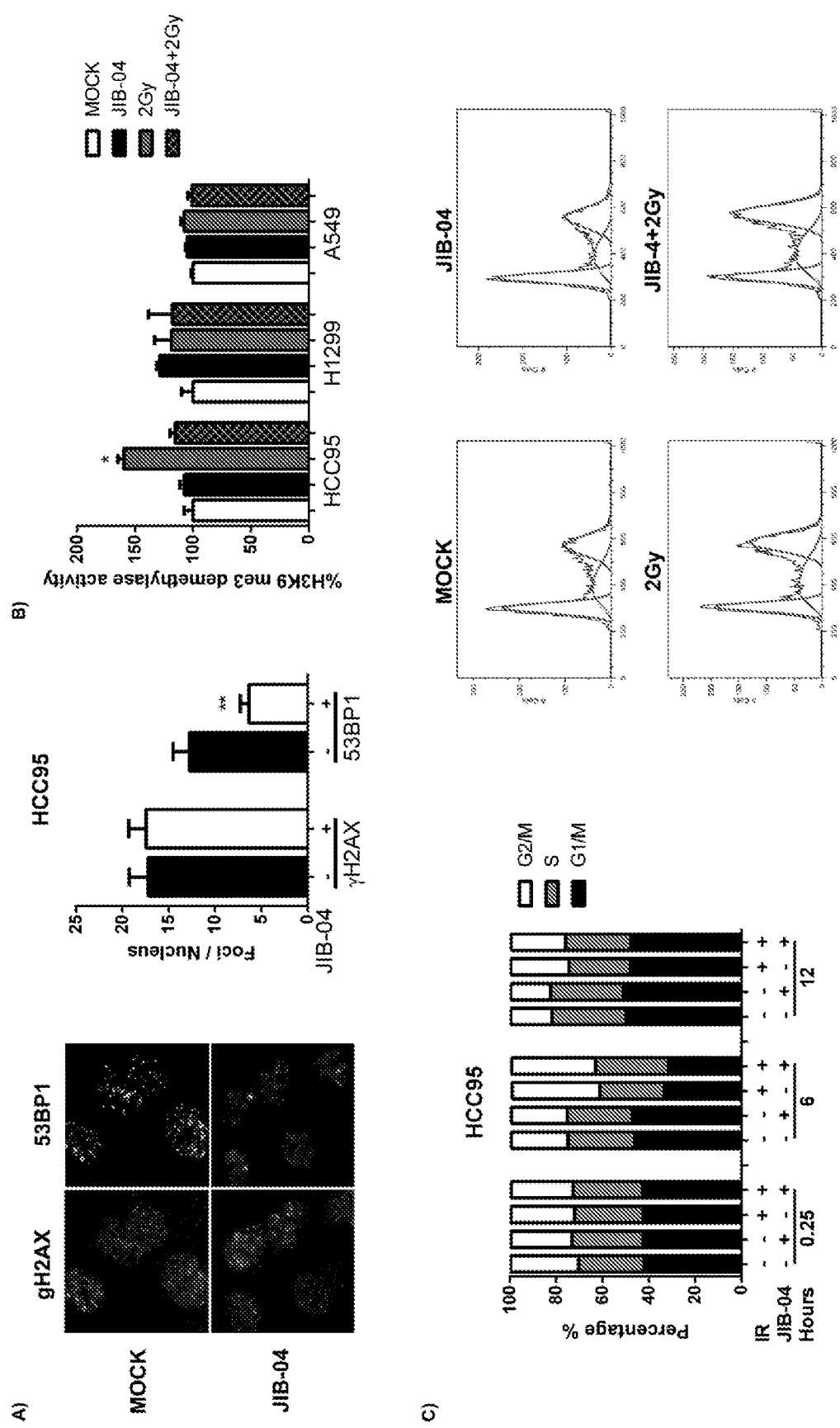
FIGS. 34A-34C. IR sensitization by JIB-04 was associated with a delayed 53BP1 foci formation and resolution in a subset of NSCLC cells.

Jumonji Inhibition by JIB-04 Results in H3K4Me3 but not H3K9Me3 Enrichment at DSBs It is known that heterochromatin marked by H3K9me3 is more refractory to DNA repair than euchromatin. It has also been established that H3K4me3 at transcriptionally active genes must be demethylated upon DNA damage, in order to stop transcription until the DNA is repaired. Since inhibition of Jumonji histone demethylase enzymes with JIB-04 can result in increased histone methylation levels, it was hypothesized that H3K4me3 or H3K9me3 marks may be accumulating at DSBs in JIB-04 treated cells. To test this possibility, immunoprecipitation of γH2AX at DSB sites after treatment with JIB-04 or vehicle and IR was performed followed by measuring H3K4me3 or H3K9me3 levels at these DSB sites. No changes in H3K9me3 induced by JIB-04 at sites of DNA damage marked by γH2AX (FIG. 28C) but that JIB-04 induced increased H3K4me3 was found at these sites (FIG. 28A). This indicates that an H3K4me3 demethylase Jumonji enzyme(s) is inhibited in the presence of JIB-04, leading to accumulation of its substrate histone. Consistent with this result, it was found that upon IR, the enzymatic activity of H3K4me3 demethylase Jumonji enzymes, but not that of H3K9me3 demethylases, was increased and that JIB-04 blocked this increased activity (FIGS. 33B, 33D). JIB-04 did not have any effects on basal activity at the doses and short time points of treatment (FIGS. 33B, 33D).

Example 21

JIB-04 Prolongs Survival of Tumor Bearing Mice

Figures 29A, 29B:
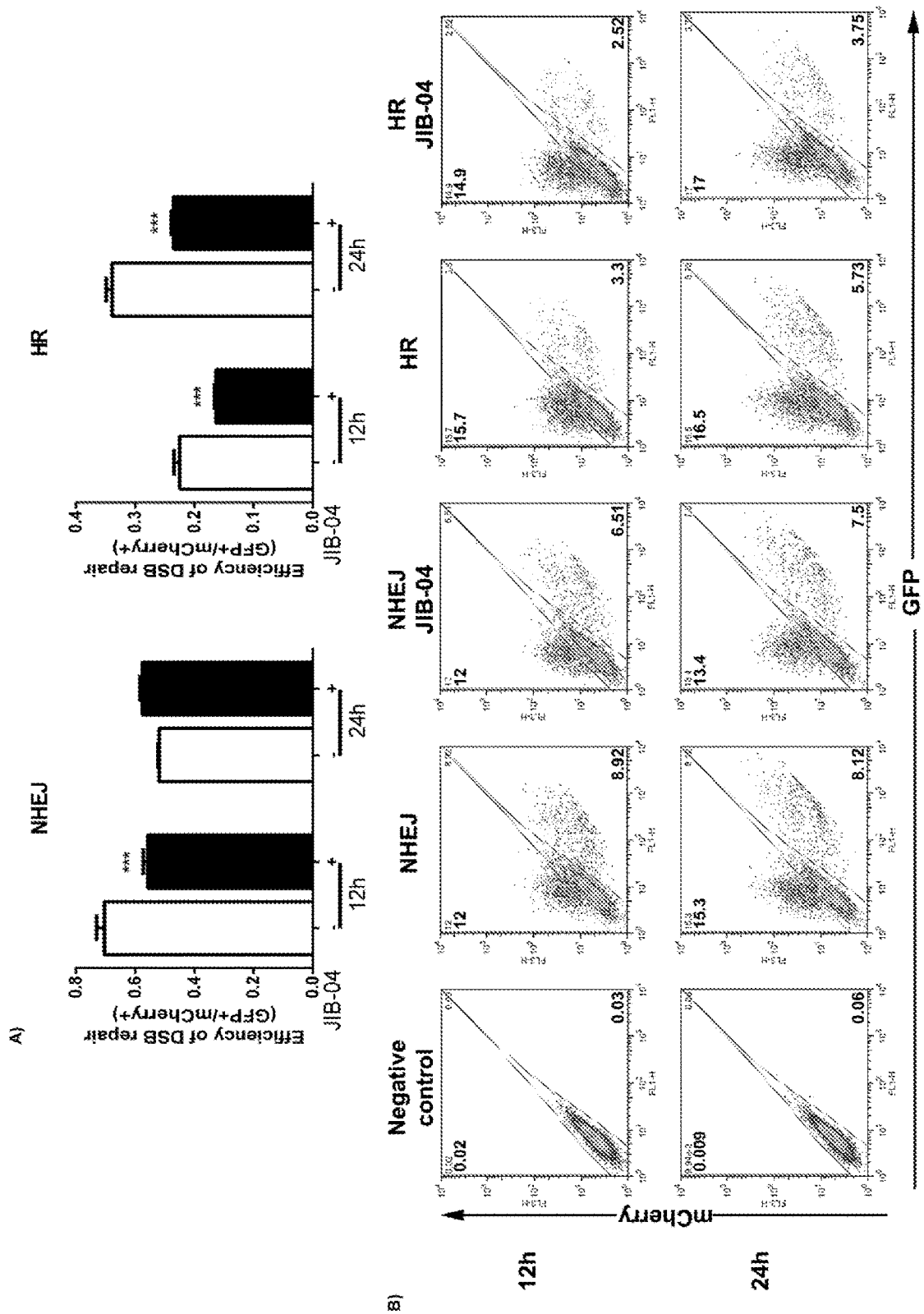
FIGS. 29A-29B. JIB-04 inhibits HR repair in U2OS cells.

Finally, it was evaluated if the radiosensitizing effects of JIB-04 would translate into longer survival of tumor bearing animals. Mice growing NSCLC xenografts of H1299 cells were treated with vehicle, radiation alone, JIB-04 alone or both and animal survival monitored over time. As can be seen in FIG. 29, the mice treated with IR and JIB-04 survived significantly longer than mice treated with either one alone or with vehicle and this was a sustained effect maintained even weeks post treatment.

All of the methods and apparatuses disclosed and claimed herein can be made and executed without undue experimentation in light of the present disclosure. While the compositions and methods of this invention have been described in terms of preferred embodiments, it will be apparent to those of skill in the art that variations may be applied to the methods and apparatuses and in the steps or in the sequence of steps of the methods described herein without departing from the concept, spirit and scope of the invention. More specifically, it will be apparent that certain agents which are both chemically and physiologically/functionally related may be substituted for the agents described herein while the same or similar results would be achieved. All such similar substitutes and modifications apparent to those skilled in the art are deemed to be within the spirit, scope and concept of the invention as defined by the appended claims.

REFERENCES

American Cancer Society (2015). Cancer Facts & Figures.

Ben-Porath, I., Thomson, M. W., Carey, V. J., Ge, R., Bell, G. W., Regev, A., and Weinberg, R. A. (2008). An embryonic stem cell-like gene expression signature in poorly differentiated aggressive human tumors. Nat Genet 40, 499-507.

Bertolini, G., Roz, L., Perego, P., Tortoreto, M., Fontanella, E., Gatti, L., Pratesi, G., Fabbri, A., Andriani, F., Tinelli, S., et al. (2009). Highly tumorigenic lung cancer CD133+ cells display stem-like features and are spared by cisplatin treatment. Proceedings of the National Academy of Sciences of the United States of America 106, 16281-16286.

Bradshaw, D. M., and Arceci, R. J. (1998). Clinical relevance of transmembrane drug efflux as a mechanism of multidrug resistance. Journal of clinical oncology: official journal of the American Society of Clinical Oncology 16, 3674-3690.

d'Amato, T. A., Landreneau, R. J., Ricketts, W., Huang, W., Parker, R., Mechetner, E., Yu, I. R., and Luketich, J. D. (2007). Chemotherapy resistance and oncogene expression in non-small cell lung cancer. The Journal of thoracic and cardiovascular surgery 133, 352-363.

Ding, L. H., Xie, Y., Park, S., Xiao, G., and Story, M. D. (2008). Enhanced identification and biological validation of differential gene expression via Illumina whole-genome expression arrays through the use of the model-based background correction methodology. Nucleic Acids Res 36, e58.

Eisen, M. B., Spellman, P. T., Brown, P. O., and Botstein, D. (1998). Cluster analysis and display of genome-wide expression patterns. Proceedings of the National Academy of Sciences of the United States of America 95, 14863-14868.

Gottesman, M. M. (2002). Mechanisms of cancer drug resistance. Annu Rev Med 53, 615-627.

Gottesman, M. M., Fojo, T., and Bates, S. E. (2002). Multidrug resistance in cancer: role of ATP-dependent transporters. Nature reviews Cancer 2, 48-58.

Hashizume, R., Andor, N., Ihara, Y., Lerner, R., Gan, H., Chen, X., Fang, D., Huang, X., Tom, M. W., Ngo, V., et al. (2014). Pharmacologic inhibition of histone demethylation as a therapy for pediatric brainstem glioma. Nat Med 20, 1394-1396.

Ho, M. M., Ng, A. V., Lam, S., and Hung, J. Y. (2007). Side population in human lung cancer cell lines and tumors is enriched with stem-like cancer cells. Cancer research 67, 4827-4833.

Howlader N, N. A., Krapcho M, Garshell J, Miller D, Altekruse S F, Kosary C L, Yu M, Ruhl J, Tatalovich Z, Mariotto A, Lewis D R, Chen H S, Feuer E J, Cronin K A (eds) (1975-2012). SEER Cancer Statistics Review. In, (Bethesda, Md.: National Cancer Institute).

Kemper, K., de Goeje, P. L., Peeper, D. S., and van Amerongen, R. (2014). Phenotype switching: tumor cell plasticity as a resistance mechanism and target for therapy. Cancer research 74, 5937-5941.

Knoechel, B., Roderick, J. E., Williamson, K. E., Zhu, J., Lohr, J. G., Cotton, M. J., Gillespie, S. M., Fernandez, D., Ku, M., Wang, H., et a. (2014). An epigenetic mechanism of resistance to targeted therapy in T cell acute lymphoblastic leukemia. Nat Genet 46, 364-370.

Kruidenier, L., Chung, C. W., Cheng, Z., Liddle, J., Che, K., Joberty, G., Bantscheff, M., Bountra, C., Bridges, A., Diallo, H., et al. (2012). A selective jumonji H3K27 demethylase inhibitor modulates the proinflammatory macrophage response. Nature 488, 404-408.

Langmead, B., Trapnell, C., Pop, M., and Salzberg, S. L. (2009). Ultrafast and memory-efficient alignment of short DNA sequences to the human genome. Genome biology 10, R25.

Lemontt, J. F., Azzaria, M., and Gros, P. (1988). Increased mdr gene expression and decreased drug accumulation in multidrug-resistant human melanoma cells. Cancer research 48, 6348-6353.

Liu, J., Xiao, Z., Wong, S. K., Tin, V. P., Ho, K. Y., Wang, J., Sham, M. H., and Wong, M. P. (2013). Lung cancer tumorigenicity and drug resistance are maintained through ALDH(hi)CD44(hi) tumor initiating cells. Oncotarget 4, 1698-1711.

Mair, B., Kubicek, S., and Nijman, S. M. (2014). Exploiting epigenetic vulnerabilities for cancer therapeutics. Trends Pharmacol Sci 35, 136-145.

Martin, J., Ginsberg, R. J., Venkatraman, E. S., Bains, M. S., Downey, R. J., Korst, R. J., Kris, M. G., and Rusch, V. W. (2002). Long-term results of combined-modality therapy in resectable non-small-cell lung cancer. Journal of clinical oncology: official journal of the American Society of Clinical Oncology 20, 1989-1995.

Massarelli, E., Andre, F., Liu, D. D., Lee, J. J., Wolf, M., Fandi, A., Ochs, J., Le Chevalier, T., Fossella, F., and Herbst, R. S. (2003). A retrospective analysis of the outcome of patients who have received two prior chemotherapy regimens including platinum and docetaxel for recurrent non-small-cell lung cancer. Lung Cancer 39, 55-61.

Meissner, A., Mikkelsen, T. S., Gu, H., Wernig, M., Hanna, J., Sivachenko, A., Zhang, X., Bernstein, B. E., Nusbaum, C., Jaffe, D. B., et al. (2008). Genome-scale DNA methylation maps of pluripotent and differentiated cells. Nature 454, 766-770.

Rho, J. K., Choi, Y. J., Lee, J. K., Ryoo, B. Y., Na, I I, Yang, S. H., Kim, C. H., and Lee, J. C. (2009). Epithelial to mesenchymal transition derived from repeated exposure to gefitinib determines the sensitivity to EGFR inhibitors in A549, a non-small cell lung cancer cell line. Lung Cancer 63, 219-226.

Roesch, A., Fukunaga-Kalabis, M., Schmidt, E. C., Zabierowski, S. E., Brafford, P. A., Vultur, A., Basu, D., Gimotty, P., Vogt, T., and Herlyn, M. (2010). A temporarily distinct subpopulation of slow-cycling melanoma cells is required for continuous tumor growth. Cell 141, 583-594.

Roesch, A., Vultur, A., Bogeski, I., Wang, H., Zimmermann, K. M., Speicher, D., Korbel, C., Laschke, M. W., Gimotty, P. A., Philipp, S. E., et al. (2013). Overcoming intrinsic multidrug resistance in melanoma by blocking the mitochondrial respiratory chain of slow-cycling JARID1B (high) cells. Cancer cell 23, 811-825.

Roninson, I. B., Chin, J. E., Choi, K. G., Gros, P., Housman, D. E., Fojo, A., Shen, D. W., Gottesman, M. M., and Pastan, I. (1986). Isolation of human mdr DNA sequences amplified in multidrug-resistant K B carcinoma cells. Proceedings of the National Academy of Sciences of the United States of America 83, 4538-4542.

Scagliotti, G. V., Parikh, P., von Pawel, J., Biesma, B., Vansteenkiste, J., Manegold, C., Serwatowski, P., Gatzemeier, U., Digumarti, R., Zukin, M., et al. (2008). Phase III study comparing cisplatin plus gemcitabine with cisplatin plus pemetrexed in chemotherapy-naïve patients with advanced-stage non-small-cell lung cancer. Journal of clinical oncology official journal of the American Society of Clinical Oncology 26, 3543-3551.

Schiller, J. H., Harrington, D., Belani, C. P., Langer, C., Sandler, A., Krook, J., Zhu, J., Johnson, D. H., and Eastern Cooperative Oncology, G. (2002). Comparison of four chemotherapy regimens for advanced non-small-cell lung cancer. The New England journal of medicine 346, 92-98.

Sharma, S. V., Lee, D. Y., Li, B., Quinlan, M. P., Takahashi, F., Maheswaran, S., McDermott, U., Azizian, N., Zou, L., Fischbach, M. A., et al. (2010). A chromatin-mediated reversible drug-tolerant state in cancer cell subpopulations. Cell 141, 69-80.

Shen, L., Shao, N., Liu, X., and Nestler, E. (2014). ngs.plot: Quick mining and visualization of next-generation sequencing data by integrating genomic databases. BMC Genomics 15, 284.

Shien, K., Toyooka, S., Yamamoto, H., Soh, J., Jida, M., Thu, K. L., Hashida, S., Maki, Y., Ichihara, E., Asano, H., et al. (2013). Acquired resistance to EGFR inhibitors is associated with a manifestation of stem cell-like properties in cancer cells. Cancer research 73, 3051-3061.

Stewart, D. J., Chiritescu, G., Dahrouge, S., Banerjee, S., and Tomiak, E. M. (2007). Chemotherapy dose-response relationships in non-small cell lung cancer and implied resistance mechanisms. Cancer Treat Rev 33, 101-137.

Subramanian, A., Tamayo, P., Mootha, V. K., Mukherjee, S., Ebert, B. L., Gillette, M. A., Paulovich, A., Pomeroy, S. L., Golub, T. R., Lander, E. S., and Mesirov, J. P. (2005). Gene set enrichment analysis: a knowledge-based approach for interpreting genome-wide expression profiles. Proceedings of the National Academy of Sciences of the United States of America 102, 15545-15550.

Szakacs, G., Paterson, J. K., Ludwig, J. A., Booth-Genthe, C., and Gottesman, M. M. (2006). Targeting multidrug resistance in cancer. Nat Rev Drug Discov 5, 219-234.

Takebe, N., Harris, P. J., Warren, R. Q., and Ivy, S. P. (2011). Targeting cancer stem cells by inhibiting Wnt, Notch, and Hedgehog pathways. Nat Rev Clin Oncol 8, 97-106.

Thomson, S., Buck, E., Petti, F., Griffin, G., Brown, E., Ramnarine, N., Iwata, K. K., Gibson, N., and Haley, J. D. (2005). Epithelial to mesenchymal transition is a determinant of sensitivity of non-small-cell lung carcinoma cell lines and xenografts to epidermal growth factor receptor inhibition. Cancer research 65, 9455-9462.

Voulgari, A., and Pintzas, A. (2009). Epithelial-mesenchymal transition in cancer metastasis: mechanisms, markers and strategies to overcome drug resistance in the clinic. Biochim Biophys Acta 1796, 75-90.

Wang, L., Chang, J., Varghese, D., Dellinger, M., Kumar, S., Best, A. M., Ruiz, J., Bruick, R., Pena-Llopis, S., Xu, J., et al. (2013). A small molecule modulates Jumonji histone demethylase activity and selectively inhibits cancer growth. Nat Commun 4, 2035.

Wilson, C., Ye, X., Pham, T., Lin, E., Chan, S., McNamara, E., Neve, R. M., Belmont, L., Koeppen, H., Yauch, R. L., et al. (2014). AXL inhibition sensitizes mesenchymal cancer cells to antimitotic drugs. Cancer research 74, 5878-5890.

The invention claimed is:

1. A method for treating cancer in a subject in need thereof, the method consisting of administering to the subject a therapeutically effective amount of JIB-04 or GSK-J4, wherein the JIB-04 or GSK-J4 is administered as a monotherapy, wherein the cancer is non-small cell lung cancer, and wherein the non-small cell lung cancer is resistant to a cancer therapy.

2. The method of claim 1, wherein the JIB-04 or GSK-J4 inhibits one or more of KDM2A, KDM2B, KDM3A, KDM3B, KDM4A, KDM4B, KDM4C, KDM4D, KDM4E, KDM5A, KDM5B, KDM5C, KDM6A, KDM6B, PHF8, FBXL19, JMJD6, HIF1AN, MINA, and/or NO66.

3. A method of increasing the efficacy of a cancer therapy in a subject in need thereof consisting of administering to the subject a therapeutically effective amount of JIB-04 or GSK-J4, wherein the JIB-04 or GSK-J4 is administered as a monotherapy, wherein the cancer therapy treats a non-small cell lung cancer that has become resistant and/or is intrinsically resistant to the cancer therapy, and wherein the non-small cell lung cancer has been identified as one that has increased expression of two or more JmjC polypeptides relative to a subject having a non-small cell lung cancer that is sensitive to the cancer therapy.

4. The method of claim 3, wherein the JIB-04 or GSK-J4 inhibits one or more of KDM2A, KDM2B, KDM3A, KDM3B, KDM4A, KDM4B, KDM4C, KDM4D, KDM4E, KDM5A, KDM5B, KDM5C, KDM6A, KDM6B, PHF8, FBXL19, JMJD6, HIF1AN, MINA, and/or NO66.

5. The method of claim 4, wherein the JIB-04 or GSK-J4 affects H3K4, H3K9, H3K27, and/or H3K36 methylation.

6. The method of claim 5, wherein the affected H3K4, H3K9, H3K27, and/or H3K36 methylation results in blocking or delaying DNA repair in cancer cells that increases the efficacy of radiation.

7. The method of claim 1, wherein the administration prevents delays or inhibits the emergence of resistance in chemo-sensitive and/or untreated tumors.

8. The method of claim 1, wherein the non-small cell lung cancer has been identified as one that has increased expression of two or more JmjC polypeptides relative to a subject having a non-small cell lung cancer that is sensitive to the chemotherapy.

9. The method of claim 3, wherein the cancer therapy is chemotherapy or radiation therapy.

10. The method of claim 9, wherein the cancer is radio-sensitized and/or chemo-sensitized.

11. The method of claim 9, wherein the radiation therapy is x-rays and/or gamma rays.

12. The method of claim 3, wherein the administration targets chemo-resistant tumors after the development of radio-resistance.

13. The method of claim 3, wherein the administration prevents delays or inhibits the emergence of resistance in chemo-sensitive, radio-sensitive, and/or untreated tumors.

14. The method of claim 3, wherein the administration decreases toxicities of radiation.

15. A method for treating cancer in a subject in need thereof, the method consisting of administering to the subject a therapeutically effective amount of JIB-04 or GSK-J4, wherein the JIB-04 or GSK-J4 is administered as a monotherapy, wherein the cancer is non-small cell lung cancer, wherein the non-small cell lung cancer is resistant to a cancer therapy, and wherein administration of the JIB-04 or GSK-J4 targets chemoresistant tumors after the development of resistance.

* * * * *

UNITED STATES PATENT AND TRADEMARK OFFICE
CERTIFICATE OF CORRECTION

PATENT NO. : 11,497,740 B2
APPLICATION NO. : 16/097405
DATED : November 15, 2022
INVENTOR(S) : Dalvi et al.

It is certified that error appears in the above-identified patent and that said Letters Patent is hereby corrected as shown below:

In the Claims

In Claim 4, Column 71, Line 35, please delete "KDMS5A" and insert --KDM5A-- therefore.

In Claim 7, Column 72, Line 10, please delete "prevents" therefore.

In Claim 13, Column 72, Line 28, please delete "prevents" therefore.

Signed and Sealed this
Second Day of May, 2023

Katherine Kelly Vidal
*Director of the United States Patent and Trademark Office*